United States Patent [19]
Namiki et al.

[11] Patent Number: 5,942,515
[45] Date of Patent: Aug. 24, 1999

[54] PYRROLOPYRAZOLOPYRIMIDINE COMPOUND AND MEDICINE COMPRISING THE SAME AS ACTIVE INGREDIENT

[75] Inventors: Takayuki Namiki; Masayuki Yuasa; Takako Takakuwa; Satoshi Ichinomiya; Yukio Kawazu; Kenichi Kishii; Norio Funayama; Mariko Harada; Kyoko Taneda; Naoki Hiyama; Tomoaki Yahiro; Mayumi Sugio; Masashi Tamai, all of Yokohama, Japan

[73] Assignee: Pola Chemical Industries, Inc., Shizuoka, Japan

[21] Appl. No.: 09/017,223

[22] Filed: Feb. 2, 1998

[30] Foreign Application Priority Data

Feb. 3, 1997 [JP] Japan .................................. 9-020387

[51] Int. Cl.⁶ .................... A01N 43/54; C07D 239/00

[52] U.S. Cl. ................................ 514/267; 544/251

[58] Field of Search ................ 544/251; 514/267

[56] References Cited

U.S. PATENT DOCUMENTS

| 4,992,442 | 2/1991 | Tsujitani et al. | 514/267 |
|---|---|---|---|
| 5,086,057 | 2/1992 | Sasagawa | 514/267 |

OTHER PUBLICATIONS

Naoki Hiyama, et al., "Effect of Novel Bronchiadilator Drug PR–001337 on Bronchial Smooth Muscle of Guinea Pig", Journal of Smooth Muscle Research, Japanese Section, vol. 1, No. 2, (Jul. 1997), 4 pages. (English Translation 2 pages).

Primary Examiner—Mukund J. Shah
Assistant Examiner—Tamthom N. Truong
Attorney, Agent, or Firm—Oblon, Spivak, McClelland, Maier & Neustadt, P.C.

[57] ABSTRACT

The invention relates to compounds represented by the following general formula (1):

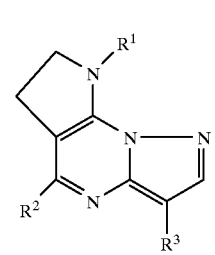

wherein $R^1$ represents an alkyl group, $R^2$ represents an amino group, alkyl group or the like, and $R^3$ represents a nitro group, amino group, heterocyclic group, alkylsulfonylamino group or the like, or salts thereof, medicines comprising such a compound, a preparation process of the compounds, and intermediates useful for preparation thereof. The compounds (1) are useful for the prevention and treatment of a respiratory disease.

15 Claims, No Drawings

PYRROLOPYRAZOLOPYRIMIDINE COMPOUND AND MEDICINE COMPRISING THE SAME AS ACTIVE INGREDIENT

TECHNICAL FIELD

The present invention relates to novel pyrrolo-[3,2-e]pyrazolo[1,5-a]pyrimidine compounds, a preparation process thereof, intermediates useful for preparation thereof, and medicines comprising such a compound as an active ingredient.

BACKGROUND ART

At present, bronchodilation by xanthine type bronchodilators typified by theophylline is mainly practiced for the prevention and treatment of respiratory diseases represented by asthma. Besides, beta-receptor stimuli such as ephedrine hydrochloride have been only used symptomatolytically.

However, all the above drugs have great side effects and hence have offered a problem. However, there has been nothing for its but to administer these drugs because any excellent drug substitutable for these drugs has not been yet found.

On the other hand, 3-cyano-5-methylpyrrolo[3,2-e]-pyrazolo[1,5-a]pyrimidines of compounds having a pyrrolo-[3,2-e]pyrazolo[1,5-a]pyrimidine skeleton have been known to have excellent vasodilative effect and tracheobronchodilative effect (Japanese Patent Publication No. 88999/1994). However, these compounds have been difficult to separate their action on circulatory organs such as hypotensive effect and their action on tracheas (or bronchus) from each other. It has therefore been desired to develop a drug which selectively acts on tracheas (or bronchus).

It is therefore an object of the present invention to provide a medicine which scarcely exhibits side effects and has excellent prophylactic and therapeutic effects on respiratory diseases.

DISCLOSURE OF THE INVENTION

In view of the foregoing circumstances, the present inventor has carried out an extensive investigation by syntheses, screening and the like with a view toward seeking compounds useful in the prevention and treatment of a respiratory disease. As a result, it has been found that novel compounds represented by the general formula (1), which will be described subsequently, or salts thereof have excellent tracheobronchodilative effect and inhibitory effect on airway constriction and act only weakly on circulatory organs, and are hence useful as prophylactic and therapeutic medicines for respiratory diseases, thus leading to completion of the present invention.

According to the present invention, there is thus provided a pyrrolopyrazolopyrimidine compound represented by the following general formula (1):

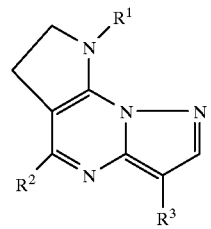

wherein $R^1$ represents a linear, branched or cyclic alkyl group, $R^2$ represents a hydrogen or halogen atom, an amino group which may be substituted, an alkyl group which may be substituted, a carboxyl group, an alkoxycarbonyl group, a carbamoyl group, or an alkylcarbamoyl group, and $R^3$ represents a nitro group, an amino group, a heterocyclic group, an alkylsulfonylamino group which may be substituted by halogen, $R^4$CONH— (in which $R^4$ represents an alkyl, halogenoalkyl, carboxyl or alkoxycarbonyl group), or $R^5$CO— (in which $R^5$ represents an amino, hydroxyl, alkyl, alkoxy, halogenoalkyl or heterocycle-amino group), or a salt thereof.

According to the present invention, there is also provided a medicine comprising the above compound (1) or the salt thereof as an active ingredient.

According to the present invention, there is further provided a medicinal composition comprising the above compound (1) or the salt thereof and a pharmaceutically acceptable carrier.

According to the present invention, there is still further provided use of the above compound (1) or the salt thereof for a medicine.

According to the present invention, there is yet still further provided a method for the treatment of a respiratory disease, which comprises the administration of the above compound (1) or the salt thereof.

According to the present invention, there are yet still further provided a preparation process of the above compound (1) or the salt thereof, and a novel intermediate useful for preparation thereof.

BEST MODE FOR CARRYING OUT THE INVENTION

In the general formula (1), the linear, branched or cyclic alkyl group represented by $R^1$ is preferably an alkyl group having 1–10 carbon atoms, more preferably an alkyl group having 2–8 carbon atoms, and most preferably an alkyl group having 3–7 carbon atoms. Of such alkyl groups, examples of the linear or branched alkyl group include methyl, ethyl, n-propyl, isopropyl, n-butyl, isobutyl, sec-butyl, tert-butyl, n-pentyl, isopentyl, tert-pentyl, 1-ethylpropyl, n-hexyl, isohexyl, n-heptyl, n-octyl, n-nonyl and n-decyl groups. Of these, n-propyl, isopropyl, n-butyl, isobutyl, sec-butyl, tert-butyl, n-pentyl, tert-pentyl (tert-amyl), 1-ethylpropyl, n-hexyl and n-heptyl groups are particularly preferred. Examples of the cyclic alkyl group include cycloalkyl groups having 3–7 carbon atoms, such as cyclopropyl, cyclobutyl, cyclopentyl, cyclohexyl and cycloheptyl groups. Of these, cyclopropyl, cyclobutyl, cyclopentyl and cyclohexyl groups are particularly preferred.

Examples of the halogen atom represented by $R^2$ include fluorine, chlorine and bromine atoms. Of these, fluorine and chlorine atoms are particularly preferred. The alkyl group is preferably a linear, branched or cycle alkyl group having 1–10 carbon atoms, and more preferably a linear, branched or cycle alkyl group having 1–6 carbon atoms. Examples of such alkyl groups include methyl, ethyl, n-propyl, isopropyl, n-butyl, isobutyl, sec-butyl, tert-butyl, n-pentyl, n-hexyl, cyclopropyl, cyclobutyl, cyclopentyl and cyclohexyl groups. Of these, methyl, ethyl and isopropyl groups are particularly preferred. Examples of the substituted alkyl group include alkoxyalkyl groups, aralkyloxyalkyl groups, aryloxyalkyl groups, aminoalkyl groups which may be substituted (for example, aminoalkyl groups, mono- or di-alkylaminoalkyl groups, cycloalkylaminoalkyl groups, and alkyl groups substituted by a four- to seven-membered cyclic amino group which may additionally have an oxygen or nitrogen atom as a heteroatom making up the ring), and hydroxyalkyl groups. Specific examples thereof include methoxymethyl, ethoxymethyl, dinitrobenzyloxymethyl, benzyloxymethyl, phenoxymethyl, aminomethyl, methylaminomethyl, dimethylaminomethyl, morpholinomethyl, piperazinomethyl, 4-methylpiperazinomethyl and hydroxymethyl groups. Examples of the amino group which may be substituted include an amino group, mono- or di-alkylamino groups, cycloalkylamino groups, cyclic amino groups (for example, four- to seven-membered cyclic amino groups which may additionally have an oxygen or nitrogen atom as a heteroatom making up the ring), alkylsulfonylamino groups which may be substituted by halogen atoms, arylsulfonylamino groups, alkylcarbonylamino groups, arylcarbonylamino groups, a ureido group which may be substituted, a thioureido group which may be substituted, and a hydrazino group which may be substituted. The halogen atoms as substituents include fluorine, chlorine, bromine and iodine atoms. Examples of the substituents on the ureido, thioureido and hydrazino groups include the same linear, branched or cyclic alkyl groups as the examples of the alkyl group represented by $R^1$. Specific examples of the amino group which may be substituted include amino, methylamino, ethylamino, dimethylamino, diethylamino, cyclopropylamino, cyclobutylamino, pyrrolidino, piperidino, morpholino, piperazino, 4-methylpiperazino, methanesulfonylamino, trifluoromethanesulfonylamino, benzenesulfonylamino, acetylamino, benzoylamino, ureido, methylureido, thioureido, methylthioureido, hydrazino and methylhydrazino groups. The alkoxycarbonyl group is preferably an alkoxycarbonyl group having 2–11 carbon atoms in total, and more preferably an alkoxycarbonyl group having 2–7 carbon atoms in total. Examples of the alkoxycarbonyl group include methoxycarbonyl, ethoxycarbonyl and isopropyloxycarbonyl groups. The alkylcarbamoyl group is preferably an alkylcarbamoyl group having 2–11 carbon atoms in total, and more preferably an alkylcarbamoyl group having 2–7 carbon atoms in total. Examples of the alkylcarbamoyl group include methylcarbamoyl, ethylcarbamoyl, isopropylcarbamoyl, dimethylcarbamoyl and diethylcarbamoyl groups.

As the heterocyclic group represented by $R^3$, is particularly preferred a nitrogen-containing heterocyclic group, for example, a tetrazolyl group. The alkylsulfonylamino group which may be substituted by halogen includes alkylsulfonylamino groups having 1–10 carbon atoms, which may be substituted by halogen, with alkylsulfonylamino groups having 1–6 carbon atoms, which may be substituted by 1–3 halogen atoms, being more preferred. Examples of the alkylsulfonylamino group which may be substituted by halogen include methanesulfonylamino, ethanesulfonylamino, propanesulfonylamino, chloroethanesulfonylamino and trifluoromethanesulfonylamino groups.

As the alkyl group represented by $R^4$, is preferred a linear or branched alkyl group having 1–10 carbon atoms, with a linear or branched alkyl group having 1–6 carbon atoms being more preferred. Specific examples of this alkyl group include the same alkyl groups as the examples of the alkyl group represented by $R^2$. As the halogenoalkyl group represented by $R^4$, is preferred a linear or branched halogenoalkyl group having 1–10 carbon atoms, with a linear or branched halogenoalkyl group having 1–6 carbon atoms being more preferred. Specific examples of the halogenoalkyl group include chloromethyl, chloroethyl and trifluoromethyl groups. The alkoxycarbonyl group represented by $R^4$ is preferably an alkoxycarbonyl group having 2–11 carbon atoms in total, and more preferably an alkoxycarbonyl group having 2–7 carbon atoms in total. Specific examples of the alkoxycarbonyl group include the same alkoxycarbonyl groups as the examples of the alkoxycarbonyl group represented by $R^2$.

As the alkyl group represented by $R^5$, is preferred a linear or branched alkyl group having 1–10 carbon atoms, with a linear or branched alkyl group having 1–6 carbon atoms being more preferred. Specific examples of this alkyl group include the same alkyl groups as the examples of the alkyl group represented by $R^2$. As the halogenoalkyl group represented by $R^5$, is preferred a linear or branched halogenoalkyl group having 1–10 carbon atoms, with a linear or branched halogenoalkyl group having 1–6 carbon atoms being more preferred. Specific examples of the halogenoalkyl group include the same halogenoalkyl groups as the examples of the halogenoalkyl group represented by $R^4$. The heterocycle-amino group represented by $R^5$ is preferably a nitrogen-containing heterocycle-amino group, and for example, a tetrazolylamino group is particularly preferred.

Of the groups represented by $R^3$, nitro, amino, acetamino, trifluoroacetamino, methanesulfonylamino, trifluoromethanesulfonylamino, ethyloxalylamino, oxalylamino, tetrazolyl, tetrazolylcarbamoyl, carbamoyl, carboxyl, ethoxycarbonyl and trifluoroacetyl groups are particularly preferred. Of these, the nitro group is more particularly preferred.

As specific examples of the compound (1), may be mentioned 8-tert-butyl-6,7-dihydro-5-methyl-3-nitro-8H-pyrrolo[3,2-e]pyrazolo[1,5-a]pyrimidine (Compound 1), 8-tert-amyl-6,7-dihydro-5-methyl-3-nitro-8H-pyrrolo[3,2-e]-pyrazolo[1,5-a]pyrimidine (Compound 2), 8-cyclopentyl-6,7-dihydro-5-methyl-3-nitro-8H-pyrrolo[3,2-e]pyrazolo[1,5-a]-pyrimidine (Compound 3), 8-cyclohexyl-6,7-dihydro-5-methyl-3-nitro-8H-pyrrolo[3,2-e]pyrazolo[1,5-a]pyrimidine (Compound 4), 8-sec-butyl-6,7-dihydro-5-methyl-3-nitro-8H-pyrrolo[3,2-e]pyrazolo[1,5-a]pyrimidine (Compound 5), 3-amino-8-cyclopentyl-6,7-dihydro-5-methyl-8H-pyrrolo[3,2-e]-pyrazolo[1,5-a]pyrimidine (Compound 6), 3-acetylamino-8-cyclopentyl-6,7-dihydro-5-methyl-8H-pyrrolo[3,2-e]-pyrazolo[1,5-a]pyrimidine (Compound 7), 8-cyclopentyl-6,7-dihydro-5-methyl-3-trifluoromethanesulfonylamino-8H-pyrrolo[3,2-e]pyrazolo[1,5-a]pyrimidine (Compound 8), 8-cyclopentyl-6,7-dihydro-5-methyl-3-trifluoroacetylamino-8H-pyrrolo[3,2-e]pyrazolo[1,5-a]pyrimidine (Compound 9), 8-cyclopentyl-6,7-dihydro-3-methanesulfonylamino-5-methyl-8H-pyrrolo[3,2-e]pyrazolo[1,5-a]pyrimidine (Compound 10), N-(8-cyclopentyl-6,7-dihydro-5-methyl-8H-pyrrolo[3,2-e]-pyrazolo[1,5-a]pyrimidin-3-yl)oxamic acid (Compound 11), ethyl N-(8-cyclopentyl-6,7-dihydro-5-methyl-8H-pyrrolo-[3,2-e]pyrazolo[1,5-a]pyrimidin-3-yl)aminoglyoxylate (Compound 12), 8-tert-butyl-6,7-dihydro-5-methyl-8H-pyrrolo[3,2-e]pyrazolo[1,5-a]pyrimidine-3-N-(1H-tetrazol-5-yl)carboxamide (Compound 13), 8-tert-amyl-6,7-dihydro-5-methyl-8H-pyrrolo-[3,2-e]pyrazolo[1,5-a]pyrimidine-3-

N-(1H-tetrazol-5-yl)carboxamide (Compound 14), 8-cyclopentyl-6,7-dihydro-5-methyl-3-(1H-tetrazol-5-yl)-8H-pyrrolo[3,2-e]-pyrazolo[1,5-a]pyrimidine (Compound 15), 8-tert-butyl-6,7-dihydro-5-methyl-3-(1H-tetrazol-5-yl)-8H-pyrrolo[3,2-e]-pyrazolo[1,5-a]pyrimidine (Compound 16), 8-tert-amyl-6,7-dihydro-5-methyl-3-(1H-tetrazol-5-yl)-8H-pyrrolo[3,2-e]-pyrazolo[1,5-a]pyrimidine (Compound 17), 8-cyclopentyl-6,7-dihydro-5-methyl-8H-pyrrolo[3,2-e]pyrazolo[1,5-a]-pyrimidine-3-carboxamide (Compound 18), 5-amino-8-cyclopentyl-6,7-dihydro-3-nitro-8H-pyrrolo[3,2-e]-pyrazolo[1,5-a]pyrimidine (Compound 19), 5-amino-8-sec-butyl-6,7-dihydro-3-nitro-8H-pyrrolo[3,2-e]pyrazolo[1,5-a]-pyrimidine (Compound 20), ethyl 8-cyclopentyl-6,7-dihydro-3-nitro-8H-pyrrolo[3,2-e]pyrazolo[1,5-a]pyrimidine-5-carboxylate (Compound 21), ethyl 8-sec-butyl-6,7-dihydro-3-nitro-8H-pyrrolo[3,2-e]pyrazolo[1,5-a]pyrimidine-5-carboxylate (Compound 22), 8-cyclopentyl-6,7-dihydro-3-nitro-8H-pyrrolo[3,2-e]pyrazolo[1,5-a]pyrimidine-5-carboxylic acid (Compound 23), 8-sec-butyl-6,7-dihydro-3-nitro-8H-pyrrolo[3,2-e]pyrazolo[1,5-a]pyrimidine-5-carboxylic acid (Compound 24), 8-tert-butyl-6,7-dihydro-5-methyl-3-trifluoroacetyl-8H-pyrrolo[3,2-e]pyrazolo[1,5-a]-pyrimidine (Compound 25), 8-tert-amyl-6,7-dihydro-5-methyl-3-trifluoroacetyl-8H-pyrrolo[3,2-e]pyrazolo[1,5-a]-pyrimidine (Compound 26), 8-cyclopentyl-6,7-dihydro-5-methyl-3-trifluoroacetyl-8H-pyrrolo[3,2-e]pyrazolo[1,5-a]-pyrimidine (Compound 27), 8-cyclohexyl-6,7-dihydro-5-methyl-3-trifluoroacetyl-8H-pyrrolo[3,2-e]pyrazolo[1,5-a]-pyrimidine (Compound 28), 8-sec-butyl-6,7-dihydro-5-methyl-3-trifluoroacetyl-8H-pyrrolo[3,2-e]pyrazolo[1,5-a]-pyrimidine (Compound 29), 8-cyclopentyl-6,7-dihydro-3-ethoxycarbonyl-5-methyl-8H-pyrrolo[3,2-e]pyrazolo[1,5-a]-pyrimidine (Compound 30), 8-tert-butyl-6,7-dihydro-3-ethoxycarbonyl-5-methyl-8H-pyrrolo[3,2-e]pyrazolo[1,5-a]-pyrimidine (Compound 31), 8-tert-amyl-6,7-dihydro-3-ethoxycarbonyl-5-methyl-8H-pyrrolo[3,2-e]pyrazolo[1,5-a]-pyrimidine (Compound 32), 3-carboxy-8-cyclopentyl-6,7-dihydro-5-methyl-8H-pyrrolo[3,2-e]pyrazolo[1,5-a]pyrimidine (Compound 33), 8-tert-butyl-3-carboxy-6,7-dihydro-5-8H-pyrrolo[3,2-e]pyrazolo[1,5-a]pyrimidine (Compound 34), 8-tert-amyl-3-carboxy-6,7-dihydro-5-methyl-8H-pyrrolo-[3,2-e]pyrazolo[1,5-a]pyrimidine (Compound 35), 8-cyclo-pentyl-6,7-dihydro-5-methyl-8H-pyrrolo[3,2-e]pyrazolo-[1,5-a]pyrimidine-3-N-(1H-tetrazol-5-yl)carboxamide (Compound 36), 8-tert-butyl-6,7-dihydro-3-nitro-8H-pyrrolo[3,2-e]pyrazolo[1,5-a]pyrimidine (Compound 37), 8-cyclopentyl-6,7-dihydro-3-nitro-8H-pyrrolo[3,2-e]pyrazolo-[1,5-a]pyrimidine (Compound 38), 8-sec-butyl-6,7-dihydro-3-nitro-8H-pyrrolo[3,2-e]pyrazolo[1,5-a]pyrimidine (Compound 39), 8-tert-butyl-5-chloro-6,7-dihydro-3-nitro-8H-pyrrolo-[3,2-e]pyrazolo[1,5-a]pyrimidine (Compound 40), 5-chloro-8-cyclopentyl-6,7-dihydro-3-nitro-8H-pyrrolo[3,2-e]pyrazolo-[1,5-a]pyrimidine (Compound 41), 8-sec-butyl-5-chloro-6,7-dihydro-3-nitro-8H-pyrrolo[3,2-e]pyrazolo[1,5-a]pyrimidine (Compound 42), 8-sec-butyl-6,7-dihydro-5-methoxymethyl-3-nitro-8H-pyrrolo[3,2-e]pyrazolo[1,5-a]pyrimidine (Compound 43), 8-sec-butyl-6,7-dihydro-5-ethoxymethyl-3-nitro-8H-pyrrolo[3,2-e]pyrazolo[1,5-a]pyrimidine (Compound 44), 5-benzyloxymethyl-8-sec-butyl-6,7-dihydro-3-nitro-8H-pyrrolo-[3,2-e]pyrazolo[1,5-a]pyrimidine (Compound 45), 8-sec-butyl-6,7-dihydro-3-nitro-5-phenoxymethyl-8H-pyrrolo-[3,2-e]pyrazolo[1,5-a]pyrimidine (Compound 46), 5-amino-methyl-8-sec-butyl-6,7-dihydro-3-nitro-8H-pyrrolo[3,2-e]pyrazolo[1,5-a]pyrimidine (Compound 47), 8-sec-butyl-6,7-dihydro-5-methylaminomethyl-3-nitro-8H-pyrrolo[3,2-e]-pyrazolo[1,5-a]pyrimidine (Compound 48), 8-sec-butyl-6,7-dihydro-5-dimethylaminomethyl-3-nitro-8H-pyrrolo[3,2-e]-pyrazolo[1,5-a]pyrimidine (Compound 49), 8-sec-butyl-6,7-dihydro-5-morpholinomethyl-3-nitro-8H-pyrrolo[3,2-e]-pyrazolo[1,5-a]pyrimidine (Compound 50), 8-sec-butyl-6,7-dihydro-3-nitro-5-piperazinomethyl-8H-pyrrolo[3,2-e]-pyrazolo[1,5-a]pyrimidine (Compound 51), 8-sec-butyl-6,7-dihydro-5-(4-methylpiperazino)methyl-3-nitro-8H-pyrrolo[3,2-e]pyrazolo[1,5-a]pyrimidine (Compound 52), 8-sec-butyl-6,7-dihydro-5-hydroxymethyl-3-nitro-8H-pyrrolo-[3,2-e]pyrazolo[1,5-a]pyrimidine (Compound 53), 8-sec-butyl-6,7-dihydro-5-methylamino-3-nitro-8H-pyrrolo[3,2-e]-pyrazolo[1,5-a]pyrimidine (Compound 54), 8-sec-butyl-6,7-dihydro-5-ethylamino-3-nitro-8H-pyrrolo[3,2-e]pyrazolo-[1,5-a]pyrimidine (Compound 55), 8-sec-butyl-6,7-dihydro-5-dimethylamino-3-nitro-8H-pyrrolo[3,2-e]pyrazolo[1,5-a]-pyrimidine (Compound 56), 8-sec-butyl-5-diethylamino-6,7-dihydro-3-nitro-8H-pyrrolo[3,2-e]pyrazolo[1,5-a]pyrimidine (Compound 57), 8-sec-butyl-5-cyclopropylamino-6,7-dihydro-3-nitro-8H-pyrrolo[3,2-e]pyrazolo[1,5-a]pyrimidine (Compound 58), 8-sec-butyl-5-cyclobutylamino-6,7-dihydro-3-nitro-8H-pyrrolo[3,2-e]pyrazolo[1,5-a]pyrimidine (Compound 59), 8-sec-butyl-6,7-dihydro-3-nitro-5-pyrrolidino-8H-pyrrolo[3,2-e]pyrazolo[1,5-a]pyrimidine (Compound 60), 8-sec-butyl-6,7-dihydro-3-nitro-5-piperidino-8H-pyrrolo-[3,2-e]pyrazolo[1,5-a]pyrimidine (Compound 61), 8-sec-butyl-6,7-dihydro-5-morpholino-3-nitro-8H-pyrrolo[3,2-e]-pyrazolo[5-a]pyrimidine (Compound 62), 8-sec-butyl-6,7-dihydro-3-nitro-5-piperazino-8H-pyrrolo[3,2-e]pyrazolo-[1,5-a]pyrimidine (Compound 63), 8-sec-butyl-6,7-dihydro-5-methanesulfonylamino-3-nitro-8H-pyrrolo[3,2-e]pyrazolo-[1,5-a]pyrimidine (Compound 64), 8-sec-butyl-6,7-dihydro-3-nitro-5-trifluoromethanesulfonylamino-8H-pyrrolo[3,2-e]-pyrazolo[1,5-a]pyrimidine (Compound 65), 5-benzenesulfonyl-amino-8-sec-butyl-6,7-dihydro-3-nitro-8H-pyrrolo[3,2-e]-pyrazolo[1,5-a]pyrimidine (Compound 66), 5-acetylamino-8-sec-butyl-6,7-dihydro-3-nitro-8H-pyrrolo[3,2-e]pyrazolo-[1,5-a]pyrimidine (Compound 67), 5-benzoylamino-8-sec-butyl-6,7-dihydro-3-nitro-8H-pyrrolo[3,2-e]pyrazolo[1,5-a]-pyrimidine (Compound 68), 8-sec-butyl-6,7-dihydro-3-nitro-5-ureido-8H-pyrrolo[3,2-e]pyrazolo[1,5-a]pyrimidine (Compound 69), 8-sec-butyl-6,7-dihydro-5-methylureido-3-nitro-8H-pyrrolo[3,2-e]pyrazolo[1,5-a]pyrimidine (Compound 70), 8-sec-butyl-6,7-dihydro-3-nitro-5-thioureido-8H-pyrrolo[3,2-e]pyrazolo[1,5-a]pyrimidine (Compound 71), 8-sec-butyl-6,7-dihydro-5-methylthioureido-3-nitro-8H-pyrrolo[3,2-e]pyrazolo[1,5-a]pyrimidine (Compound 72), 8-sec-butyl-6,7-dihydro-5-hydrazino-3-nitro-8H-pyrrolo-[3,2-e]pyrazolo[1,5-a]pyrimidine (Compound 73), 8-sec-butyl-6,7-dihydro-5-methylhydrazino-3-nitro-8H-pyrrolo-[3,2-e]pyrazolo[1,5-a]pyrimidine (Compound 74), 8-sec-butyl-5-carbamoyl-6,7-dihydro-3-nitro-8H-pyrrolo[3,2-e]-pyrazolo[1,5-a]pyrimidine (Compound 75), ethyl 8-cyclopropyl-6,7-dihydro-3-nitro-8H-pyrrolo[3,2-e]pyrazolo-[1,5-a]pyrimidine-5-carboxylate (Compound 76), ethyl 8-cyclobutyl-6,7-dihydro-3-nitro-8H-pyrrolo[3,2-e]pyrazolo-[1,5-a]pyrimidine-5-carboxylate (Compound 77), ethyl 6,7-dihydro-8-isopropyl-3-nitro-8H-pyrrolo[3,2-e]pyrazolo-[1,5-a]pyrimidine-5-carboxylate (Compound 78), ethyl 6,7-dihydro-8-(1-ethylpropyl)-3-nitro-8H-pyrrolo[3,2-e]-pyrazolo[1,5-a]pyrimidine-5-carboxylate (Compound 79), 8-cyclopropyl-6,7-dihydro-3-nitro-8H-pyrrolo[3,2-e]pyrazolo-[1,5-a]pyrimidine-5-carboxylic acid (Compound 80), 8-cyclobutyl-6,7-dihydro-3-nitro-8H-pyrrolo[3,2-e]pyrazolo[1,5-a]-pyrimidine-5-carboxylic acid (Compound 81), 6,7-dihydro-8-isopropyl-3-nitro-8H-pyrrolo[3,2-e]pyrazolo[1,5-a]-pyrimidine-5-carboxylic acid (Compound 82), 6,7-dihydro-8-(1-ethylpropyl)-3-nitro-8H-pyrrolo[3,2-e]pyrazolo[1,5-a]-pyrimidine-5-carboxylic acid (Compound 83), 5-amino-8-cyclopropyl-6,7-dihydro-3-nitro-8H-pyrrolo[3,2-e]pyrazolo-[1,5-a]pyrimidine (Compound 84), 5-amino-8-cyclobutyl-6,7-dihydro-3-nitro-8H-pyrrolo[3,2-e]pyrazolo[1,5-a]pyrimidine (Compound 85), 5-amino-6,7-dihydro-8-isopropyl-3-nitro-8H-pyrrolo[3,2-e]pyrazolo[1,5-a]pyrimidine (Compound 86), 5-amino-6,7-dihydro-8-(1-ethylpropyl)-3-nitro-8H-pyrrolo-[3,2-e]pyrazolo[1,5-a]pyrimidine (Compound 87) and 8-sec-butyl-6,7-dihydro-5-(2',4'-dinitrobenzyloxymethyl)-3-nitro-8H-pyrrolo[3,2-e]pyrazolo[1,5-a]pyrimidine (Compound 88).

No particular limitation is imposed on the salts usable in the present invention so far as they are physiologically acceptable salts. However, preferable examples of the salts include mineral acid salts such as hydrochlorides, sulfates, nitrates and phosphates; organic acid salts such as citrates, oxalates, fumarates, maleates, formates, acetates, methanesulfonates, benzenesulfonates and p-toluenesulfonates; and carbonates.

The compounds (1) according to the present invention also include solvates thereof such as hydrates.

The compounds (1) according to the present invention can be prepared in accordance with, for example, the following reaction scheme A:

[Reaction scheme A]

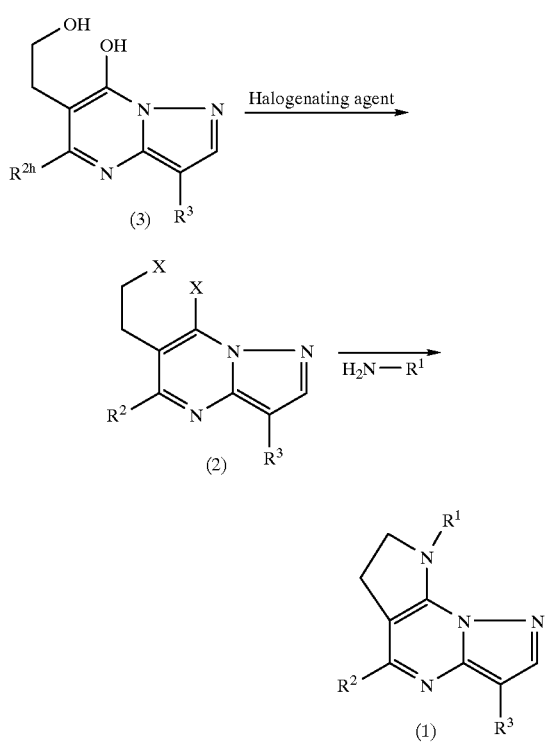

wherein $R^{2h}$ represents a group represnted by $R^2$ except a halogen atom or a hydroxyl group, $R^1$, $R^2$ and $R^3$ have the same meanings as defined abouve, and X represents a hologen atom.

More specifically, a compound (3), in which substituents ($R^{2h}$, $R^3$) have been introduced in advance, or a tautomer thereof is allowed to react with a halogenating agent such as phosphoryl chloride to prepare a dihalogenated product (2). The dihalogenated product is then allowed to react with an amine ($H_2N$—$R^1$) to cyclize it, whereby the compound (1) can be formed. Further, the groups $R^2$ and $R^3$ in the general formula (1) may be changed to various substituents in accordance with a method known per se in the art. Besides, the compound (3) may be converted into the compound (2), the substituents $R^2$ and $R^3$ on the compound (2) may be then changed to other substituents, and the compound (1) may be then prepared.

Here, the tautomer of the compound (3) includes that having the following structure:

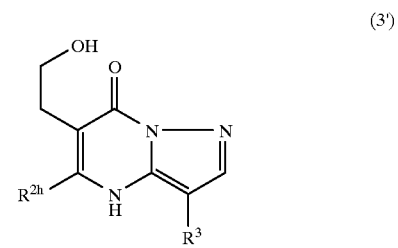

wherein $R^{2h}$ and $R^3$ have the same meanings as defined above.

The compound (3) used herein can be prepared in accordance with the following process (1) or (2):

Process (1):

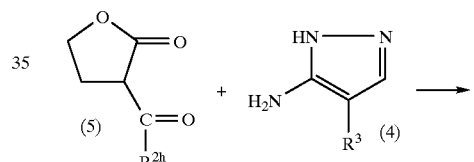

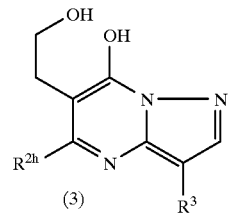

wherein $R^{2h}$ and $R^3$ have the same meanings as defined above.

More specifically, an aminopyrazole derivative (4) and a carbonyllactone derivative (5) are condensed using a Lewis acid or the like as a catalyst, and a formed product is cyclized by the treatment with an alkali as needed, whereby the compound (3) can be obtained.

Process (2):

A compound (3-1) in which $R^{2h}$ in the compound (3) is a hydroxyl group can be prepared in accordance with the following reaction scheme:

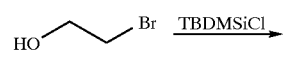

-continued

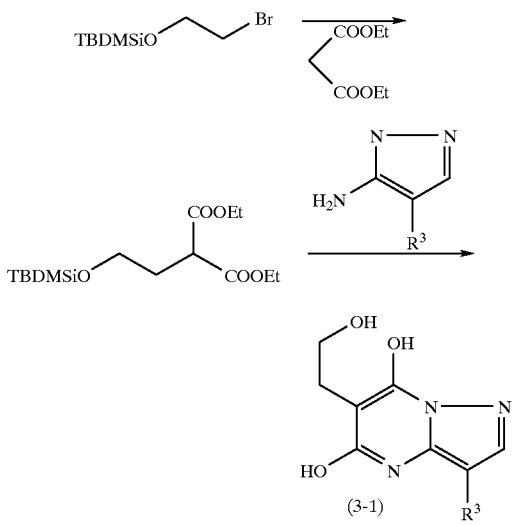

wherein $R^3$ has the same meaning as defined above, and TBDMSi represents a tert-butyldimethylsilyl group.

More specifically, bromoethanol is tert-butyldimethylsilylated with tert-butyldimethylsilyl chloride, the silylated product is then condensed with diethyl malonate in the presence of an alkali such as sodium ethoxide, and the condensate is then allowed to react with aminopyrazole, whereby the compound (3-1) in which $R^{2h}$ is a hydroxyl group can be obtained.

The compound (3) is allowed to react with a halogenating reagent, whereby the dihalogenated product (2) can be obtained. No particular limitation is imposed on the halogenating reagent used herein. However, an example thereof includes phosphorus oxychloride. The halogenating reagent is generally used in a proportion of 1.0–10.0 mol, preferably 2.0–5.0 mol based on the compound (3). No particular limitation is imposed on a solvent used in the reaction so far as it is a nonaqueous solvent. Specific examples thereof include N,N-dimethylformamide, chloroform and dichloromethane. When the halogenating reagent is liquid, the reaction may be conducted without using any solvent. In order to facilitate the progress of the reaction, a basic catalyst may be used. The reaction may also be performed under a nitrogen gas atmosphere. The reaction temperature varies according to the physical properties of the solvent, halogenating reagent and catalyst used. However, the reaction is preferably conducted while heating under reflux. The treatment and purification after the reaction may be performed in accordance with the ordinary methods. However, it is necessary to take care to prevent $R^2$ and $R^3$ from being decomposed in some cases.

Incidentally, when the compound (3-1) in which $R^{2h}$ is a hydroxyl group is allowed to react with a phosphorus oxyhalide, a compound (2) in which $R^2$ is a halogen atom can be obtained.

$R^2$ and/or $R^3$ may also be changed to various substituents.

The amine ($H_2N$—$R^1$) is generally used in a proportion of 1.0–10.0 mol, preferably 1.0–2.5 mol based on the dihalogenated product (2). As the catalyst for the reaction, is used a tertiary organic amine or an inorganic base. Specific examples thereof include triethylamine, N,N-diisopropylethylamine, anhydrous potassium carbonate and anhydrous sodium carbonate. These catalysts are generally used in a proportion of 0.5–30.0 mol, preferably 2.0–5.0 mol based on the compound represented by the general formula (2). $R^1$—$NH_2$, which is a raw amine, may be used in great excess to conduct the reaction without using the catalyst. No particular limitation is imposed on the solvent used in the reaction so far as it is a nonaqueous solvent which can solve the two raw materials therein. Specific examples thereof include N,N-dimethylformamide, chloroform and dichloromethane. Specifically, the amount of the solvent used may be 5 to 100 times as much as the amount of the raw compounds. These solvents may be used either singly or in any combination thereof. The solvent may be selected according to the physical properties of the raw compounds and catalyst used. The reaction temperature in the preparation process of the present invention may be any temperature of from room temperature to a temperature near the boiling point of the solvent. However, room temperature is preferred. The reaction time required for the preparation process of the present invention varies according to various conditions, and is 30 minutes to 30 days.

A compound (1-N) in which $R^3$ in the general formula (1) is a nitro group can also be prepared in accordance with the following reaction scheme B:

[Reaction scheme B]

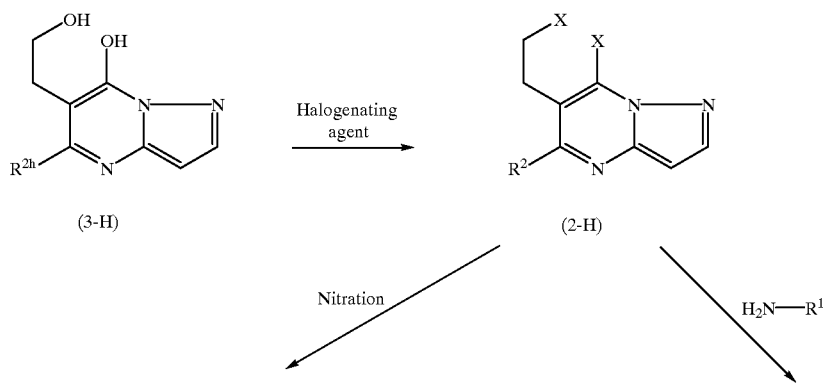

-continued

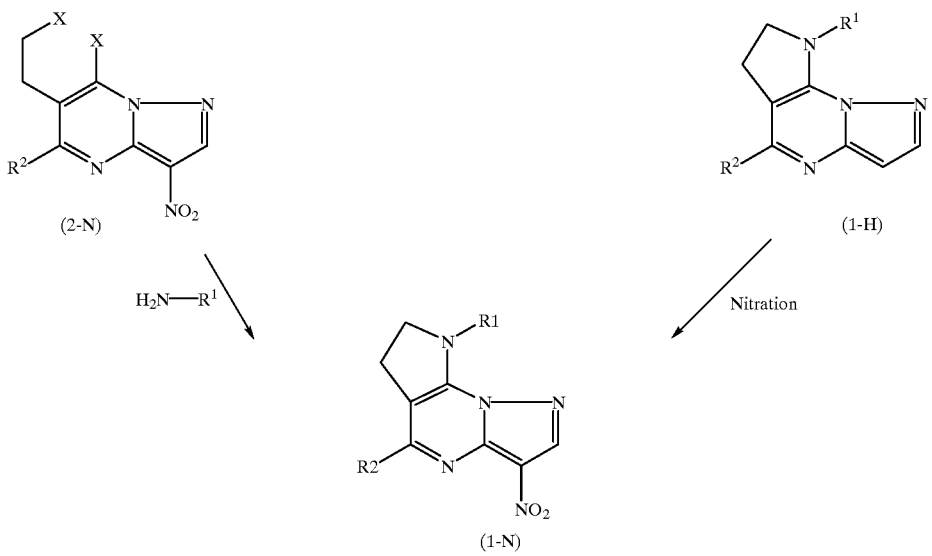

wherein $R^1$, $R^{2h}$ and $R^2$ have the same meanings as defined above, and X represents a halogen atom.

More specifically, a compound (3-H) or a tautomer thereof is allowed to react with a halogenating agent to prepare a dihalogenated product (2-H). The dihalogenated product is then allowed to react with an amine ($H_2N—R^1$) to cyclize it, and the thus-obtained compound (1-H) is nitrated, whereby the compound (1-N) can be prepared.

Besides, the dihalogenated product (2-H) is nitrated into a compound (2-N), and the thus-obtained compound (2-N) is allowed to react with an amine ($H_2N—R^1$), whereby the compound (1-N) may be prepared.

Here, the compound (3-H) can be obtained in the same manner as in the process for the preparation of the compound (3) except that 3-aminopyrazole is used. The halogenation of the compound (3-H) and the reaction of the compound (2-H) or compound (2-N) with the amine are conducted in accordance with their corresponding processes in the reaction scheme A.

The nitration of the compound (1-H) or compound (2-H) is conducted by, for example, the reactione of these compounds with concentrated sulfuric acid and nitric acid.

Further, the compound (1-N) in which $R^2$ in the general formula (1) is a hydrogen atom can also be prepared in accordance with the following reaction scheme C:

[Reaction scheme C]

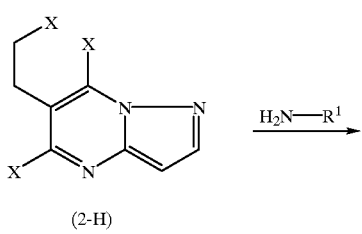

(2-H)

-continued wherein $R^1$ and X have the same meanings as defined above.

More specifically, a compound (2-H) in which $R^2$ is a halogen atom is allowed to react with an amine ($H_2N—R^1$) to prepare a compound (1-H) in which $R^2$ is the halogen atom. The compound (1-H) is further reduced into a compound (1-H') in which $R^2$ is a hydrogen atom, and the compound (1-H') is then nitrated, whereby a compound (1-N) in which $R^2$ is the hydrogen atom may also be obtained.

As described above, the compound (3-H), the compound (2-H), the compound (2-N), the compound (1-H) and the compound (1-H') are important as intermediates useful for preparation of the compounds (1) according to the present invention, particularly, the compounds (1-N).

Specific examples of the compounds (1-H) and the compound (1-H') include ethyl 8-cyclopentyl-6,7-dihydro-8H-pyrrolo[3,2-e]pyrazolo[1,5-a]pyrimidine-5-carboxylate, ethyl 8-sec-butyl-6,7-dihydro-8H-pyrrolo[3,2-e]pyrazolo-[1,5-a]pyrimidine-5-carboxylate, ethyl 8-cyclohexyl-6,7-dihydro-8H-pyrrolo[3,2-e]pyrazolo[1,5-a]pyrimidine-5-carboxylate, ethyl 8-tert-butyl-6,7-dihydro-8H-pyrrolo-[3,2-e]pyrazolo[1,5-a]pyrimidine-5-carboxylate, ethyl 8-tert-amyl-6,7-dihydro-8H-pyrrolo[3,2-e]pyrazolo[1,5-a]-pyrimidine-5-carboxylate, methyl 8-cyclopentyl-6,7-dihydro-8H-pyrrolo[3,2-e]pyrazolo[1,5-a]pyrimidine-5-carboxylate, methyl 8-sec-butyl-6,7-dihydro-8H-pyrrolo[3,2-e]pyrazolo-[1,5-a]pyrimidine-5-carboxylate, methyl 8-cyclohexyl-6,7-dihydro-8H-pyrrolo[3,2-e]pyrazolo[1,5-a]pyrimidine-5-carboxylate, methyl 8-tert-butyl-6,7-dihydro-8H-pyrrolo-[3,2-e]pyrazolo[1,5-a]pyrimidine-5-carboxylate, methyl 8-tert-amyl-6,7-dihydro-8H-pyrrolo[3,2-e]pyrazolo[1,5-a]-pyrimidine-5-carboxylate, isopropyl 8-cyclopentyl-6,7-dihydro-8H-pyrrolo[3,2-e]pyrazolo[1,5-a]pyrimidine-5-carboxylate, isopropyl 8-sec-butyl-6,7-dihydro-8H-pyrrolo-[3,2-e]pyrazolo[1,5-a]pyrimidine-5-carboxylate, isopropyl 8-cyclohexyl-6,7-dihydro-8H-pyrrolo[3,2-e]pyrazolo[1,5-a]-pyrimidine-5-carboxylate, isopropyl 8-tert-butyl-6,7-dihydro-8H-pyrrolo[3,2-e]pyrazolo[1,5-a]pyrimidine-5-carboxylate, isopropyl 8-tert-amyl-6,7-dihydro-8H-pyrrolo-[3,2-e]pyrazolo[1,5-a]pyrimidine-5-carboxylate, 5-chloro-8-cyclopentyl-6,7-dihydro-8H-pyrrolo[3,2-e]pyrazolo[1,5-a]-pyrimidine, 8-sec-butyl-5-chloro-6,7-dihydro-8H-pyrrolo-[3,2-e]pyrazolo[1,5-a]pyrimidine, 5-chloro-8-cyclohexyl-6,7-dihydro-8H-pyrrolo[3,2-e]pyrazolo[1,5-a]pyrimidine, 8-tert-butyl-5-chloro-6,7-dihydro-8H-pyrrolo[3,2-e]pyrazolo-[1,5-a]pyrimidine, 8-tert-amyl-5-chloro-6,7-dihydro-8H-pyrrolo[3,2-e]pyrazolo[1,5-a]pyrimidine, 8-cyclopentyl-6,7-dihydro-8H-pyrrolo[3,2-e]pyrazolo[1,5-a]pyrimidine, 8-sec-butyl-6,7-dihydro-8H-pyrrolo[3,2-e]pyrazolo[1,5-a]-pyrimidine, 8-cyclohexyl-6,7-dihydro-8H-pyrrolo[3,2-e]-pyrazolo[1,5-a]pyrimidine, 8-tert-butyl-6,7-dihydro-8H-pyrrolo[3,2-e]pyrazolo[1,5-a]pyrimidine, 8-tert-amyl-6,7-dihydro-8H-pyrrolo[3,2-e]pyrazolo[1,5-a]pyrimidine, ethyl 6,7-dihydro-8-isopropyl-8H-pyrrolo[3,2-e]pyrazolo[1,5-a]-pyrimidine-5-carboxylate, ethyl 8-cyclopropyl-6,7-dihydro-8H-pyrrolo[3,2-e]pyrazolo[1,5-a]pyrimidine-5-carboxylate, ethyl 6,7-dihydro-8-(1-ethylpropyl)-8H-pyrrolo[3,2-e]-pyrazolo[1,5-a]pyrimidine-5-carboxylate, ethyl 8-cyclobutyl-6,7-dihydro-8H-pyrrolo[3,2-e]pyrazolo[1,5-a]-pyrimidine-5-carboxylate, 8-cyclopentyl-6,7-dihydro-5-methoxymethyl-8H-pyrrolo[3,2-e]pyrazolo[1,5-a]pyrimidine, 8-sec-butyl-6,7-dihydro-5-methoxymethyl-8H-pyrrolo[3,2-e]-pyrazolo[1,5-a]pyrimidine, 8-cyclohexyl-6,7-dihydro-5-methoxymethyl-8H-pyrrolo[3,2-e]pyrazolo[1,5-a]pyrimidine, 8-tert-butyl-6,7-dihydro-5-methoxymethyl-8H-pyrrolo[3,2-e]-pyrazolo[1,5-a]pyrimidine, 8-tert-amyl-6,7-dihydro-5-methoxymethyl-8H-pyrrolo[3,2-e]pyrazolo[1,5-a]pyrimidine, 6,7-dihydro-8-isopropyl-5-methoxymethyl-8H-pyrrolo[3,2-e]-pyrazolo[1,5-a]pyrimidine, 8-cyclopropyl-6,7-dihydro-5-methoxymethyl-8H-pyrrolo[3,2-e]pyrazolo[1,5-a] pyrimidine, 6,7-dihydro-8-(1-ethylpropyl)-5-methoxymethyl-8H-pyrrolo-[3,2-e]pyrazolo[1,5-a]pyrimidine, 8-cyclobutyl-6,7-dihydro-5-methoxymethyl-8H-pyrrolo[3,2-e]pyrazolo[1,5-a]pyrimidine, 5-benzyloxymethyl-8-cyclohexyl-6,7-dihydro-8H-pyrrolo-[3,2-e]pyrazolo[1,5-a]pyrimidine, 5-benzyloxymethyl-8-sec-butyl-6,7-dihydro-8H-pyrrolo[3,2-e]pyrazolo[1,5-a]-pyrimidine, 5-benzyloxymethyl-8-cyclohexyl-6,7-dihydro-8H-pyrrolo[3,2-e]pyrazolo[1,5-a]pyrimidine, 5-benzyloxymethyl-8-tert-butyl-6,7-dihydro-8H-pyrrolo[3,2-e]pyrazolo[1,5-a]-pyrimidine, 8-tert-amyl-5-benzyloxymethyl-6,7-dihydro-8H-pyrrolo[3,2-e]pyrazolo[1,5-a]pyrimidine, 5-benzyloxymethyl-6,7-dihydro-8-isopropyl-8H-pyrrolo[3,2-e]pyrazolo[1,5-a]-pyrimidine, 5-benzyloxymethyl-8-cyclopropyl-6,7-dihydro-8H-pyrrolo[3,2-e]pyrazolo[1,5-a]pyrimidine, 5-benzyloxymethyl-6,7-dihydro-8-(1-ethylpropyl)-8H-pyrrolo[3,2-e]-pyrazolo[1,5-a]pyrimidine, 5-benzyloxymethyl-8-cyclobutyl-6,7-dihydro-8H-pyrrolo[3,2-e]pyrazolo[1,5-a]pyrimidine, 8-cyclopentyl-6,7-dihydro-5-phenyloxymethyl-8H-pyrrolo-[3,2-e]pyrazolo[1,5-a]pyrimidine, 8-sec-butyl-6,7-dihydro-5-phenyloxymethyl-8H-pyrrolo[3,2-e]pyrazolo[1,5-a]-pyrimidine, 8-cyclohexyl-6,7-dihydro-5-phenyloxymethyl-8H-pyrrolo[3,2-e]pyrazolo[1,5-a]pyrimidine, 8-tert-butyl-6,7-dihydro-5-phenyloxymethyl-8H-pyrrolo[3,2-e]pyrazolo[1,5-a]-pyrimidine, 8-tert-amyl-6,7-dihydro-5-phenyloxymethyl-8H-pyrrolo[3,2-e]pyrazolo[1,5-a] pyrimidine, 6,7-dihydro-8-isopropyl-5-phenyloxymethyl-8H-pyrrolo[3,2-e]pyrazolo-[1,5-a]pyrimidine, 8-cyclopropyl-6,7-dihydro-5-phenyloxymethyl-8H-pyrrolo[3,2-e]pyrazolo[1,5-a]pyrimidine, 6,7-dihydro-8-(1-ethylpropyl)-5-phenyloxymethyl-8H-pyrrolo-[3,2-e]pyrazolo[1,5-a]pyrimidine, 8-cyclobutyl-6,7-dihydro-5-phenyloxymethyl-8H-pyrrolo[3,2-e]pyrazolo[1,5-a]-pyrimidine, 6,7-dihydro-8-isopropyl-8H-pyrrolo[3,2-e]-pyrazolo[1,5-a]pyrimidine, 8-cyclopropyl-6,7-dihydro-8H-pyrrolo[3,2-e]pyrazolo[1,5-a]pyrimidine, 6,7-dihydro-8-(1-ethylpropyl)-8H-pyrrolo[3,2-e]pyrazolo[1,5-a]pyrimidine, 8-cyclobutyl-6,7-dihydro-8H-pyrrolo[3,2-e]pyrazolo[1,5-a]-pyrimidine, 5-chloro-6,7-dihydro-8-isopropyl-8H-pyrrolo[3,2-e]pyrazolo[1,5-a]pyrimidine, 5-chloro-8-cyclopropyl-6,7-dihydro-8H-pyrrolo[3,2-e]pyrazolo[1,5-a]-pyrimidine, 5-chloro-6,7-dihydro-8-(1-ethylpropyl)-8H-pyrrolo[3,2-e]pyrazolo[1,5-a]pyrimidine and 5-chloro-8-cyclobutyl-6,7-dihydro-8H-pyrrolo[3,2-e]pyrazolo[1,5-a]-pyrimidine.

Pyrazolopyrimidine derivatives including the compounds (2), (2-H), (2-N), (3) and (3-H) and represented by the following general formula (A):

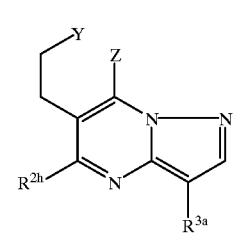

(A)

wherein Y represents a hydroxyl group or a halogen atom, Z represents a hydroxyl group or a halogen atom, $R^{3a}$ represents a hydrogen atom or has the same meaning as in $R^3$ defined above, and $R^{2h}$ has the same meanings as defined above including a halogen atom, with the proviso that $R^{2h}$ is neither a lower alkyl group nor a cycloalkyl group when $R^{3a}$ is a hydrogen atom, $R^{2h}$ is not a hydroxyl group when Y and Z are halogen atoms, or $R^{2h}$ is not a halogen atom when Y and Z are hydroxyl groups, and tautomers and salts thereof are novel compounds important as intermediates useful for preparation of the compounds (1) according to the present invention.

In the general formula (A), Y and Z independently represent a hydroxyl group or a halogen atom such as a chlorine atom, bromine atom or iodine atom. Of the halogen atoms, the chlorine atom is preferred. Specific examples of the compounds (A) include ethyl 6-(2-hydroxyethyl)-pyrazolo[1,5-a]pyrimidin-7(4H)-one-5-carboxylate, methyl 6-(2-hydroxyethyl)pyrazolo[1,5-a]pyrimidin-7(4H)-one-5-carboxylate, n-propyl 6-(2-hydroxyethyl)pyrazolo[1,5-a]-pyrimidin-7(4H)-one-5-carboxylate, isopropyl 6-(2-hydroxyethyl)pyrazolo[1,5-a]-pyrimidin-7(4H)-one-5-carboxylate, tert-butyl 6-(2-hydroxyethyl)pyrazolo[1,5-a]-pyrimidin-7(4H)-one-5-carboxylate, ethyl 7-chloro-6-(2-chloroethyl)pyrazolo[1,5-a]pyrimidine-5-carboxylate, methyl 7-chloro-6-(2-chloroethyl)pyrazolo[1,5-a] pyrimidine-5-carboxylate, n-propyl 7-chloro-6-(2-chloroethyl)-pyrazolo[1,5-a]pyrimidine-5-carboxylate, isopropyl 7-chloro-6-(2-chloroethyl)pyrazolo[1,5-a] pyrimidine-5-carboxylate, tert-butyl 7-chloro-6-(2-chloroethyl)-pyrazolo[1,5-a]pyrimidine-5-carboxylate, 6-(2-chloroethyl)-5,7-dichloropyrazolo[1,5-a]pyrimidine, 5-hydroxy-6-(2-hydroxyethyl) pyrazolo[1,5-a]pyrimidin-7(4H)-one, 6-(2-hydroxyethyl)-5-methoxymethylpyrazolo[1,5-a]pyrimidin-7(4H)-one, 5-benzyloxy-6-(2-hydroxyethyl)pyrazolo[1,5-a]-pyrimidin-7(4H)-one, 6-(2-hydroxyethyl)-5-phenyloxymethyl-pyrazolo[1,5-a]pyrimidin-7(4H)-one, 7-chloro-6-(2-chloroethyl)-5-methoxymethylpyrazolo[1,5-a]pyrimidine, 5-benzyloxymethyl-7-chloro-6-(2-chloroethyl)pyrazolo[1,5-a]-pyrimidine, 7-chloro-6-(2-chloroethyl)-5-phenyloxymethyl-pyrazolo[1,5-a] pyrimidine, 7-chloro-6-(2-chloroethyl)-5-methyl-3-nitropyrazolo[1,5-a]pyrimidine, ethyl 6-(2-hydroxyethyl)-5-methylpyrazolo[1,5-a]pyrimidin-7(4H)-one-3-carboxylate, ethyl 7-chloro-6-(2-chloroethyl)-5-methylpyrazolo[1,5-a]pyrimidine-3-carboxylate, ethyl 7-chloro-6-(2-chloroethyl)-3-nitropyrazolo[1,5-a]pyrimidine-5-carboxylate, 7-bromo-6-(2-bromoethyl)-5-methyl-3-nitropyrazolo[1,5-a]pyrimidine, 7-chloro-6-(2-chloroethyl)-5-ethyl-3-nitropyrazolo[1,5-a]pyrimidine, 7-chloro-6-(2-chloroethyl)-5-n-propyl-3-nitropyrazolo[1,5-a]pyrimidine, 7-chloro-6-(2-chloroethyl)-5-isopropyl-3-nitropyrazolo-[1,5-a] pyrimidine, 7-chloro-6-(2-chloroethyl)-5-cyclopropyl-3-nitropyrazolo[1,5-a]pyrimidine, 5-n-butyl-7-chloro-6-(2-chloroethyl)-3-nitropyrazolo[1,5-a]pyrimidine, 5-t-butyl-7-chloro-6-(2-chloroethyl)-3-nitropyrazolo-[1,5-a]pyrimidine, 7-chloro-6-(2-chloroethyl)-5-cyclopentyl- 3-nitropyrazolo[1,5-a]pyrimidine, ethyl 5-ethyl-6-(2-hydroxyethyl)pyrazolo[1,5-a]pyrimidin-7(4H)-one-3-carboxylate, ethyl 6-(2-hydroxyethyl)-5-n-propylpyrazolo-[1,5-a]pyrimidin-7(4H)-one-3-carboxylate, ethyl 6-(2-hydroxyethyl)-5-isopropylpyrazolo[1,5-a]pyrimidin-7(4H)-one-3-carboxylate, ethyl 6-(2-hydroxyethyl)-5-cyclopropylpyrazolo[1,5-a]pyrimidin-7(4H)-one-3-carboxylate, ethyl 5-n-butyl-6-(2-hydroxyethyl)pyrazolo[1,5-a]pyrimidin-7(4H)-one-3-carboxylate, ethyl 5-t-butyl-6-(2-hydroxyethyl)-pyrazolo[1,5-a]pyrimidin-7(4H)-one-3-carboxylate, ethyl 6-(2-hydroxyethyl)-5-cyclopentylpyrazolo[1,5-a]pyrimidin-7(4H)-one-3-carboxylate, methyl 6-(2-hydroxyethyl)-5-methylpyrazolo[1,5-a]pyrimidin-7(4H)-one-3-carboxylate, n-propyl 6-(2-hydroxyethyl)-5-methylpyrazolo[1,5-a]pyrimidin-7(4H)-one-3-carboxylate, t-butyl 6-(2-hydroxyethyl)-5-methylpyrazolo[1,5-a]pyrimidin-7(4H)-one-3-carboxylate, ethyl 7-bromo-6-(2-bromoethyl)-5-methylpyrazolo[1,5-a]-pyrimidine-3-carboxylate, ethyl 7-chloro-6-(2-chloroethyl)-5-ethylpyrazolo[1,5-a]pyrimidine-3-carboxylate, ethyl 7-chloro-6-(2-chloroethyl)-5-n-propylpyrazolo[1,5-a]-pyrimidine-3-carboxylate, ethyl 7-chloro-6-(2-chloroethyl)-5-isopropylpyrazolo[1,5-a]pyrimidine-3-carboxylate, ethyl 7-chloro-6-(2-chloroethyl)-5-cyclopropylpyrazolo[1,5-a]-pyrimidine-3-carboxylate, ethyl 5-t-butyl-7-chloro-6-(2-chloroethyl) pyrazolo[1,5-a]pyrimidine-3-carboxylate, methyl 7-chloro-6-(2-chloroethyl)-5-methylpyrazolo[1,5-a]-pyrimidine-3-carboxylate, n-propyl 7-chloro-6-(2-chloro-ethyl)- 5-methylpyrazolo[1,5-a]pyrimidine-3-carboxylate, t-butyl 7-chloro-6-(2-chloroethyl)-5-methylpyrazolo[1,5-a]-pyrimidine-3-carboxylate, ethyl 7-bromo-6-(2-bromoethyl)-3-nitropyrazolo[1,5-a] pyrimidine-5-carboxylate, methyl 7-chloro-6-(2-chloroethyl)-3-nitropyrazolo[1,5-a]pyrimidine-5-carboxylate, n-butyl 7-chloro-6-(2-chloroethyl)-3-nitropyrazolo[1,5-a]pyrimidine-5-carboxylate, t-butyl 7-chloro-6-(2-chloroethyl)-3-nitropyrazolo[1,5-a]pyrimidine-5-carboxylate, 6-(2-chloroethyl)-5,7-dichloro-3-nitropyrazolo[1,5-a]pyrimidine and 7-chloro-6-(2-chloroethyl)-5-(2', 4'-dinitrobenzyloxymethyl)-3-nitropyrazolo[1,5-a]-pyrimidine.

Conversion examples of the substituents $R^2$ and $R^3$ will hereinafter be described.

(1) Conversion example (i) of $R^2$:

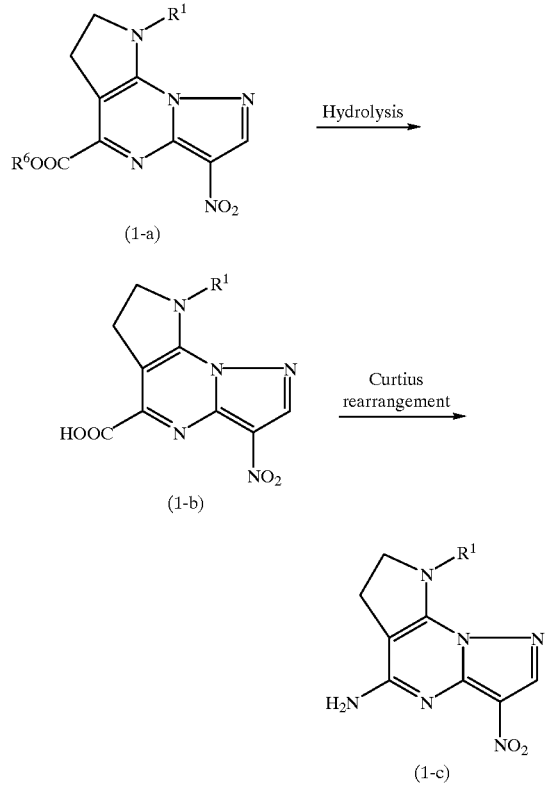

wherein $R^6$ represents an alkyl group, and $R^1$ has the same meaning as described above.

More specifically, a compound (1-a) is hydrolyzed into a compound (1-b), and the resultant compound (1-b) is then subjected to a Curtius rearrangement reaction, whereby a compound (1-c) can be prepared.

Here, the hydrolysis of the compound (1-a) is conducted in the presence of a base, for example, sodium hydroxide. The Curtius rearrangement is conducted by first the conversion of the carboxyl group into a mixed acid anhydride group with a chloroformic ester in the presence of, for example, a basic catalyst, then the reactione of the formed product with sodium azide, and finally heating of the azide formed.

(2) Conversion example (ii) of $R^2$:

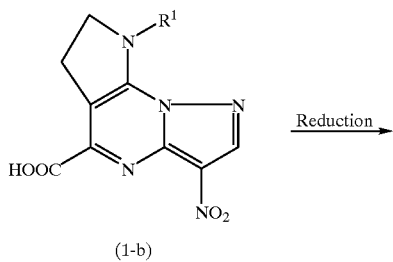

(1-b)

Reduction →

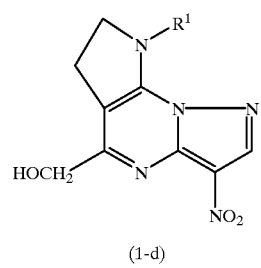

(1-d)

wherein $R^1$ has the same meaning as defined above.

More specifically, the compound (1-b) obtained by the hydrolysis of the compound (1-a) is converted into a mixed acid anhydride with a chloroformic ester in the presence of a basic catalyst, and the acid anhydride is reduced with sodium borohydride, whereby a compound (1-d) in which $R^2$ is a hydroxymethyl group can be obtained.

(3) Conversion example (iii) of $R^2$:

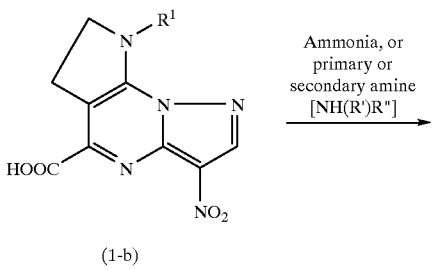

(1-b)

Ammonia, or primary or secondary amine [NH(R')R''] →

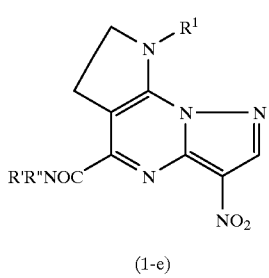

(1-e)

wherein $R^1$ has the same meaning as defined above, and R' and R'' independently represent a hydrogen atom or an alkyl group.

More specifically, the compound (1-b) is converted into a mixed acid anhydride with a chloroformic ester in the presence of a basic catalyst, and the acid anhydride is allowed to react with ammonia, a primary amine or a secondary amine, whereby a compound (1-e) in which $R^2$ is a carbamoyl or alkylcarbamoyl group can be prepared.

(4) Conversion example (iv) of $R^2$:

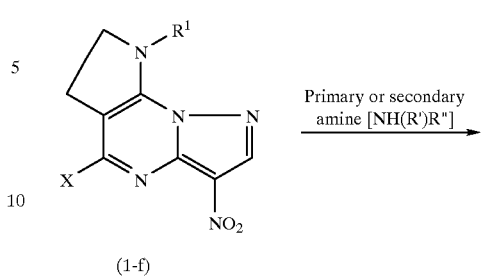

(1-f)

Primary or secondary amine [NH(R')R''] →

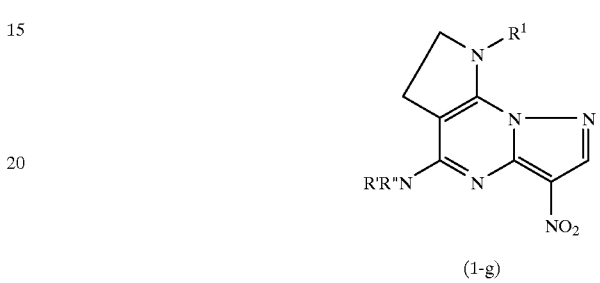

(1-g)

wherein $R^1$ has the same meaning as defined above, X represents a halogen atom, and R' and R'' independently represent a hydrogen atom, or an alkyl or cycloalkyl group, or may form a heterocyclic ring, which may contain an additional heteroatom, together with the adjacent nitrogen atom.

More specifically, a compound (1-f) in which $R^2$ is a halogen atom is allowed to react with a primary or secondary amine, whereby a compound (1-g) in which $R^2$ is an amino group which may be substituted can be obtained.

(5) Conversion example (i) of $R^3$:

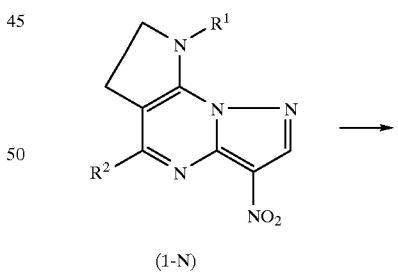

(1-N)

→

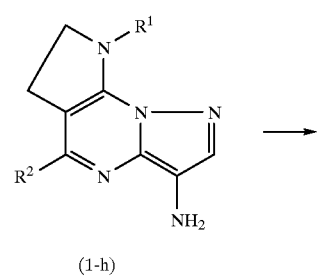

(1-h)

-continued

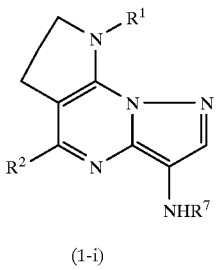

(1-i)

wherein $R^7$ represents an alkylsulfonyl group which may be substituted by halogen, or $R^4CO$— (in which $R^4$ has the same meaning as defined above), and $R^1$ and $R^2$ have the same meanings as defined above.

More specifically, the compound (1-N) is reduced with a reducing agent such as tin chloride into a compound (1-h), and the compound (1-h) is then allowed to react with an alkylsulfonylating agent or acylating agent, whereby a compound (1-i) can be obtained. Examples of the alkylsulfonylating agent or acylating agent include halides and acid anhydrides.

(6) Conversion example (ii) or $R^3$:

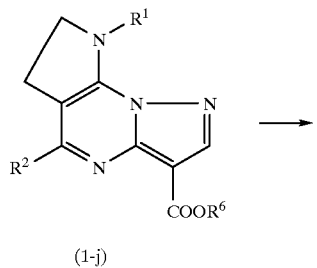

(1-j)

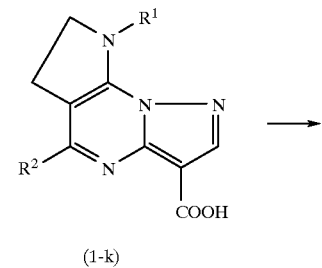

(1-k)

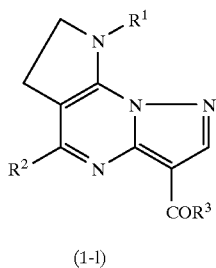

(1-l)

wherein $R^8$ represents an amino group or heterocycle-amino group, and $R^1$, $R^2$ and $R^6$ have the same meanings as defined above.

More specifically, a compound (1-j) is hydrolyzed into a compound (1-k), the hydrolyzate (1-k) is then converted into a mixed acid anhydride or allowed to react with 1,1'-carbonyldiimidazole, and the resultant acid anhydride or the reaction product is then allowed to react with ammonia or a heterocycle-amine, whereby a compound (1-l) can be obtained.

(7) Conversion example (iii) of $R^3$:

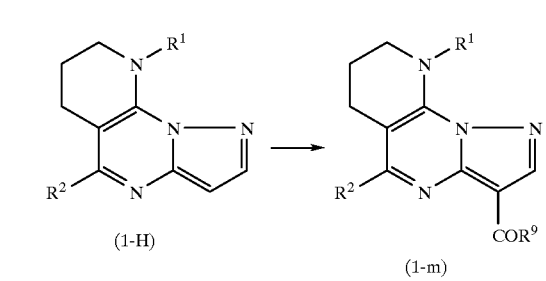

(1-H)          (1-m)

wherein $R^9$ represents an alkyl group or halogenoalkyl group, and $R^1$ and $R^2$ have the same meanings as defined above.

More specifically, the compound (1-H) is allowed to react with an acylating agent such as an acid anhydride, whereby a compound (1-m) can be obtained.

The treatment and purification after the reaction may be conducted by a combination of ordinary methods, for example, quenching with water, extraction with solvent, column chromatography and recrystallization.

The compounds (1) can be converted to salts in accordance with a method known per se in the art, for example, their mixing with an acid in a polar or nonpolar solvent.

The thus-obtained compounds (1) or the salts thereof can be purified in accordance with a method known per se in the art, such as column chromatography or recrystallization.

The compounds (1) according to the present invention or the salts thereof have excellent tracheobronchodilative effect and inhibitory effect on airway constriction and act only weakly on circulatory organs, and are hence useful as prophylactic and therapeutic medicines for respiratory diseases such as asthma, chronic obstructive pulmonary disease, bronchitis and pneumonia.

The compounds (1) or the salts thereof may be used as medicines by themselves, but may also be formulated into various preparation forms (compositions) generally used in medicines. Such preparation forms include inhalants, injections, oral preparations, intrarectal preparations and the like.

The medicinal compositions of these preparation forms according to the present invention may contain, in addition to the compound (1) or the salt thereof, pharmaceutically acceptable carriers, for example, optional ingredients routinely used for preparation of drugs. Examples of such ingredients include excipients, binders, coating agents, lubricants, sugar-coatings, disintegrators, extending agents, taste and smell corrigents, emulsifying, solubilizing or dispersing agents, stabilizers, pH adjusters, isotonicity agents and the like. Besides the above individual ingredients, the medicinal compositions according to the present invention may contain known medicines routinely used in treatment and prevention of respiratory diseases, for example, theophylline. The medicinal compositions according to the present invention can be prepared by using these ingredients in accordance with a method known per se in the art.

The preferable dose of the medicine according to the present invention varies according to the condition, sex, age and weight of a patient to be administered, the kind of a disease to be treated or prevented, and the like. However, it is preferably administered in a dose of generally 1 to 1,000 mg per day for an adult in terms of the compound (1) or the salt thereof. The medicine is preferably administered at once or in several portions a day.

EXAMPLES

The present invention will hereinafter be described in more detail by the following Examples. However, the present invention is not limited to these examples.

EXAMPLE 1

Preparation of 3-{[1-(tetrahydro-2-oxo-3-furyl)-ethylidene]amino}pyrazole:

In 12 ml of anhydrous ethanol were added 0.83 g (10.00 mmol) of 3-aminopyrazole and 1.92 g (15.00 mmol) of 2-acetyl-γ-butyrolactone. While stirring at room temperature, 0.1 ml of a boron trifluoride methanol complex were added to the resultant solution, and the mixture was then stirred for 4 hours under the same conditions. Solids deposited were collected by filtration, washed with ethanol and air-dried to obtain 1.34 g (yield: 69.4%) of the intended product.

$^1$H-NMR (DMSO-d$_6$, ppm): 2.45(3H,s), 2.86(2H,t,J=7.8Hz), 4.27(2H,t,J=7.8Hz), 6.07(1H,d,J=2.2Hz), 6.67(1H,d,J=2.2Hz), 10.00(1H,s), 12.46(1H,brs).

EXAMPLE 2

Preparation of 6-(2-hydroxyethyl)-5-methylpyrazolo-[1,5-a]pyrimidin-7(4H)-one:

In 7.5 ml of water were suspended 1.17 g (6.04 mmol) of 3-{[1-(tetrahydro-2-oxo-3-furyl)ethylidene]amino}-pyrazole, and 0.73 g (7.23 mmol) of triethylamine were added to the suspension. The resultant mixture was stirred for 2 hours in an oil bath heated to 100° C. Thereafter, the reaction mixture was cooled with ice water, and concentrated hydrochloric acid was added thereto with stirring to adjust the pH of the reaction mixture to about 2 (deposit solids). Furthermore, a saturated aqueous solution of sodium hydrogencarbonate was added to adjust the pH of the mixture to about 4. Insoluble solids were collected by filtration, washed several times with water and air-dried to obtain 1.06 g (yield: 90.6%) of the intended product.

$^1$H-NMR (CDCl$_3$+CD$_3$OD, ppm): 2.38(3H,s), 2.81(2H,t,J=6.5 Hz), 3.74(2H,t,J=6.5 Hz), 5.97(1H,d,J=2.0 Hz), 7.80 (1H,d,J=2.0 Hz).

EXAMPLE 3

Preparation of 7-chloro-6-(2-chloroethyl)-5-methylpyrazolo[1,5-a]pyrimidine:

To 5.30 g (27.46 mmol) of 6-(2-hydroxyethyl)-5-methylpyrazolo[1,5-a]pyrimidin-7(4H)-one were added 8.5 ml (d=0.726, 61.10 mmol) of triethylamine. While cooling with ice water and stirring under a nitrogen atmosphere, 8.5 ml (d=1.645, 91.19 mmol) of phosphorus oxychloride were added dropwise to the mixture over 2 minutes. The resultant mixture was then stirred for 1 hour in an oil bath heated to 100° C. Thereafter, the reaction mixture was cooled with ice water and dissolved in 100 ml of chloroform, and the solution was poured into 500 ml of ice water. After full shake of the resultant mixture, the chloroform layer was separated, and the water layer was further extracted with chloroform (100 ml×2), and the chloroform layers were put together. After the whole chloroform layer was dried over anhydrous sodium sulfate, the solvent was distilled off. The residue was subjected to column chromatography on silica gel (chloroform) to obtain 3.7 g (yield: 59.8%) of the intended product.

$^1$H-NMR (CDCl$_3$, ppm): 2.71(3H,s), 3.35(2H,t,J=7.5 Hz), 3.76(2H,t,J=7.5 Hz), 6.67(1H,d,J=2.4 Hz), 8.15(1H,d,J=2.4 Hz).

EXAMPLE 4

Preparation of 7-chloro-6-(2-chloroethyl)-5-methyl-3-nitropyrazolo[1,5-a]pyrimidine:

While cooling with an ice-water-salt system, 23 ml of 90% nitric acid were added dropwise to 46 ml of concentrated sulfuric acid over 3 minutes and 30 seconds. While stirring at about −5° C., 5.0 g (21.74 mmol) of 7-chloro-6-(2-chloroethyl)-5-methylpyrazolo[1,5-a]pyrimidine as remained solid were then added gradually over 10 minutes and 30 seconds, and the resultant mixture was stirred for 5 hours at a temperature of from −5 to 5° C. Thereafter, the reaction mixture was poured into 800 ml of ice water and stirred for about 45 minutes. Solids deposited were collected by filtration, washed several times with water and air-dried to obtain 5.65 g (yield: 94.5%) of the intended product.

m.p.: 172.1–174.2° C. IR (KBr tablet, cm$^{-1}$): 1620, 1502, 1481, 1403, 1383, 1315, 1213. $^1$H-NMR (CDCl$_3$, ppm): 2.91(3H,s), 3.43(2H,t,J=7.0 Hz), 3.83(2H,t,J=7.0 Hz), 8.80 (1H,s).

EXAMPLE 5

Preparation of Compound 1 ($R^1$: tert-butyl, $R^2$: methyl, $R^3$: nitro):

Preparation of 8-tert-butyl-6,7-dihydro-5-methyl-3-nitro-8H-pyrrolo[3,2-e]pyrazolo[1,5-a]pyrimidine:

In 18 ml of anhydrous dimethylformamide were dissolved 1.75 g (6.36 mmol) of 7-chloro-6-(2-chloroethyl)-5-methyl-3-nitropyrazolo[1,5-a]pyrimidine, and 0.93 g (12.72 mmol) of tert-butylamine and 1.61 g (15.94 mmol) of triethylamine were successively added to the solution, and the mixture was stirred at room temperature for 6 hours. Thereafter, the reaction mixture was poured into water and extracted with ethyl acetate (150 ml×2). The ethyl acetate layers were put together, washed with a saturated saline solution and dried over anhydrous magnesium sulfate, and the solvent was then distilled off. The residue was subjected to column chromatography on silica gel (hexane:ethyl acetate=2:1) and recrystallized from ethanol to obtain 0.78 g (yield: 44.6%) of the intended product.

$^1$H-NMR (CDCl$_3$, ppm): 1.71(9H,s), 2.47(3H,s), 3.06 (2H,t,J=9.2 Hz), 4.09(2H,t,J=9.2 Hz), 8.61(1H,s).

EXAMPLE 6

Preparation of Compound 2 ($R^1$: tert-amyl, $R^2$: methyl, $R^3$: nitro):

Compound 2 was obtained in 37.8% yield in the same manner as in Example 2 except that tert-amylamine was used instead of ter-butylamine.

$^1$H-NMR (CDCl$_3$, ppm): 0.89(3H,t,J=7.6 Hz), 1.64(6H,s), 2.27(2H,q,J=7.6 Hz), 2.47(3H,s), 3.07(2H,t,J=9.0 Hz), 4.09 (2H,t,J=9.0 Hz), 8.59(1H,s).

EXAMPLE 7

Preparation of Compound 3 ($R^1$: cyclopentyl, $R^2$: methyl, $R^3$: nitro):

Compound 3 was obtained in 82.9% yield in the same manner as in Example 2 except that cyclopentylamine was used instead of tert-butylamine.

IR (KBr tablet, cm$^{-1}$): 1626, 1617, 1492, 1394, 1234, 1196. m.p.: 228–234° C. $^1$H-NMR (CDCl$_3$, ppm): 1.60–1.85

(6H,m), 1.90–2.10(2H,m), 2.46(3H,s), 3.16(2H,t,J=8.9 Hz), 3.92(2H,t,J=8.9 Hz), 5.81(1H,m), 8.56(1H,s).

EXAMPLE 8

Preparation of Compound 4 ($R^1$: cyclohexyl, $R^2$: methyl, $R^3$: nitro):

Compound 4 was obtained in 76.6% yield in the same manner as in Example 2 except that cyclohexylamine was used instead of tert-butylamine.

IR (KBr tablet, $cm^{-1}$): 1622, 1613, 1491, 1454, 1441, 1397, 1245, 1231, 1199. m.p.: 256.8–258.1° C. $^1$H-NMR (CDCl$_3$, ppm): 1.00–1.30(1H,m), 1.35–2.00(9H,m), 2.46 (3H,s), 3.14(2H,t,J=9.0 Hz), 3.91(2H,t,J=9.0 Hz), 5.15–5.35 (1H,m), 8.57(1H,s).

EXAMPLE 9

Preparation of Compound 5 ($R^1$: sec-butyl, $R^2$: methyl, $R^3$: nitro):

Compound 5 was obtained in 74.3% yield in the same manner as in Example 2 except that sec-butylamine was used instead of tert-butylamine.

IR (KBr tablet, $cm^{-1}$): 1626, 1614, 1488, 1443, 1397, 1229, 1200, 1180. m.p.: 257.9–260.1° C. $^1$H-NMR (CDCl$_3$, ppm): 0.94(3H,t,J=7.4 Hz), 1.31(3H,d,J=6.8 Hz), 1.55–1.75 (2H,m), 2.48(3H,s), 3.17(2H,t,J=9.2 Hz), 3.73–3.95(2H,m), 5.50–5.68(1H,m), 8.58(1H,s).

EXAMPLE 10

Preparation of Compound 6 ($R^1$: cyclopentyl, $R^2$: methyl, $R^3$: amino):

0.287 g of Compound 3 were weighed out, and 0.95 g of anhydrous tin (II) chloride and 2 ml of anhydrous ethanol were added. The resultant mixture was stirred at 70–80° C. or 1 hour and 50 minutes under a nitrogen atmosphere. The reaction mixture was cooled with ice water, and 20 ml of ethyl acetate and 30 ml of a saturated aqueous solution of sodium hydrogencarbonate were poured into the reaction mixture while cooling with ice water and stirring. Insoluble matter was separated by filtration and washed several times with ethyl acetate. The washings were put together with the filtrate, and the ethyl acetate layer was separated. The water layer was further extracted with ethyl acetate, and all the ethyl acetate layers were put together. After the whole ethyl acetate layer was dried over anhydrous sodium sulfate, the solvent was distilled off. The residue was recrystallized from ethyl acetate to obtain 0.114 g (yield: 44.4%) of Compound 6.

IR (KBr tablet, $cm^{-1}$): 3378, 1578, 1561, 1332. m.p.: 134–134.5° C. $^1$H-NMR (CDCl$_3$, ppm): 1.55–1.80(6H,m), 1.80–2.05(2H,m), 2.35(3H,s), 3.07(2H,t,J=9.0 Hz), 3.77 (2H,t,J=9.0 Hz), 5.88–6.05(1H,m), 7.70(1H,s).

EXAMPLE 11

Preparation of Compound 7 ($R^1$: cyclopentyl, $R^2$: methyl, $R^3$: acetylamino):

0.20 g of Compound 3 were weighed out and then dissolved in 1.8 ml of acetic acid. To the solution, were added 0.13 g of reduced iron as remained solid at once. The mixture was then heated and stirred at 100° C. for 1.5 hours under a nitrogen atmosphere. Acetic acid was then distilled out of the reaction mixture, and 10 ml of chloroform were added to the residue. The resultant mixture was poured into 30 ml of a saturated aqueous solution of sodium hydrogencarbonate. Insoluble matter was separated by filtration, and the chloroform layer was separated from the water layer. The water layer was further extracted with chloroform, and all the chloroform layers were put together. After the whole chloroform layer was dried over anhydrous sodium sulfate, the solvent was distilled off to obtain 0.20 g (yield: 95.2%) of Compound 7.

IR (KBr tablet, $cm^{-1}$): 3234, 1633, 1582, 1558, 1530, 1329, 1250, 1166. m.p.: 233–234° C. $^1$H-NMR (CDCl$_3$, ppm): 1.60–1.80(6H,m), 1.85–2.05(2H,m), 2.19(3H,s), 2.33 (3H,s), 3.08(2H,t,J=9.2 Hz), 3.82(2H,t,J=9.2 Hz), 5.93–6.10 (1H,m), 8.28(1H,brs), 8.58(1H,s).

EXAMPLE 12

Preparation of Compound 8 ($R^1$: cyclopentyl, $R^2$: methyl, $R^3$: trifluoromethanesulfonylamino):

In 2 ml of anhydrous methylene chloride were dissolved 0.1 g of Compound 6. While cooling with ice water and stirring under a nitrogen atmosphere, a solution of 0.13 g of trifluoromethanesulfonic anhydride in 2 ml of anhydrous methylene chloride was added dropwise to the solution, and stirring was continued for 25 minutes as it is. The reaction mixture was poured into chloroform/cooled saturated aqueous solution of sodium hydrogencarbonate. The chloroform layer was separated and dried over anhydrous sodium sulfate, and the solvent was then distilled off. The residue was purified by column chromatography on silica gel (chloroform:methanol=100:0→100:1) to obtain 0.13 g (yield: 86.7%) of Compound 8.

IR (KBr tablet, $cm^{-1}$): 1636, 1300, 1203, 1163. m.p.: 178–179° C. $^1$H-NMR (CDCl$_3$, ppm): 1.62–1.87(6H,m), 1.90–2.10(2H,m), 2.37(3H,s), 3.11(2H,t,J=8.6 Hz), 3.96 (2H,t,J=8.6 Hz), 5.95–6.10(1H,m), 7.98(1H,s).

EXAMPLE 13

Preparation of Compound 9 ($R^1$: cyclopentyl, $R^2$: methyl, $R^3$: trifluoroacetylamino):

In 4.5 ml of anhydrous pyridine were dissolved 0.257 g of Compound 6. While stirring at room temperature under a nitrogen atmosphere, 0.42 ml of trifluoroacetic anhydride were added dropwise to the solution, and stirring was continued for 1 hour and 10 minutes as it is. The reaction mixture was concentrated under reduced pressure, and the residue was dissolved in 20 ml of chloroform. The solution was then poured into 30 ml of water. After the resultant mixture was alkalized with a saturated aqueous solution of sodium hydrogencarbonate, the chloroform layer was separated. The chloroform layer was dried over anhydrous sodium sulfate, and the solvent was then distilled off. The residue was recrystallized from ethyl acetate to obtain 0.129 g (yield: 36.5%) of Compound 9.

IR (KBr tablet, $cm^{-1}$): 1702, 1628, 1605, 1318, 1307, 1209, 1192, 1154. m.p.: 175–176° C. $^1$H-NMR (CDCl$_3$, ppm): 1.60–1.85(6H,m), 1.85–2.10(2H,m), 2.33(3H,s), 3.10 (2H,t,J=9.2 Hz), 3.85(2H,t,J=9.2 Hz), 5.90–6.08(1H,m), 8.63(1H,s).

EXAMPLE 14

Preparation of Compound 10 ($R^1$: cyclopentyl, $R^2$: methyl, $R^3$: methanesulfonylamino):

In 2 ml of anhydrous methylene chloride were dissolved 0.14 g of Compound 6. While cooling with ice water and stirring under a nitrogen atmosphere, 0.2 ml of triethylamine were added to the solution, and a solution of 75 mg of methanesulfonyl chloride in 2 ml of anhydrous methylene chloride was further added dropwise. The resultant mixture was stirred for 30 minutes while cooling with ice water under a nitrogen atmosphere, and then poured into 5 ml of chloroform and 30 ml of cold water. After the chloroform layer was separated and dried over anhydrous sodium sulfate, the solvent was distilled off. The residue was purified by column chromatography on silica gel (elution solvent: chloroform) and recrystallized from ethanol to obtain 0.105 g (yield: 58.3%) of Compound 10.

IR (KBr tablet, cm$^{-1}$): 1618, 1595, 1542, 1323, 1149. m.p.:172–174° C. $^1$H-NMR (CDCl$_3$, ppm):

1.60–1.85(6H,m), 1.85–2.05(2H,m), 2.35(3H,s), 3.04 (3H,s), 3.08(2H,t,J=9.9 Hz), 3.82(2H,t,J=9.9 Hz), 5.90–6.05 (1H,m), 8.04(1H,s).

EXAMPLE 15

Preparation of Compound 12 (R$^1$: cyclopentyl, R$^2$: methyl, R$^3$: ethyloxalylamino):

In 4 ml of anhydrous methylene chloride were dissolved 0.257 g of Compound 6. While cooling with ice water and stirring under a nitrogen atmosphere, 0.37 ml of triethylamine were added to the solution, and a solution of 164 mg of ethyloxalyl chloride in 2 ml of anhydrous methylene chloride was further added dropwise. The resultant mixture was stirred for 60 minutes while cooling with ice water under a nitrogen atmosphere, and then poured into 10 ml of chloroform and 50 ml of cold water. After the chloroform layer was separated and dried over anhydrous sodium sulfate, the solvent was distilled off. The residue was purified by column chromatography on silica gel (elution solvent: chloroform) and recrystallized from ethanol to obtain 0.271 g (yield: 75.9%) of Compound 12.

IR (KBr tablet, cm$^{-1}$): 3400, 1764, 1702, 1625, 1609, 1504. m.p.: 185–186° C. $^1$H-NMR (CDCl$_3$, ppm): 1.43(3H, t,J=7.0 Hz), 1.60–1.85(6H,m), 1.85–2.05(2H,m), 2.35(3H, s), 3.10(2H,t,J=9.0 Hz), 3.83(2H,t,J=9.0 Hz), 4.42(2H,q,J= 7.0 Hz), 5.90–6.06(1H,m), 8.69(1H,s), 9.32(1H,brs).

EXAMPLE 16

Preparation of Compound 11 (R$^1$: cyclopentyl, R$^2$: methyl, R$^3$: oxalylamino):

In 6.8 ml of methanol were suspended 0.34 g of Compound 12. While cooling with ice water and stirring under a nitrogen atmosphere, 1.3 ml of a 1N aqueous solution of sodium hydroxide were added to the suspension, and stirring was continued for 1 hour while cooling with ice water under a nitrogen atmosphere. Furthermore, 6 ml of water were added, and the mixture was stirred at room temperature for 8.5 hours. After 20 ml of methanol were added, and the resultant mixture was stirred, insoluble matter was collected by filtration, dried and then dissolved in 15 ml of hot ethanol. After the resultant solution was filtered, and the solvent was distilled out of the filtrate, 15 ml of ethanol were added to the residue, and a 1N aqueous solution of hydrogen chloride was further added to adjust the pH of the mixture to about 3. Solids deposited were collected by filtration and dried to obtain 0.17 g (yield: 54.8%) of Compound 11.

IR (KBr tablet, cm$^{-1}$): 3235, 2800–2350, 1681, 1625, 1547, 1496, 1346, 1296, 1173. m.p.: 255–255.5° C.

EXAMPLE 17

Preparation of Compound 13 (R$^1$: tert-butyl, R$^2$: methyl, R$^3$: N-(1H-tetrazol-5-yl)carbamoyl):

380 mg of Compound 34, which will be described in a subsequent example, were weighed out, and 3 ml of anhydrous DMF were added. To the mixture, were added 280 mg of 1,1'-carbonyldiimidazole, and the resultant mixture was stirred at 90° C. for 30 minutes. In a state that crystals were dissolved, 170 mg of 5-amino-1H-tetrazole were added, and stirring was continued for additional 3 hours at 90° C. After the reaction mixture was then cooled to 0° C., and water was added thereto, the reaction mixture was acidified with concentrated hydrochloric acid. Thereafter, the reaction mixture was neutralized with a saturated aqueous solution of sodium hydrogencarbonate. Crystals deposited were collected by filtration and dried. The crystals were washed with chloroform and then dried to obtain 180 mg (yield: 38.2%) of Compound 13.

IR (KBr tablet, cm$^{-1}$): 1667, 1580, 1502, 1303, 1201. $^1$H-NMR (DMSO-d$_6$, ppm): 1.50(9H,s), 2.31(3H,s), 2.84 (2H,t,J=8.9 Hz), 3.95(2H,t,J=8.9 Hz), 8.42(1H,s), 11.59(1H, s), 15.80(1H,brs).

EXAMPLE 18

Preparation of Compound 14 (R$^1$: tert-amyl, R$^2$: methyl, R$^3$: N-(1H-tetrazol-5-yl)carbamoyl):

Compound 14 was obtained in an amount of 280 mg (yield: 60.0%) in the same manner as in Example 14 except that 400 mg of Compound 35, which will be described in a subsequent example, were used.

IR (KBr tablet, cm$^{-1}$): 1666, 1578, 1501, 1297, 1200. $^1$H-NMR (DMSO-d$_6$, ppm): 0.90(3H,t,J=7.3 Hz), 1.67(6H, s), 2.33(2H,q,J=7.3 Hz), 2.45(3H,s), 3.09(2H,t,J=8.9 Hz), 4.13(2H,t,J=8.9 Hz), 8.46(1H,s), 11.89(1H,s), 15.60(1H, brs).

EXAMPLE 19

Preparation of Compound 15 (R$^1$: cyclopentyl, R$^2$: methyl, R$^3$: 1H-tetrazol-5-yl):

To 1.62 g of 3-cyano-8-cyclopentyl-5-methyl-8H-pyrrolo [3,2-e]pyrazolo[1,5-a]pyrimidine, 0.45 g of sodium azide and 0.51 g of ammonium acetate were added 20 ml of anhydrous DMF, and the resultant mixture was stirred at 160° C. for 9 hours under a nitrogen atmosphere. In the course of the reaction, 0.45 g of sodium azide and 0.51 g of ammonium acetate were suitably added. While cooling with ice water, 30 ml of water was added to the reaction mixture, and concentrated hydrochloric acid was then added to adjust the pH of the reaction mixture to 1. Thereafter, the pH of the reaction mixture was adjusted to 4–5 with a saturated aqueous solution of sodium hydrogencarbonate. The reaction mixture was extracted with chloroform, and the resultant extract was dried and then concentrated. The residue was purified by column chromatography on silica gel (elution solvent: chloroform:methanol=10:0→30:1) to obtain 0.54 g (yield: 28.7%) of Compound 15.

IR (KBr tablet, cm$^{-1}$): 1625, 1581, 1322, 1259, 1201. m.p.: 266.5–267.5° C. $^1$H-NMR (CDCl$_3$, ppm): 1.60–1.85 (6H,m), 1.85–2.10(2H,m), 2.40(3H,s), 3.14(3H,t,J=9.2 Hz), 3.90(3H,t,J=9.2 Hz), 5.54(1H,brs), 5.80–6.00(1H,m), 8.57 (1H,s).

EXAMPLE 20

Preparation of Compound 16 (R$^1$: tert-butyl, R$^2$: methyl, R$^3$: 1H-tetrazol-5-yl):

Compound 16 was obtained in an amount of 0.42 g (yield: 26.1%) in the same manner as in Example 16 except that 1.38 g of 8-tert-butyl-3-cyano-5-methyl-8H-pyrrolo-[3,2-e] pyrazolo[1,5-a]pyrimidine were used.

IR (KBr tablet, cm$^{-1}$): 1627, 1560, 1245, 1196. m.p.: 270° C. $^1$H-NMR (CDCl$_3$:DMSO-d$_6$=4:1, ppm): 1.75(9H,s), 2.46

(3H,s), 3.06(2H,t,J=8.9 Hz), 4.08(2H,t,J=8.9 Hz), 5.90(1H, brs), 8.51(1H,s).

EXAMPLE 21

Preparation of Compound 17 ($R^1$: tert-amyl, $R^2$: methyl, $R^3$: 1H-tetrazol-5-yl):

Compound 17 was obtained in an amount of 0.46 g (yield: 28.4%) in the same manner as in Example 16 except that 1.40 g of 8-tert-amyl-3-cyano-5-methyl-8H-pyrrolo-[3,2-e]pyrazolo[1,5-a]pyrimidine were used.

IR (KBr tablet, $cm^{-1}$): 1633, 1569, 1256, 1186. m.p.: 246° C. $^1$H-NMR (DMSO-$d_6$, ppm): 0.86(3H,t,J=7.3 Hz), 1.64 (6H,s), 2.31(2H,q,J=7.3 Hz), 2.40(3H,s), 3.04(2H,t,J=8.7 Hz), 4.09(2H,t,J=8.7 Hz), 8.54(1H,s).

EXAMPLE 22

Preparation of Compound 18 ($R^1$: cyclopentyl, $R^2$: methyl, $R^3$: carbamoyl):

Added to 0.53 g of 3-cyano-8-cyclopentyl-6,7-dihydro-5-methyl-8H-pyrrolo[3,2-e]pyrazolo[1,5-a]pyrimidine were 2 ml of ethanol, and a solution of 0.58 g of sodium hydroxide in 2 ml of water was further added. The resultant mixture was heated under reflux for 8 hours under a nitrogen atmosphere. After the reaction mixture was cooled, 30 ml of water were added to the reaction mixture. Insoluble solids were collected by filtration and air-dried to obtain 0.33 g (yield: 57.9%) of Compound 18.

IR (KBr tablet, $cm^{-1}$): 3334, 3135, 1656, 1616, 1590, 1518, 1465, 1330, 1259, 1196. m.p.: at least 280° C. $^1$H-NMR (CDCl$_3$, ppm): 1.58–1.85(6H,m), 1.85–2.05(2H, m), 2.35(3H,s), 3.11(3H,t,J=8.9 Hz), 3.85(3H,t,J=8.9 Hz), 5.45(1H,brs), 5.85–6.00(1H,m), 8.36(1H,brs), 8.45(1H,s).

EXAMPLE 23

Preparation of Compound 19 ($R^1$: cyclopentyl, $R^2$: amino, $R^3$: nitro):

In 18 ml of anhydrous acetone were suspended 1.2 g of Compound 23 which will be described in a subsequent example. While cooling with ice water and stirring under a nitrogen atmosphere, 0.65 ml of triethylamine were added to the suspension. A solution of 0.47 g of ethyl chlorocarbonate in 2 ml of anhydrous acetone was then added dropwise to the suspension, and the mixture was stirred for 1 hour. Under the same conditions, a solution of 0.54 g of sodium azide in 2 ml of water was added dropwise, and the mixture was stirred for 1 hour and then allowed to stand for 2 hours. The reaction mixture was poured into 200 ml of water, and insoluble matter was collected by filtration and washed with water. The insoluble matter was suspended in 25 ml of toluene, and the suspension was heated and stirred at 125° C. for 4 hours. After the suspension was cooled with ice water, 120 ml of chloroform were added to dissolve the suspension therein. The solution was dried over anhydrous sodium sulfate and then concentrated. The residue was purified by column chromatography on silica gel (elution solvent: chloroform:methanol=100:0→100:1) and concentrated. The resultant residue was dissolved in 100 ml of chloroform, and the solution was extracted with 1N hydrochloric acid. The hydrochloric acid layer was alkalized with sodium hydrogencarbonate and extracted with chloroform to obtain 0.74 g (yield: 67.9%) of Compound 19.

IR (KBr tablet, $cm^{-1}$): 3487, 3310, 3210, 1624, 1583, 1400, 1258, 1214. m.p.: 279–280° C. $^1$H-NMR (CDCl$_3$, ppm): 1.60–1.85(6H,m), 1.85–2.05(2H,m), 2.97(2H,t,J=8.9 Hz), 3.86(3H,t,J=8.9 Hz), 5.60–5.80(1H,m), 5.72(2H,brs), 8.42(1H,s).

EXAMPLE 24

Preparation of Compound 20 ($R^1$: sec-butyl, $R^2$: amino, $R^3$: nitro):

Compound 20 (yield: 45.8%) was prepared in accordance with the same process as in Example 20 except that Compound 24, which will be described in a subsequent example, was used as a raw material.

IR (KBr tablet, $cm^{-1}$): 1640, 1625, 1580, 1399, 1256. m.p.: 201.5–203.1° C. $^1$H-NMR (CDCl$_3$, ppm): 0.92(3H,t, J=7.6 Hz), 1.25(3H,d,J=6.5 Hz), 1.45–1.75(2H,m), 2.98(2H, t,J=8.9 Hz), 3.79(2H,s,J=8.9 Hz), 5.41(1H,s,J=6.5 Hz), 6.14 (2H,brs), 8.40(1H,s).

EXAMPLE 25

Preparation of ethyl (tetrahydro-2-oxo-3-furyl)-glyoxylate:

25.80 g of metal sodium were added to 500 ml of ethanol dried over molecular sieves and dissolved. Then, 148.21 g of diethyl oxalate were added, and the reaction system was chilled to −15 to −10° C. After a solution of 88.79 g of γ-butyrolactone in 60 ml of ethanol was added while maintaining this temperature, and the resultant mixture was stirred for 2 hours, it was stirred at room temperature for 16 hours. The reaction mixture was poured into 1 liter of ice water, and the pH of the mixture was then adjusted to 4–5 with concentrated hydrochloric acid, and the mixture was extracted with chloroform. The chloroform layer was dried over anhydrous sodium sulfate, and the solvent was distilled off under reduced pressure. The crude product thus obtained was distilled under reduced pressure to obtain 156.21 g (yield: 83.1%) of the intended product (pale yellow liquid) as a fraction of 150–160° C. (5–6 mmHg).

$^1$H-NMR (CDCl$_3$, ppm):

1.39(3H,t,J=7.4 Hz), 3.30(2H,t,J=7.4 Hz), 4.37(2H,q,J= 7.4 Hz), 4.50(2H,t,J=7.4 Hz), 10.92(1H,brs).

EXAMPLE 26

Preparation of ethyl 7-chloro-6-(2-chloroethyl)-3-nitropyrazolo[1,5-a]pyrimidine-5-carboxylate:

While stirring at room temperature, 8.12 g of synthetic zeolite A-4 powder were added to a solution of 8.12 g (97.70 mmol) of 3-aminopyrazole in 32 ml of acetic acid. Furthermore, a solution of 8.19 g (97.78 mmol) of ethyl (tetrahydro-2-oxo-3-furyl)glyoxylate obtained in Example 25 in 40 ml of acetic acid was added dropwise over 2 minutes while cooling with ice water and stirring, and the mixture was stirred for 4 hours at room temperature. Thereafter, insoluble matter was removed by filtration, and the filtrate was concentrated under reduced pressure. The residue was dissolved in 150 ml of chloroform, and the solution was poured into 700 ml of water. After full shake of the resultant mixture, the chloroform layer was separated, and the water layer was further extracted with chloroform (150 ml×2). After all the chloroform layers were put together and dried over anhydrous sodium sulfate, the solvent was distilled off. The residue was purified by column chromatography on silica gel (chloroform) to obtain 5.36 g of ethyl 6-(2-hydroxyethyl)pyrazolo[1,5-a]pyrimidin-7(4H)-one-5-carboxylate. To this product were added 7 ml (d=1.645, 75.10 mmol) of phosphorus oxychloride, and the mixture was stirred for 40 minutes in an oil bath heated to 100° C. under a nitrogen atmosphere. The reaction mixture was then cooled to about room temperature, and 7 ml (d=0.726, 50.32 mmol) of triethylamine was added to the reaction mixture. The resultant mixture was stirred for 30 minutes in the oil bath heated to 100° C. Thereafter, the reaction mixture was cooled with ice water, and 100 ml of chloroform were added thereto. The resultant mixture was poured into 600 ml of ice water and fully shaken. The chloroform layer was then separated, and the water layer was extracted with chloroform (100 ml×2). After all the chloroform layers were put together and dried over anhydrous magnesium sulfate, the solvent was distilled off. The residue was subjected to column chromatography on silica gel (chloroform) to obtain 3.60 g of ethyl 7-chloro-6-(2-chloroethyl)pyrazolo[1,5-a] pyrimidine-5-carboxylate. While cooling with ice water and stirring, 1.60 ml of 90% nitric acid and one drop of concentrated sulfuric acid were successively added to 14.2 ml of acetic anhydride, and the resultant mixture was then chilled to −10° C. While keeping this mixture at −5 to 0C., a solution of 3.60 g of ethyl 7-chloro-6-(2-chloro-ethyl) pyrazolo[1,5-a]pyrimidine-5-carboxylate in 4.30 ml of acetic anhydride was added dropwise thereto. After the resultant mixture was stirred for 20 minutes under the same conditions, it was poured into 300 ml of ice water, followed by extraction with 400 ml of ethyl acetate. After the resultant organic layer was washed twice with a saturated aqueous solution of sodium hydrogencarbonate and once with a saturated saline solution, and dried over anhydrous magnesium sulfate, the solvent was distilled off. The residue was subjected to column chromatography on silica gel (ethyl acetate:n-hexane=1:5, chloroform) to obtain 2.49 g (yield: 7.6%) of the intended product.

$^1$H-NMR (CDCl$_3$, ppm): 1.49(3H,t,J=7.3 Hz), 3.61(2H,t, J=7.0 Hz), 3.85(2H,t,J=7.0 Hz), 4.56(2H,q,J=7.3 Hz), 8.93 (1H,s).

EXAMPLE 27

Preparation of ethyl 8-cyclopentyl-6,7-dihydro-3-nitro-8H-pyrrolo[3,2-e]pyrazolo[1,5-a]pyrimidine-5-carboxylate (Compound 21) (first process):

In 12 ml of anhydrous dimethylformamide were dissolved 1.16 g (3.48 mmol) of ethyl 7-chloro-6-(2-chloroethyl)-3-nitropyrazolo[1,5-a]pyrimidine-5-carboxylate, and 2.4 ml (d=0.863, 24.32 mmol) of cyclopentylamine were added to the solution, and the resultant mixture was stirred for 4 hours at room temperature. The reaction mixture was then poured into ice water. Insoluble solids were collected by filtration, washed with water and air-dried to obtain 1.15 g (yield: 95.7%) of the intended product.

$^1$H-NMR (CDCl$_3$, ppm): 1.47(3H,t,J=7.3 Hz), 1.65–1.90 (6H,m), 1.95–2.15(2H,m), 3.58(2H,t,J=8.9 Hz), 4.00(2H,t, J=8.9 Hz), 4.46(2H,q,J=7.3 Hz), 5.85–6.05(1H,m), 8.67(1H, s).

EXAMPLE 28

Preparation of Compound 21 (R$^1$: cyclopentyl, R$^2$: ethoxycarbonyl, R$^3$: nitro) (second process):

In 48 ml of anhydrous DMF were dissolved 3.6 g of ethyl 7-chloro-6-(2-chloroethyl)pyrazolo[1,5-a]pyrimidine-5-carboxylate. While stirring at room temperature under a nitrogen atmosphere, 7.3 ml of cyclopentylamine were added to the solution, and the mixture was stirred for 1 hour and 20 minutes. The reaction mixture was poured into 250 ml of ice water. Insoluble matter was collected by filtration and air-dried to obtain 3.20 g (yield: 85.3%) of ethyl 8-cyclopentyl-6,7-dihydro-8H-pyrrolo[3,2-e]pyrazolo[1,5-a]-pyrimidine-5-carboxylate. While stirring at −5 to 0° C., 1.16 g of this product were gradually added to mixed acid prepared by mixing 7.8 ml of concentrated sulfuric acid and 3.9 ml of 90% nitric acid. After being stirred for 5 minutes under the same conditions, the reaction mixture was poured into 200 ml of ice water, followed by extraction with chloroform. After the chloroform layer was dried over anhydrous sodium sulfate, the solvent was then distilled off, and the residue was purified by column chromatography on silica gel (ethyl acetate:n-hexane=1:1) to obtain 0.76 g (yield: 57.0%) of Compound 21.

$^1$H-NMR (CDCl$_3$, ppm): 1.47(3H,t,J=7.3 Hz), 1.65–1.90 (6H,m), 1.95–2.15(2H,m), 3.58(2H,t,J=8.9 Hz), 4.00(2H,t, J=8.9 Hz), 4.46(2H,q,J=7.3 Hz), 5.85–6.05(1H,m), 8.67(1H, s).

EXAMPLE 29

Preparation of Compound 22 (R$^1$: tert-butyl, R$^2$: ethoxycarbonyl, R$^3$: nitro):

Compound 22 was obtained (yield: 90.1%) in the same manner as in Example 23 except that sec-butylamine was used instead of cyclopentylamine.

$^1$H-NMR (CDCl$_3$, ppm): 0.96(3H,t,J=7.3 Hz), 1.37(3H, d,J=6.5 Hz), 1.47(3H,t,J=7.0 Hz), 1.64–1.80(2H,m), 3.58 (3H,t,J=7.3 Hz), 3.82–4.04(2H,m), 4.46(2H,q,J=7.0 Hz), 5.73(1H,s,J=6.5 Hz), 8.67(1H,s).

EXAMPLE 30

Preparation of Compound 23 (R$^1$: cyclopentyl, R$^2$: carboxyl, R$^3$: nitro):

In 30 ml of tetrahydrofuran and 10 ml of methanol were suspended 2.05 g of Compound 21. While cooling with ice water, 20 ml of a 0.5N aqueous solution of sodium hydroxide were added dropwise to the suspension, and the resultant mixture was allowed to stand for 15 minutes. Additional 20 ml of a 0.5N aqueous solution of sodium hydroxide were added dropwise. After the mixture had stood for 15 minutes under cooling with ice water, it was subjected to an ultrasonic treatment, and concentrated sulfuric acid was added to adjust the pH of the thus-treated reaction mixture to 3. To the reaction mixture were added 200 ml of water, and insoluble solids were collected by filtration, washed with water and dried to obtain 1.21 g (yield: 64.2%) of Compound 23.

$^1$H-NMR (DMSO-d$_6$, ppm): 1.50–2.00(8H,m), 3.40(2H, t,J=8.6 Hz), 3.99(2H,t,J=8.6 Hz), 5.78(1H,q,J=8.0 Hz), 8.93 (1H,s).

EXAMPLE 31

Preparation of Compound 24 (R$^1$: sec-butyl, R$^2$ carboxyl, R$^3$: nitro):

Compound 24 was obtained (yield: 85.7%) by the treatment of Compound 22 in the same manner as in Example 26.

$^1$H-NMR (DMSO-d$_6$, ppm): 0.86(3H,t,J=7.3 Hz), 1.29 (3H,d,J=6.5 Hz), 1.50–1.80(2H,m), 3.42(3H,t,J=8.9 Hz), 3.80–4.04(2H,m), 5.45–5.65(1H,m), 8.93(1H,s), 13.56(1H, brs).

EXAMPLE 32

Preparation of Compound 25 (R$^1$: tert-butyl, R$^2$: methyl, R$^3$: trifluoroacetyl):

In 9 ml of anhydrous dimethylformamide were dissolved 500 mg (2.17 mmol) of 7-chloro-6-(2-chloroethyl)-5-methylpyrazolo[1,5-a]pyrimidine. To the suspension, were successively added 191 mg (2.61 mmol) of tert-butylamine and 660 mg (6.53 mmol) of triethylamine, and the resultant mixture was stirred for 172 hours at room temperature. The reaction mixture was poured into 50 ml of water and stirred for several minutes, followed by extraction with chloroform (10 ml×4). After all the chloroform layers were put together and dried over anhydrous sodium sulfate, the solvent was distilled off.

The residue was dissolved in 20 ml of ethyl acetate, and the solution was washed with a saturated saline solution (50 ml×6) and dried over anhydrous sodium sulfate. The solvent was then distilled off, and the residue was subjected to column chromatography on silica gel (chloroform:n-hexane=8:2) to obtain 0.24 g (yield: 47.9%) of 8-tert-butyl-6,7-dihydro-5-methyl-8H-pyrrolo[3,2-e]pyrazolo[1,5-a]pyrimidine.

IR (KBr tablet, cm$^{-1}$): 1593, 1558, 1498, 1313, 1250, 1209, 749. m.p.:143.5–145.5° C. $^1$H-NMR (CDCl$_3$, ppm): 1.73(9H,s), 2.34(3H,s), 2.96(2H,t,J=9.0 Hz), 3.95(2H,t,J=9.0 Hz), 6.28(1H,d,J=2.7 Hz), 7.92(1H,d,J=2.7 Hz).

In 2.5 ml of anhydrous methylene chloride were dissolved 0.24 g of the thus-obtained 8-tert-butyl-6,7-dihydro-5-methyl-8H-pyrrolo[3,2-e]pyrazolo[1,5-a]pyrimidine. To the solution, were added 0.3 ml of trifluoroacetic anhydride, and the mixture was stirred for 7 hours. The reaction mixture was poured into 10 ml of chloroform and 50 ml of water, and alkalized with a saturated aqueous solution of sodium hydrogencarbonate. The organic layer was separated, dried over anhydrous sodium sulfate and concentrated. The residue was purified by column chromatography on silica gel (chloroform) and recrystallized from ethanol to obtain 0.20 g (yield: 58.5%) of Compound 25.

IR (KBr tablet, cm$^{-1}$): 1672, 1596, 1583, 1503, 1222, 1184, 1157, 1123, 883, 730. m.p.: 201.9–203.2° C. $^1$H-NMR (CDCl$_3$, ppm): 1.72(9H,s), 2.46(3H,s), 3.05(2H,t,J=9.2 Hz), 4.07(2H,t,J=9.2 Hz), 8.41(1H,s).

EXAMPLE 33

Preparation of Compound 26 (R$^1$: tert-amyl, R$^2$: methyl, R$^3$: trifluoroacetyl):

Compound 26 was obtained (yield: 43.0%) in the same manner as in Example 28 except that 8-tert-amyl-6,7-dihydro-5-methyl-8H-pyrrolo[3,2-e]pyrazolo[1,5-a]pyrimidine prepared from 7-chloro-6-(2-chloroethyl)-5-methylpyrazolo[1,5-a]pyrimidine and tert-amylamine was used.

IR (KBr tablet, cm$^{-1}$): 1671, 1584, 1501, 1222, 1185, 1155, 1122, 882. m.p.: 147.3–148.8° C. $^1$H-NMR (CDCl$_3$, ppm): 0.89(3H,t,J=7.8Hz), 1.65(6H,s), 2.29(2H,q,J=7.8 Hz), 2.46(3H,s), 3.06(2H,t,J=9.2 Hz), 4.08(2H,t,J=9.2 Hz), 8.39 (1H,s).

EXAMPLE 34

Preparation of Compound 27 (R$^1$: cyclopentyl, R$^2$: methyl, R$^3$: trifluoroacetyl):

Compound 27 was obtained (yield: 85.0%) in the same manner as in Example 28 except that 8-cyclopentyl-6,7-dihydro- 5-methyl-8H-pyrrolo[3,2-e]pyrazolo[1,5-a]pyrimidine prepared from 7-chloro-6-(2-chloroethyl)-5-methylpyrazolo[1,5-a]pyrimidine and cyclopentylamine was used.

IR (KBr tablet, cm$^{-1}$): 1678, 1626, 1193, 1127, 885. m.p.: 160.1–163.3° C. $^1$H-NMR (CDCl$_3$, ppm): 1.58–1.88(6H,m), 1.88–2.10(2H,m), 2.46(3H,s), 3.15(2H,t,J=9.2 Hz), 3.90 (2H,t,J=9.2 Hz), 5.73–5.95(1H,m), 8.39(1H,s).

EXAMPLE 35

Preparation of Compound 28 (R$^1$: cyclohexyl, R$^2$: methyl, R$^3$: trifluoroacetyl):

Compound 28 was obtained (yield: 18.1%) in the same manner as in Example 28 except that 8-cyclohexyl-6,7-dihydro-5-methyl-8H-pyrrolo[3,2-e]pyrazolo[1,5-a]pyrimidine prepared from 7-chloro-6-(2-chloroethyl)-5-methylpyrazolo-[1,5-a]pyrimidine and cyclohexylamine was used.

IR (KBr tablet, cm$^{-1}$): 1677, 1624, 1601, 1515, 1508, 1241, 1191, 1175, 1129. m.p.: 156.0–158.2° C. $^1$H-NMR (CDCl$_3$, ppm): 1.00–1.30(1H,m), 1.30–2.00(9H, m), 2.46 (3H,s), 3.14(2H,t,J=8.9 Hz), 3.89(2H,t,J=8.9 Hz), 5.22–5.38 (1H,m), 8.39(1H,s).

EXAMPLE 36

Preparation of Compound 29 (R$^1$: sec-butyl, R$^2$: methyl, R$^3$: trifluoroacetyl):

Compound 29 was obtained (yield: 58.5%) in the same manner as in Example 28 except that 8-sec-butyl-6,7-dihydro-5-methyl-8H-pyrrolo[3,2-e]pyrazolo[1,5-a]pyrimidine prepared from 7-chloro-6-(2-chloroethyl)-5-methylpyrazolo[1,5-a]pyrimidine and sec-butylamine was used.

IR (KBr tablet, cm$^{-1}$): 1675, 1630, 1600, 1515, 1245, 1225, 1180, 1155, 1125, 880, 775, 725. m.p.: 169.9–171.3° C. $^1$H-NMR (CDCl$_3$, ppm): 0.94(3H,t,J=7.6 Hz), 1.31(3H, d,J=7.0 Hz), 1.55–1.80(2H,m), 2.46(3H,s), 3.17(2H,t,J=8.9 Hz), 3.70–3.95(2H,m), 5.50–5.68(1H,m), 8.38(1H,s).

EXAMPLE 37

Preparation of ethyl 6-(2-hydroxyethyl)-5-methylpyrazolo[1,5-a]pyrimidin-7(4H)-one-3-carboxylate:

To 1.55 g (10.00 mmol) of ethyl 3-amino-pyrazole-4-carboxylate and 1.92 g (15.00 mmol) of α-acetyl-γ-butyrolactone were added 2 ml of anhydrous ethanol. While stirring at room temperature under a nitrogen atmosphere, 0.1 ml of a boron trifluoride methanol complex were added to the resultant mixture, and the mixture was then stirred for 15 minutes under the same conditions. After the mixture was allowed to stand for 2 hours and 35 minutes under the same conditions, ethanol was added, and solids deposited were collected by filtration, washed with ethanol and air-dried. The thus-obtained solids were suspended in 10.5 ml of water, and 1.03 g (10.2 mmol) of triethylamine were added thereto, and the mixture was stirred for 3 hours in an oil bath heated to 100° C. Thereafter, the reaction mixture was cooled with ice water and concentrated hydrochloric acid was added under stirring to adjust the pH of the mixture to about 4 (deposition of solids). After chloroform and water were added to the mixture, and the mixture was fully shaken, the chloroform layer was separated. The water layer was further extracted with chloroform. After all the chloroform layers were put together and dried over anhydrous sodium sulfate, the solvent was distilled off. The residue was subjected to column chromatography on silica gel (chloroform, chloroform:methanol=100:1) to obtain 2.11 g (yield: 79.6%) of the intended product.

IR (KBr tablet, cm$^{-1}$): 3491, 3301, 1695, 1666, 1580, 1233, 1215, 1035, 778. $^1$H-NMR (CDCl$_3$, ppm): 1.39(3H, t,J=7.3 Hz), 2.50(3H,s), 2.88(2H,t,J=6.2 Hz), 3.88(2H,t,J= 6.2 Hz), 4.35(2H,q,J=7.3 Hz), 7.27(1H,s), 9.53(1H,brs).

EXAMPLE 38

Preparation of ethyl 7-chloro-6-(2-chloroethyl)-5-methylpyrazolo[1,5-a]pyrimidine-3-carboxylate:

To 0.34 g (1.28 mmol) of ethyl 6-(2-hydroxyethyl)-5-methylpyrazolo[1,5-a]pyrimidin-7(4H)-one-3-carboxylate were successively added 0.4 ml (d=1.645, 4.29 mmol) of phosphorus oxychloride and 0.36 ml (d=0.726, 2.59 mmol) of triethylamine. The mixture was then stirred for 2 hours and 15 minutes in an oil bath heated to 100° C. under a nitrogen atmosphere. Thereafter, the reaction mixture was cooled with ice water and dissolved in 10 ml of chloroform, and the solution was poured into 30 ml of ice water. After the pH of the mixture was adjusted to about 6 with a saturated aqueous solution of sodium hydrogencarbonate, and the thus-treated mixture was fully shaken, the organic layer was separated. The water layer was further extracted with chloroform (10 ml×2). After all the organic layers were put together and dried over anhydrous sodium sulfate, the solvent was distilled off. The residue was subjected to column chromatography on silica gel (chloroform) to obtain 0.33 g (yield: 84.6%) of the intended product.

$^1$H-NMR (CDCl$_3$, ppm): 1.42(3H,t,J=7.3 Hz), 2.83(3H,s), 3.38(2H,t,J=7.2 Hz), 3.78(2H,t,J=7.2 Hz), 4.42(2H,q,J=7.3 Hz), 8.57(1H,s).

EXAMPLE 39

Preparation of ethyl 8-cyclopentyl-6,7-dihydro-5-methyl-8H-pyrrolo[3,2-e]pyrazolo[1,5-a]pyrimidine-3-carboxylate (Compound 30):

To a solution of 0.12 g (0.40 mmol) of ethyl 7-chloro-6-(2-chloroethyl)-5-methyl-pyrazolo[1,5-a]pyrimidine-3-carboxylate in 1.6 ml of anhydrous dimethylformamide were successively added 0.04 g (0.47 mmol) of cyclopentylamine and 0.12 g (1.19 mmol) of triethylamine, and the mixture was stirred at room temperature for 17.5 hours. Thereafter, the reaction mixture was poured into 50 ml of water and extracted with chloroform (10 ml×3). All the chloroform layers were put together and dried over anhydrous sodium sulfate, and the solvent was then distilled off. The residue was subjected to column chromatography on silica gel (chloroform) to obtain 0.10 g (yield: 80.0%) of the intended product.

m.p.: 178–180° C. IR (KBr tablet, cm$^{-1}$): 1688, 1610, 1514, 1459, 1313, 1295, 1180, 1110, 776. $^1$H-NMR (CDCl$_3$, ppm): 1.39(3H,t,J=7.3 Hz), 1.60–1.85(6H,m), 1.85–2.05 (2H,m), 2.43(3H,s), 3.11(2H,t,J=9.0 Hz), 3.84(2H,t,J=9.0 Hz), 4.37(2H,q,J=7.3 Hz), 5.85–6.00(1H,m), 8.34(1H,s).

EXAMPLE 40

Preparation of Compound 31 ($R^1$: tert-butyl, $R^2$: methyl, $R^3$: ethoxycarbonyl):

Compound 31 was obtained in an amount of 0.57 g (yield: 57%) in the same manner as in Example 35 except that 1 g of 7-chloro-6-(2-chloroethyl)-3-ethoxycarbonyl-5-methylpyrazolo[1,5-a]pyrimidine and 3.2 ml of tertbutylamine were used.

IR (KBr tablet, cm$^{-1}$): 1708, 1600, 1570, 1176. m.p.:164–165° C. $^1$H-NMR (CDCl$_3$, ppm): 1.34(3H,t,J=7.0 Hz), 1.69(9H,s), 2.47(3H,s), 3.00(2H,t,J=8.9 Hz), 4.00(2H, t,J=8.9 Hz), 4.36(2H,q,J=7.0 Hz), 8.35(1H,s).

EXAMPLE 41

Preparation of Compound 32 ($R^1$: tert-amyl, $R^2$: methyl, $R^3$: ethoxycarbonyl):

Compound 32 was obtained in an amount of 0.89 g (yield: 58.9%) in the same manner as in Example 35 except that 1.45 g of 7-chloro-6-(2-chloroethyl)-3-ethoxycarbonyl-5-methylpyrazolo[1,5-a]pyrimidine and 5 ml of tertamylamine were used.

IR (KBr tablet, cm$^{-1}$): 1705, 1600, 1507, 1174. m.p.: 137–139° C. $^1$H-NMR (CDCl$_3$, ppm): 0.86(3H,t,J=7.6 Hz), 1.38(3H,t,J=7.0 Hz), 1.63(6H,s), 2.30(2H,q,J=7.6 Hz), 2.42 (3H,s), 3.00(2H,t,J=8.9 Hz), 4.01(2H,t,J=8.9 Hz), 4.36(2H, q,J=7.0 Hz), 8.33(1H,s).

EXAMPLE 42

Preparation of Compound 33 ($R^1$: cyclopentyl, $R^2$: methyl, $R^3$: carboxyl):

In 13 ml of ethanol were suspended 0.90 g of Compound 30, and a solution of 0.84 g of sodium hydroxide in 6.5 ml of water was added to the suspension. The mixture was stirred at 100° C. for 30 minutes under a nitrogen atmosphere. While cooling with ice water and stirring, 13 ml of water was added to the mixture, and 1N hydrochloric acid was added to adjust the pH of the mixture to 2. Furthermore, a saturated aqueous solution of sodium hydrogencarbonate was added to adjust the pH of the mixture to 3–4. Solids deposited were collected by filtration, washed with water and air-dried to obtain 0.75 g (yield: 91.5%) of Compound 33.

IR (KBr tablet, cm$^{-1}$): 1723, 1610, 1516, 1301, 1202, 1191, 778. m.p.: 230–230.5° C. $^1$H-NMR (CDCl$_3$, ppm): 1.60–1.88(6H,m), 1.88–2.10(2H,m), 2.34(3H,s), 3.14(2H,t, J=9.2 Hz), 3.91(2H,t,J=9.2 Hz), 5.78–5.95(1H,m), 8.36(1H, s).

EXAMPLE 43

Preparation of Compound 34 ($R^1$: tert-butyl, $R^2$: methyl, $R^3$: carboxyl):

Compound 34 was obtained in an amount of 0.64 g (yield: quantitative) by the treatment of 0.70 g of Compound 31 in the same manner as in Example 38.

IR (KBr tablet, cm$^{-1}$): 1718, 1584, 1508, 1203. m.p.: 258–259° C. $^1$H-NMR (DMSO-d$_6$, ppm): 1.67(9H,s), 2.31 (3H,s), 2.99(2H,t,J=8.9 Hz), 4.08(2H,t,J=8.9 Hz), 8.39(1H, s).

EXAMPLE 44

Preparation of Compound 35 ($R^1$: tert-amyl, $R^2$: methyl, $R^3$: carboxyl):

Compound 35 was obtained in an amount of 0.41 g (yield: 89.7%) by the treatment of 0.5 g of Compound 32 in the same manner as in Example 38.

IR (KBr tablet, cm$^{-1}$): 1723, 1578, 1504, 1186. m.p.: 239–240° C. $^1$H-NMR (DMSO-d$_6$, ppm): 0.89(3H,t,J=7.3 Hz), 1.73(6H,s), 2.30(2H,q,J=7.3 Hz), 2.36(3H,s), 3.04(2H, t,J=8.9 Hz), 4.08(2H,t,J=8.9 Hz), 8.38(1H,s).

EXAMPLE 45

Preparation of Compound 36 ($R^1$: cyclopentyl, $R^2$: methyl, $R^3$: N-(1H-tetrazol-5-yl)carbamoyl):

In 2 ml of anhydrous DMF were suspended 0.286 g of Compound 33. While stirring at room temperature under a nitrogen atmosphere, 0.20 g of 1,1'-carbonyldiimidazole as remained solid were added to the suspension, and the resultant mixture was stirred for 15 minutes at room temperature and for 40 minutes at 90° C. To the reaction mixture, were added 0.12 g of 5-amino-1H-tetrazole, and the mixture was stirred for 1.5 hours. While cooling with ice water, 10 ml of water were added, and 1N hydrochloric acid was added with stirring to adjust the pH of the reaction mixture to 1. A saturated aqueous solution of sodium hydrogencarbonate was then added to adjust the pH of the reaction mixture to 4. Solids deposited were collected by filtration, washed with water and air-dried to obtain 0.315 g (yield: 89.2%) of Compound 36.

IR (KBr tablet, cm$^{-1}$): 1676, 1605, 1543, 1508, 1297, 1200, 1186, 764. m.p.: 293–296° C. $^1$H-NMR (CDCl$_3$, ppm): 1.68–1.88(6H,m), 1.90–2.08(2H,m), 2.45(3H,s), 3.17 (3H,t,J=9.2 Hz), 3.93(3H,t,J=9.2 Hz), 5.80–5.95(1H,m), 8.52(1H,s).

EXAMPLE 46

Preparation of 1-bromo-2-t-butyldimethylsilyloxyethane:

To 40 ml of acetonitrile dried over molecular sieves were added 3.50 g of t-butyldimethylsilyl chloride and 4.00 g of imidazole. After the mixture was stirred for 10 minutes at room temperature, 2.64 g of 2-bromoethanol was added to the mixture. The mixture was further stirred for 6 hours at room temperature. The solvent was distilled off under reduced pressure, and ethyl acetate was added to the residue. After the ethyl acetate layer was washed with a saturated aqueous solution of sodium hydrogencarbonate and dried over anhydrous sodium carbonate, the solvent was distilled off under reduced pressure. The thus-obtained crude product was subjected to column chromatography on silica gel (elution solvent: hexane:ethyl acetate=2:1) to obtain 4.40 g (yield: 87.0%) of the intended product. Colorless liquid.

$^1$H-NMR (CDCl$_3$, ppm): −0.10(6H,s), 0.82(9H,s), 3.31 (2H,t,J=6.3 Hz), 3.80(2H,t,J=6.3 Hz).

EXAMPLE 47

Preparation of diethyl 2-(2-t-butyldimethylsilyloxy-ethyl) malonate:

In 1.70 liters of ethanol dried over molecular sieves were added 22.90 g of metal sodium. To the solution, were added 131.0 g of diethyl malonate and 230 g of the compound prepared in Example 46. The mixture was stirred overnight while heating under reflux. After most of the solvent was distilled off under reduced pressure, a small amount of ether was added. Crystals deposited were separated by filtration, and the filtrate was concentrated and subjected to column chromatography on silica gel (elution solvent: hexane along→hexane:ethyl acetate=10:1) to obtain 234.42 g (yield: 89.9%) of the intended product. Colorless liquid.

$^1$H-NMR (CDCl$_3$, ppm): 0.02(6H,s), 0.87(9H,s), 1.25 (6H,t,J=7.2 Hz), 2.10(2H,q,J=6.5 Hz), 3.54–3.66(3H,m), 4.17(4H,m).

EXAMPLE 48

Preparation of 5-hydroxy-6-(2-hydroxyethyl)pyrazolo-[1,5-a]pyrimidin-7(4H)-one:

After 6.72 g of metal sodium were dissolved in 1,200 ml of ethanol dried over molecular sieves, 64.0 g of the compound prepared in Example 47 and 12.12 g of 3-aminopyrazole were added to the solution. The mixture was then stirred for 3 days while heating under reflux. The solvent was distilled off under reduced pressure, and water was added to the residue to dissolve it. The water layer was washed 3 times with ether. The water layer was cooled to 0° C., and its pH was adjusted to 5.0 with 1N hydrochloric acid. Crystals deposited were collected by filtration. To the crystals, were added 200 ml of methanol and 3 drops of concentrated hydrochloric acid. The solvent was distilled off under reduced pressure together with water. Crystals were deposited from a methanol/ether system to obtain 21.38 g (yield: 76.8%) of the intended product. Pale brown crystals.

$^1$H-NMR (DMSO-d$_6$, ppm): 2.66(2H,t,J=6.7 Hz), 3.52 (2H,t,J=6.7 Hz), 5.93(1H,d,J=1.9 Hz), 7.60(1H,d,J=1.9 Hz).

EXAMPLE 49

Preparation of 6-(2-chloroethyl)-5,7-dichloropyrazolo[1,5-a]pyrimidine:

To 12.45 g of 5-hydroxy-6-(2-hydroxyethyl)-pyrazolo[1,5-a]pyrimidin-7(4H)-one were added 100 ml of phosphorus oxychloride and 13.00 g of triethylamine. The mixture was stirred for 2 hours while heating under reflux. After excess phosphorus oxychloride was distilled off under reduced pressure, the residue was poured into ice water and extracted with chloroform. After the chloroform layer was washed with water and then dried over anhydrous sodium sulfate, the solvent was distilled off. The residue was subjected to column chromatography on silica gel (chloroform) to obtain 10.86 g (yield: 68.0%) of the intended product. Pale brown crystals.

$^1$H-NMR (CDCl$_3$, ppm): 3.49(2H,t,J=7.0 Hz), 3.82(2H,t, J=7.0 Hz), 6.80(1H,d,J=2.4 Hz), 8.21(1H,d,J=2.4 Hz).

EXAMPLE 50

Preparation of 6-(2-chloroethyl)-5,7-dichloro-3-nitropyrazolo[1,5-a]pyrimidine:

To 100 ml of concentrated sulfuric acid cooled to 0° C. with ice water, were added 50 ml of 90% nitric acid gradually so as not to raise the temperature. After the resultant mixed acid was stirred for a while, 13.80 g of the compound prepared in Example 49 as remained crystals were added gradually so as not to raise the temperature also. The resultant mixture was stirred for 4 hours while maintaining the temperature at 0° C. Since spots attributable to the raw materials on TLC disappeared, the stirring was stopped, and the reaction mixture was poured into ice water. Crystals deposited were collected by filtration and air-dried to obtain 15.61 g (yield: 95.5%) of the intended product. Yellow crystals.

$^1$H-NMR (CDCl$_3$, ppm): 3.55(2H,t,J=7.0 Hz), 3.89(2H,t, J=7.0 Hz), 8.84(1H,s).

EXAMPLE 51

Preparation of 8-t-butyl-5-chloro-6,7-dihydro-3-nitro-8H-pyrrolo[3,2-e]pyrazolo[1,5-a]pyrimidine (Compound 40):

In 50 ml of anhydrous dimethylformamide were dissolved 6.00 g of the compound prepared in Example 50, and 1.80 g of t-butylamine and 4.10 g of triethylamine were added to the solution. After the mixture was stirred for 4 hours at room temperature and then concentrated under reduced pressure, the residue was dissolved in chloroform. After the solution was washed with diluted hydrochloric acid and a saturated saline solution and dried over anhydrous sodium sulfate, the solvent was distilled off. The residue was treated with a chloroform-ether system to deposit crystals to obtain 5.54 g (yield: 92.3%) of the intended product. Yellow crystals.

m.p.: 247° C. (decomposed). IR (KBr tablet, cm$^{-1}$): 1610, 1580, 1480. $^1$H-NMR (CDCl$_3$, ppm): 1.78(9H,s), 3.13(2H, t,J=8.9 Hz), 4.15(2H,t,J=8.9 Hz), 8.61(1H,s).

EXAMPLE 52

Preparation of 5-chloro-8-cyclopentyl-6,7-dihydro-3-nitro-8H-pyrrolo[3,2-e]pyrazolo[1,5-a]pyrimidine (Compound 41):

Synthesis was performed by the reaction of 6.00 g of the compound prepared in Example 51 with 5.59 g of cyclopentylamine and 4.10 g of triethylamine in accordance with the synthetic process in Example 43 to obtain 5.59 g (yield: 89.2%) of the intended product. Yellow crystals.

m.p.: 209–210° C. IR (KBr tablet, cm$^{-1}$): 1610, 1480, 1230. $^1$H-NMR (CDCl$_3$, ppm): 1.76(6H,m), 2.04(2H,m), 3.26(2H,t,J=7.8 Hz), 3.86(2H,t,J=7.8 Hz), 5.79(1H,m), 8.57 (1H,s).

EXAMPLE 53

Preparation of 8-sec-butyl-5-chloro-6,7-dihydro-3-nitro-8H-pyrrolo[3,2-e]pyrazolo[1,5-a]pyrimidine (Compound 42):

Synthesis was performed by the reactione of 6.00 g of the compound prepared in Example 42 with 1.80 g of secbutylamine and 4.10 g of triethylamine in accordance with the synthetic process in Example 43 to obtain 5.50 g (yield: 91.7%) of the intended product. Yellow crystals.

m.p.: at least 270° C. IR (KBr tablet, cm$^{-1}$): 1630, 1610, 1490, 1230, 1220. $^1$H-NMR (CDCl$_3$, ppm): 0.95(3H,t,J=7.0 Hz), 1.34(3H,d,J=7.0 Hz), 1.68(2H,m), 3.24(2H,t,J=8.9 Hz), 3.89(1H,m), 5.58(1H,m), 8.58(1H,s).

EXAMPLE 54

Preparation of 8-tert-butyl-5-chloro-6,7-dihydro-8H-pyrrolo[3,2-e]pyrazolo[1,5-a]pyrimidine:

In 70 ml of dimethylformamide were dissolved 12.50 g of 6-(2-chloroethyl)-5,7-dichloropyrazolo[1,5-a]pyrimidine, and 9.55 g of tert-butylamine and 11.47 g of triethylamine were added to the solution. The mixture was stirred for 2 days at room temperature. Excess amines and the solvent were distilled off under reduced pressure, and the residue was dissolved in chloroform. After the chloroform layer was washed with a saturated saline solution and dried over anhydrous sodium sulfate, the solvent was distilled off. The residue was treated with a chloroform-ether system to deposit crystals. The crystals were collected by filtration and recrystallized from ethanol to obtain 11.34 g (yield: 90.6%) of the intended product. White crystals.

$^1$H-NMR (CDCl$_3$, ppm): 1.79(9H,s), 3.06(2H,t,J=7.2 Hz), 4.00(2H,t,J=7.2 Hz), 6.31(1H,d,J=2.4 Hz), 7.95(1H,d,J=2.4 Hz).

EXAMPLE 55

Preparation of 5-chloro-8-cyclopentyl-6,7-dihydro-8H-pyrrolo[3,2-e]pyrazolo[1,5-a]pyrimidine:

Synthesis was performed by the reaction of 11.0 g of 6-(2-chloroethyl)-5,7-dichloropyrazolo[1,5-a]pyrimidine with 1.80 g of cyclopentylamine and 8.87 g of triethylamine in accordance with the synthetic process in Example 54 to obtain 10.42 g (yield: 90.4%) of the intended product. White crystals.

$^1$H-NMR (CDCl$_3$, ppm): 1.70(6H,m), 2.10(2H,m), 3.15 (2H,t,J=6.2 Hz), 3.85(2H,t,J=6.2 Hz), 6.04(1H,m), 6.30(1H, d,J=2.4 Hz), 7.95(1H,d,J=2.4 Hz).

EXAMPLE 56

Preparation of 8-sec-butyl-5-chloro-6,7-dihydro-8H-pyrrolo[3,2-e]pyrazolo[1,5-a]pyrimidine:

Synthesis was performed by the reaction of 5.26 g of 6-(2-chloroethyl)-5,7-dichloropyrazolo[1,5-a]pyrimidine with 4.00 g of sec-butylamine and 4.82 g of triethylamine in accordance with the synthetic process in Referential Example 9 to obtain 4.68 g (yield: 89.0%) of the intended product. White crystals.

$^1$H-NMR (CDCl$_3$, ppm): 0.97(3H,t,J=7.3 Hz), 1.29(3H, d,J=7.0 Hz), 1.69(2H,m), 3.20(2H,t,J=6.2 Hz), 3.80(2H,m), 5.73(1H,m), 6.30(1H,d,J=1.9 Hz), 7.94(1H,d,J=1.9 Hz).

EXAMPLE 57

Preparation of 8-tert-butyl-6,7-dihydro-8H-pyrrolo[3,2-e] pyrazolo[1,5-a]pyrimidine:

In a mixed solvent of 300 ml of tetrahydrofuran and 150 ml of methanol were dissolved 11.30 g of 8-tert-butyl-5-chloro-6,7-dihydro-8H-pyrrolo[3,2-e]pyrazolo-[1,5-a] pyrimidine, and the reaction system was cooled to 0° C. To the solution were gradually added 3.75 g of palladium chloride and 7.83 g of sodium borohydride, and the mixture was stirred for 30 minutes at 0° C. Furthermore, 7.50 g of palladium chloride and 5.66 g of sodium borohydride were gradually added, and the resultant mixture was stirred for 30 minutes at 0° C. and for 2 hours at room temperature. The reaction solvent was distilled off under reduced pressure, and the resultant crude product was subjected to column chromatography on silica gel (ethyl acetate→ethyl acetate:methanol=10:1) to obtain 3.94 g (yield: 40.4%) of the intended product. White crystals.

$^1$H-NMR (CDCl$_3$, ppm): 1.74(9H,s), 3.04(2H,t,J=8.9 Hz), 3.96(2H,t,J=8.9 Hz), 6.37(1H,d,J=2.2 Hz), 7.94(1H,s), 7.96 (1H,d,J=2.2 Hz).

EXAMPLE 58

Preparation of 8-cyclopentyl-6,7-dihydro-8H-pyrrolo-[3, 2-e]pyrazolo[1,5-a]pyrimidine:

The intended product was obtained in an amount of 3.44 g (yield: 38.0%) in the same manner as in Referential Example 12 except that 10.42 g of 5-chloro-8-cyclopentyl-6,7-dihydro-8H-pyrrolo[3,2-e]pyrazolo[1,5-a]pyrimidine were used. White crystals.

$^1$H-NMR (CDCl$_3$, ppm): 1.75(6H,m), 1.98(2H,m), 3.16 (2H,t,J=8.9 Hz), 3.85(2H,t,J=8.9 Hz), 6.05(1H,m), 6.31(1H, d,J=2.4 Hz), 7.98(1H,s), 7.98(1H,d,J=2.4 Hz).

EXAMPLE 59

Preparation of 8-sec-butyl-6,7-dihydro-8H-pyrrolo-[3,2-e]pyrazolo[1,5-a]pyrimidine:

The intended product was obtained in an amount of 1.23 g (yield: 30.4%) in the same manner as in Referential Example 12 except that 4.68 g of 8-sec-butyl-5-chloro-6,7-dihydro-8H-pyrrolo[3,2-e]pyrazolo[1,5-a]pyrimidine were used. White crystals.

$^1$H-NMR (CDCl$_3$, ppm): 0.94(3H,t,J=7.6 Hz), 1.27(3H, d,J=6.5 Hz), 1.63(2H,m), 3.17(2H,t,J=8.9 Hz), 3.75(2H,m), 5.73(1H,m), 6.37(1H,d,J=2.4 Hz), 7.96(1H,s), 7.96(1H,d,J= 2.4 Hz).

EXAMPLE 60

Preparation of 8-tert-butyl-6,7-dihydro-3-nitro-8H-pyrrolo[3,2-e]pyrazolo[1,5-a]pyrimidine (Compound 37):

After 3.30 ml of 90% nitric acid were gradually added to 20 ml of acetic acid, 3 drops of sulfuric acid were added, and the mixture was stirred at room temperature for a while. A solution of 3.90 g of 8-tert-butyl-6,7-dihydro-8H-pyrrolo[3,2-e]pyrazolo[1,5-a]pyrimidine in 8.0 ml of acetic acid was gradually added to the mixed acid. Since spots attributable to the raw materials on TLC disappeared, the stirring was stopped, and the reaction mixture was poured into ice water and extracted with chloroform. The chloroform layer was washed with a saturated saline solution and then dried over anhydrous sodium sulfate, and the solvent was distilled off under reduced pressure. Crystals were deposited from a chloroform/ether system, collected by filtration and recrystallized from ethanol to purify them, and 2.32 g (yield: 49.0%) of the intended product were obtained. Yellow crystals.

m.p. 209° C. IR (KBr tablet, $cm^{-1}$): 1620, 1590, 1490, 1400. $^1$H-NMR ($CDCl_3$, ppm): 1.73(9H,s), 3.16(2H,t,J=8.9 Hz), 4.12(2H,t,J=8.9 Hz), 8.17(1H,s), 8.61(1H,s).

EXAMPLE 61

Preparation of 8-cyclopentyl-6,7-dihydro-3-nitro-8H-pyrrolo[3,2-e]pyrazolo[1,5-a]pyrimidine (Compound 38):

The intended product was obtained in an amount of 2.57 g (yield: 56.0%) in the same manner as in Example 60 except that 3.40 g of 8-cyclopentyl-6,7-dihydro-8H-pyrrolo[3,2-e]pyrazolo[1,5-a]pyrimidine were used. Yellow crystals.

m.p.: 181° C. IR (KBr tablet, $cm^{-1}$): 1620, 1610, 1480, 1245, 1220. $^1$H-NMR ($CDCl_3$, ppm): 1.75(6H,m), 2.05(2H,m), 3.29(2H,t,J=8.4 Hz), 4.06(2H,t,J=8.4 Hz), 5.83(1H,m), 8.14(1H,s), 8.60(1H,s).

EXAMPLE 62

Preparation of 8-sec-butyl-6,7-dihydro-3-nitro-8H-pyrrolo[3,2-e]pyrazolo[1,5-a]pyrimidine (Compound 39):

The intended product was obtained in an amount of 190 mg (yield: 65.5%) in the same manner as in Example 46 except that 240 mg of 8-sec-butyl-6,7-dihydro-8H-pyrrolo[3,2-e]pyrazolo[1,5-a]pyrimidine were used. Yellow crystals.

m.p.: 199° C. IR (KBr tablet, $cm^{-1}$): 1630, 1610, 1480, 1250, 1220. $^1$H-NMR ($CDCl_3$, ppm): 0.95(3H,t,J=7.3 Hz), 1.33(3H,d,J=6.8 Hz), 1.73(2H,m), 3.27(2H,t,J=9.2 Hz), 3.87 (2H,m), 5.62(1H,m), 8.18(1H,s), 8.62(1H,s).

EXAMPLE 63

Preparation of 8-sec-butyl-6,7-dihydro-5-hydroxymethyl-3-nitro-8H-pyrrolo[3,2-e]pyrazolo[1,5-a]pyrimidine (Compound 53):

In 10 ml of anhydrous tetrahydrofuran were suspended 330 mg of Compound 24. While cooling the reaction system in an ice-salt bath and stirring under a nitrogen atmosphere, 0.17 ml of triethylamine were added to the suspension. Furthermore, a solution of 0.12 ml of ethyl chlorocarbonate in 2 ml of anhydrous tetrahydrofuran was added dropwise to the mixture over 1 minute, and the mixture was stirred for 40 minutes. Then, 100 mg of sodium borohydride were added at once to the reaction system, and the resultant mixture was stirred at room temperature for 1 hour. An additional 50 mg of sodium borohydride was added, and the resultant mixture was stirred for 1 hour under cooling with ice water. 1N hydrochloric acid was gradually added at the same temperature to adjust the pH of the reaction mixture to 1–2. A saturated aqueous solution of sodium hydrogencarbonate was added to the reaction mixture to weakly alkalize it. After 10 ml of water were added to the reaction mixture, it was extracted with ethyl acetate. The organic layer was washed with a saturated saline solution and then dried over anhydrous sodium sulfate, and the solvent was distilled off under reduced pressure. After the water layer was extracted again with chloroform, and the extract was dried over anhydrous sodium sulfate, the solvent was distilled off under reduced pressure. Crude products obtained from both organic layers were put together and subjected to column chromatography on silica gel (elution solvent: chloroform:methanol=100:0.5) to obtain 40 mg (yield: 12.7%) of the intended product. Yellow crystals.

IR (KBr tablet, $cm^{-1}$): 3421, 1623, 1489, 1241. m.p.: 222–226° C. $^1$H-NMR ($CDCl_3$, ppm): 0.94(3H,t,J=7.3 Hz), 1.33(3H,d,J=6.5 Hz), 1.65(2H,m), 3.19(2H,t,J=8.9 Hz), 3.87 (2H,m), 4.65(2H,s), 5.60(1H,m), 8.56(1H,s).

EXAMPLE 64

Preparation of 8-sec-butyl-5-carbamoyl-6,7-dihydro-3-nitro-8H-pyrrolo[3,2-e]pyrazolo[1,5-a]pyrimidine (Compound 75):

In 6 ml of anhydrous tetrahydrofuran were suspended 0.19 g of Compound 24. While cooling the reaction system in an ice-salt bath and stirring under a nitrogen atmosphere, 0.11 ml of triethylamine were added to the suspension. Furthermore, a solution of 0.08 ml of ethyl chlorocarbonate in 2 ml of anhydrous tetrahydrofuran was added dropwise to the mixture over 2 minutes, and the mixture was stirred for 40 minutes under the same conditions. Under the same conditions, 1.8 ml of concentrated aqueous ammonia were then added at once, and the mixture was vigorously stirred for 1 hour. Crystals deposited were collected by filtration and air-dried. After the thus-obtained crystals were dissolved once in a 4:1 mixed solvent of chloroform and methanol, and insoluble matter was removed by filtration, the solution was concentrated under reduced pressure. Hexane was added to the concentrate, and crystals were reprecipitated to obtain 150 mg (yield: 78.9%) of the intended product. Yellowish green crystals.

IR (KBr tablet, $cm^{-1}$): 3432, 1697, 1490, 1236. m.p.: at least 300° C. $^1$H-NMR (DMSO-$d_6$, ppm): 0.93(3H,t,J=7.3 Hz), 1.34(3H,d,J=6.5 Hz), 1.73(2H,m), 3.53(2H,t,J=8.6 Hz), 4.00(2H,m), 5.60(1H,m), 7.83(1H,brs), 7.93(1H,brs), 8.99 (1H,s).

EXAMPLE 65

Preparation of ethyl 8-cylcopropyl-6,7-dihydro-3-nitro-8H-pyrrolo[3,2-e]pyrazolo[1,5-a]pyrimidine-5-carboxylate (Compound 76):

The intended product was obtained (yield: 97.6%) in the same manner as in Example 27 except that cyclopropylamine was used instead of cylcopentylamine.

$^1$H-NMR ($CDCl_3$, ppm): 1.00–1.09(4H,m), 1.42(3H,t,J=7.0 Hz), 3.50(2H,t,J=8.9 Hz), 3.70(1H,m), 3.95(2H,t,J=8.9 Hz), 4.42(2H,q,J=7.0 Hz), 8.72(1H,s).

EXAMPLE 66

Preparation of ethyl 8-cyclobutyl-6,7-dihydro-3-nitro-8H-pyrrolo[3,2-e]pyrazolo[1,5-a]pyrimidine-5-carboxylate (Compound 77):

The intended product was obtained (yield: 99.8%) in the same manner as in Example 27 except that cyclobutylamine was used instead of cylcopentylamine.

$^1$H-NMR (CDCl$_3$, ppm): 1.46(3H,t,J=6.8 Hz), 1.84(2H, m), 2.38(4H,m), 3.59(2H,t,J=8.6 Hz), 4.13(2H,t,J=8.6 Hz), 4.45(2H,q,J=6.8 Hz), 6.05(1H,m), 8.67(1H,s).

EXAMPLE 67

Preparation of ethyl 6,7-dihydro-8-isopropyl-3-nitro-8H-pyrrolo[3,2-e]pyrazolo[1,5-a]pyrimidine-5-carboxylate (Compound 78):

The intended product was obtained (yield: 97.1%) in the same manner as in Example 27 except that isopropylamine was used instead of cylcopentylamine.

$^1$H-NMR (CDCl$_3$, ppm): 1.40(6H,d,J=7.0 Hz), 1.47(3H, t,J=7.0 Hz), 3.56(2H,t,J=8.9 Hz), 3.99(2H,t,J=8.9 Hz), 4.45 (2H,q,J=7.0 Hz), 5.89(1H,m), 8.65(1H,s).

EXAMPLE 68

Preparation of ethyl 6,7-dihydro-8-(1-ethylpropyl)-3-nitro-8H-pyrrolo[3,2-e]pyrazolo[1,5-a]pyrimidine-5-carboxylate (Compound 79):

The intended product was obtained (yield: 96.4%) in the same manner as in Example 27 except that 3-aminopentane was used instead of cylcopentylamine.

1H-NMR (CDCl$_3$, ppm): 0.93(6H,t,J=7.3 Hz), 1.47(3H, t,J=7.3 Hz), 1.65–1.82(4H,m), 3.61(2H,t,J=8.6 Hz), 3.87 (2H,t,J=8.6 Hz), 4.46(2H,q,J=7.3 Hz), 5.61(1H,m), 8.67(1H, s).

EXAMPLE 69

Preparation of 8-cyclopropyl-6,7-dihydro-3-nitro-8H-pyrrolo[3,2-e]pyrazolo[1,5-a]pyrimidine-5-carboxylic acid (Compound 80):

Ethyl 8-cyclopropyl-6,7-dihydro-3-nitro-8H-pyrrolo-[3,2-e]-pyrazolo[1,5-a]pyrimidine-5-carboxylate was treated in the same manner as in Example 30 to obtain the intended product (yield: quantitative).

$^1$H-NMR (DMSO-d$_6$, ppm): 0.86–1.07(4H,m), 3.33(2H, t,J=8.9 Hz), 3.68(1H,m), 3.88(2H,t,J=8.9 Hz), 8.91(1H,s).

EXAMPLE 70

Preparation of 8-cyclobutyl-6,7-dihydro-3-nitro-8H-pyrrolo[3,2-e]pyrazolo[1,5-a]pyrimidine-5-carboxylic acid (Compound 81):

Ethyl 8-cyclobutyl-6,7-dihydro-3-nitro-8H-pyrrolo-[3,2-e]pyrazolo[1,5-a]pyrimidine-5-carboxylate was treated in the same manner as in Example 30 to obtain the intended product (yield: 94.1%).

$^1$H-NMR (DMSO-d$_6$, ppm): 1.78–1.86(2H,m), 2.30–2.46 (4H,m), 3.59(2H,t,J=8.4 Hz), 4.15(2H,t,J=8.4 Hz), 4.23(1H, brs), 6.04(1H,m), 8.68(1H,s).

EXAMPLE 71

Preparation of 6,7-dihydro-8-isopropyl-3-nitro-8H-pyrrolo[3,2-e]pyrazolo[1,5-a]pyrimidine-5-carboxylic acid (Compound 82):

Ethyl 6,7-dihydro-8-isopropyl-3-nitro-8H-pyrrolo-[3,2-e] pyrazolo[1,5-a]pyrimidine-5-carboxylate was treated in the same manner as in Example 30 to obtain the intended product (yield: 97.0%).

$^1$H-NMR (DMSO-d$_6$, ppm): 1.39(6H,d,J=7.0 Hz), 3.55 (2H,t,J=8.6 Hz), 4.01(2H,t,J=8.6 Hz), 5.86(1H,m), 8.69(1H, s).

EXAMPLE 72

Preparation of 6,7-dihydro-8-(1-ethylpropyl)-3-nitro-8H-pyrrolo[3,2-e]pyrazolo[1,5-a]pyrimidine-5-carboxylic acid (Compound 83):

Ethyl 6,7-dihydro-8-(1-ethylpropyl)-3-nitro-8H-pyrrolo [3,2-e]pyrazolo[1,5-a]pyrimidine-5-carboxylate was treated in the same manner as in Example 30 to obtain the intended product (yield: 97.3%).

$^1$H-NMR (DMSO-d$_6$, ppm): 0.93(6H,t,J=7.3 Hz), 1.59–1.86(4H,m), 3.67(2H,t,J=8.9 Hz), 3.93(2H,t,J=8.9 Hz), 5.63(1H,m), 8.68(1H,s).

EXAMPLE 73

Preparation of 5-amino-8-cyclopropyl-6,7-dihydro-3-nitro-8H-pyrrolo[3,2-e]pyrazolo[1,5-a]pyrimidine (Compound 84):

The intended product was prepared (yield: 74.4%) in accordance with the same process as in Example 23 except that 8-cyclopropyl-6,7-dihydro-3-nitro-8H-pyrrolo[3,2-e]-pyrazolo[1,5-a]pyrimidine-5-carboxylic acid was used as a raw material. The intended product thus obtained was recrystallized from chloroform-methanol-ether. Yellow crystals.

IR (KBr tablet, cm$^{-1}$): 1636, 1400, 1260. m.p.: at least 280° C. $^1$H-NMR (DMSO-d$_6$, ppm): 0.84(4H,m), 2.80(2H, t,J=8.9 Hz), 3.18(1H,m), 3.72(2H,t,J=8.9 Hz), 7.04(2H,brs), 8.51(1H,s).

EXAMPLE 74

Preparation of 5-amino-8-cyclobutyl-6,7-dihydro-3-nitro-8H-pyrrolo[3,2-e]pyrazolo[1,5-a]pyrimidine (Compound 85):

The intended product was prepared (yield: 54.1%) in accordance with the same process as in Example 23 except that 8-cyclobutyl-6,7-dihydro-3-nitro-8H-pyrrolo[3,2-e]-pyrazolo[1,5-a]pyrimidine-5-carboxylic acid was used as a raw material. The intended product thus obtained was recrystallized from chloroform-methanol-ether. Yellow crystals.

IR (KBr tablet, cm$^{-1}$): 1640, 1400, 1240. m.p.: at least 275° C. $^1$H-NMR (DMSO-d$_6$, ppm): 1.70(2H,m), 2.16(2H, m), 2.33(2H,m), 2.96(2H,t,J=9.2 Hz), 3.93(2H,t,J=9.2 Hz), 5.75(1H,m), 6.62(2H,bre), 8.37(1H,s).

EXAMPLE 75

Preparation of 5-amino-6,7-dihydro-8-isopropyl-3-nitro-8H-pyrrolo[3,2-e]pyrazolo[1,5-a]pyrimidine (Compound 86):

The intended product was prepared (yield: 48.9%) in accordance with the same process as in Example 23 except that 6,7-dihydro-8-isopropyl-3-nitro-8H-pyrrolo[3,2-e]-pyrazolo[1,5-a]pyrimidine-5-carboxylic acid was used as a raw material. The intended product thus obtained was recrystallized from chloroform-methanol-ether. Yellow crystals.

IR (KBr tablet, cm$^{-1}$): 1635, 1400, 1260. m.p.: at least 275° C. $^1$H-NMR (DMSO-d$_6$, ppm): 1.27(6H,d,J=6.2 Hz), 2.97(2H,t,J=9.5 Hz), 3.81(2H,t,J=9.5 Hz), 5.54(1H,m), 6.03 (2H,brs), 8.37(1H,s).

EXAMPLE 76

Preparation of 5-amino-6,7-dihydro -8-(1-ethyl-propyl)-3-nitro-8H-pyrrolo[3,2-e]pyrazolo[1,5-a]pyrimidine (Compound 87):

The intended product was prepared (yield: 48.5%) in accordance with the same process as in Example 23 except that 6,7-dihydro-8-(1-ethylpropyl)-3-nitro-8H-pyrrolo-[3,2-e]pyrazolo[1,5-a]pyrimidine-5-carboxylic acid was used as a raw material. The intended product thus obtained was recrystallized from chloroform-methanol-ether. Yellow crystals.

IR (KBr tablet, cm$^{-1}$): 1650, 1400, 1253. m.p.: 106–109° C. $^1$H-NMR (CDCl$_3$, ppm): 0.90(6H,t,J=7.3 Hz), 1.54–1.67 (4H,m), 3.00(2H,t,J=8.9 Hz), 3.75(2H,t,J=8.9 Hz), 5.35(1H, m), 5.78(2H,brs), 8.41(1H,s).

EXAMPLE 77

Preparation of 8-sec-butyl-5-diethylamino-6,7-dihydro-3-nitro-8H-pyrrolo[3,2-e]pyrazolo[1,5-a]pyrimidine (Compound 57):

To 400 mg of 8-sec-butyl-5-chloro-6,7-dihydro-3-nitro-8H-pyrrolo[3,2-e]pyrazolo[1,5-a]pyrimidine (Compound 42) were added 1.00 g of diethylamine, 1.00 g of triethylamine and 6.0 ml of dimethylformamide, and the mixture was stirred for 3 hours while heating under reflux. Since spots attributable to the raw materials on TLC disappeared, the stirring was stopped, and a part of the solvent was distilled off under reduced pressure. The remaining reaction mixture was poured into ice water, and crystals deposited were collected by filtration and air-dried. The thus-obtained crystals were further recrystallized from ethanol to obtain 410 mg (yield: 91.1%) of the intended product. Yellow crystals.

IR (KBr tablet, cm$^{-1}$): 1630, 1540, 1400, 1252. m.p.:174–175° C. $^1$H-NMR (CDCl$_3$, ppm): 0.92(3H,t,J=7.3 Hz), 1.20–1.30(8H,m), 1.52–1.68(2H,m), 3.26(2H,t,J=9.2 Hz), 3.62–3.73(6H,m), 5.43–5.56(1H,m), 8.41(1H,s).

EXAMPLE 78

Preparation of 8-sec-butyl-5-cyclobutylamino-6,7-dihydro-3-nitro-8H-pyrrolo[3,2-e]pyrazolo[1,5-a]pyrimidine (Compound 59):

In 6.0 ml of dimethylformamide were dissolved 400 mg of 8-sec-butyl-5-chloro-6,7-dihydro-3-nitro-8H-pyrrolo-[3,2-e]pyrazolo[1,5-a]pyrimidine (Compound 42). To the solution, were added 800 mg of cyclobutylamine and 800 mg of triethylamine, and the mixture was stirred for 4 hours at 130° C. Since spots attributable to the raw materials on TLC disappeared, the stirring was stopped, the reaction mixture was poured into ice water, and crystals deposited were collected by filtration and air-dried to obtain 120 mg (yield: 51.3%) of the intended product. The purification of the thus-obtained crystals was conducted by the subjection of them to column chromatography on silica gel (elution solvent: hexane:ethyl acetate=1:1) and the recrystallization of the product from a chloroform/ether system. Yellow crystals.

IR (KBr tablet, cm$^{-1}$): 3395, 1635, 1600, 1380, 1250. m.p.: 249–251° C. $^1$H-NMR (CDCl$_3$, ppm): 0.91(3H,t,J=7.3 Hz), 1.22(3H,d,J=6.5 Hz), 1.59(2H,m), 1.77(2H,m), 1.92 (2H,m), 2.48(2H,m), 2.96(2H,t,J=8.9 Hz), 3.73(2H,m), 4.73 (2H,m), 5.39(1H,m), 8.39(1H,s).

EXAMPLE 79

Preparation of 8-sec-butyl-6,7-dihydro-3-nitro-5-pyrrolidino-8H-pyrrolo[3,2-e]pyrazolo[1,5-a]pyrimidine (Compound 60):

To 400 mg of 8-sec-butyl-5-chloro-6,7-dihydro-3-nitro-8H-pyrrolo[3,2-e]pyrazolo[1,5-a]pyrimidine (Compound 42) were added 1.00 g of pyrrolidine, 1.00 g of triethylamine and 6.0 ml of dimethylformamide, and the mixture was stirred for 2 hours while heating under reflux. Since spots attributable to the raw materials on TLC almost disappeared, the stirring was stopped, and most of the solvent and excess amines were distilled off under reduced pressure. Chloroform and ether were added to the residue, and crystals deposited were collected by filtration and dried. The thus-obtained crystals were further recrystallized from ethanol to obtain 390 mg (yield: 87.4%) of the intended product. Yellow crystals.

IR (KBr tablet, cm$^{-1}$): 1633, 1540, 1394, 1256. m.p.: 237° C. $^1$H-NMR (CDCl$_3$, ppm): 0.94(3H,t,J=7.0 Hz), 1.24(3H, d,J=6.7 Hz), 1.52–1.68(2H,m), 1.96(4H,m), 3.36(2H,t,J=8.9 Hz), 3.56–3.69(2H,m), 3.78(4H,m), 5.45(1H,m), 8.37(1H, s).

EXAMPLE 80

Preparation of 8-sec-butyl-6,7-dihydro-3-nitro-5-piperidino-8H-pyrrolo[3,2-e]pyrazolo[1,5-a]pyrimidine (Compound 61):

To 200 mg of 8-sec-butyl-5-chloro-6,7-dihydro-3-nitro-8H-pyrrolo[3,2-e]pyrazolo[1,5-a]pyrimidine (Compound 42) were added 10 ml of piperidine, and the mixture was stirred for 1 hour while heating under reflux. Excess piperidine was distilled off under reduced pressure, and the residue was dissolved in chloroform. After the organic layer was washed with 1N hydrochloric acid and a saturated saline solution, and then dried over anhydrous sodium sulfate, the solvent was distilled off under reduced pressure. Crystals were deposited from a chloroform/ether system, collected by filtration and dried. The thus-obtained crystals were further recrystallized from ethanol to obtain 140 mg (yield: 60.9%) of the intended product. Yellow crystals.

IR (KBr tablet, cm$^{-1}$): 1638, 1398, 1230. m.p.: 182° C. $^1$H-NMR (CDCl$_3$, ppm): 0.92(3H,t,J=7.2 Hz), 1.21(3H,d,J= 6.5 Hz), 1.61–1.80(8H,m), 3.24(2H,t,J=9.5 Hz), 3.75(6H, m), 5.51(1H,m), 8.39(1H,s).

EXAMPLE 81

Preparation of 8-sec-butyl-6,7-dihydro-5-morpholino-3-nitro-8H-pyrrolo[3,2-e]pyrazolo[1,5-a]pyrimidine (Compound 62):

To 400 mg of 8-sec-butyl-5-chloro-6,7-dihydro-3-nitro-8H-pyrrolo[3,2-e]pyrazolo[1,5-a]pyrimidine (Compound 42) were added 4.0 ml of morpholine, and the mixture was stirred overnight while heating under reflux. Since little change was recognized on TLC, 4 ml of dimethylformamide and 1 ml of triethylamine were added to the mixture, and the resultant mixture was further stirred overnight while heating under reflux. Since spots attributable to the raw materials on TLC almost disappeared, the stirring was stopped, and the solvent and excess amines were distilled off under reduced pressure. The residue was dissolved in chloroform. After the organic layer was washed with 1N hydrochloric acid and a saturated saline solution, and then dried over anhydrous sodium sulfate, the solvent was distilled off under reduced pressure. Chloroform and ether were added to the residue, and crystals deposited were collected by filtration and further recrystallized from ethanol to obtain 260 mg (yield: 56.5%) of the intended product. Yellow crystals.

IR (KBr tablet, cm$^{-1}$): 1642, 1400, 1250. m.p.: 262° C.
$^1$H-NMR (CDCl$_3$, ppm): 0.92(3H,t,J=7.6 Hz), 1.23(3H,d,J= 7.0 Hz), 1.55–1.64(2H,m), 3.26(2H,t,J=9.2 Hz), 3.67–3.80 (10H,m), 5.43(1H,m), 8.41(1H,s).

EXAMPLE 82

Preparation of ethyl benzyloxyacetate:

4.42 g of sodium hydride (60% in oil) were washed twice with anhydrous ether, and then 80 ml of toluene were added to them. While cooling with ice water under a nitrogen atmosphere, a solution of 10.81 ml of benzylalcohol in 20 ml of toluene was added dropwise to the mixture over 25 minutes, and the mixture was stirred for 3.5 hours at room temperature. The reaction system was then cooled with ice water, to which a solution of 16.76 g of ethyl bromoacetate in 20 ml of toluene was added dropwise over 30 minutes. After being stirred for additional 25 minutes at 0° C., the reaction mixture was poured into a mixed solution of 400 ml of cold water and 2 ml of 5N hydrochloric acid, followed by extraction with benzene. The organic layer was washed with a saturated saline solution and then dried over anhydrous sodium sulfate, and the solvent was distilled off under reduced pressure. The resultant crude product was subjected to column chromatography on silica gel (elution solvent: hexane:ethyl acetate=15:1→12:1→10:1) to obtain 14.75 g (yield: 76.0%) of the intended product as a colorless oil.

$^1$H-NMR (CDCl$_3$, ppm): 1.30(3H,t,J=7.0 Hz), 4.09(2H,s), 4.22(2H,q,J=7.0 Hz), 4.64(2H,s), 7.30–7.42(5H,m).

EXAMPLE 83

Preparation of 2-benzyloxyacetyl-γ-butyrolactone:

A solution of 10.6 ml of diisopropylamine in 75 ml of tetrahydrofuran was chilled to −70° C., and 46 ml of a 1.6N hexane solution of n-butyllithium were added dropwise to the solution. After completion of the addition, the mixture was stirred for 15 minutes, and a solution of 54.8 g of γ-butyrolactone in 50 ml of tetrahydrofuran was added dropwise over 55 minutes, and the mixture was stirred for 50 minutes. Further, a solution of 14.75 g of ethyl benzyloxyacetate in 50 ml of tetrahydrofuran was added, and the resultant mixture was stirred for 2.5 hours at −60 to −50° C. 5N hydrochloric acid was then added so as not to exceed 20° C. to adjust the pH of the mixture to 1–2. Ethyl acetate was added to the reaction system, and the resultant mixture was washed with a saturated saline solution. The organic layer was dried over anhydrous sodium sulfate, and the solvent was distilled off under reduced pressure. The thus-obtained crude product was subjected to column chromatography on silica gel (elution solvent: hexane:ethyl acetate= 3:1→2:1→1:1) to obtain 13.01 g (yield: 87.2%) of the intended product as a colorless oil.

$^1$H-NMR (CDCl$_3$, ppm): 2.30(1H,m), 2.75(1H,m), 3.88 (1H,m), 4.27–4.47(4H,m), 4.68(2H,s), 7.29–7.38(5H,m).

EXAMPLE 84

Preparation of 3-{[2-(benzyloxy)-1-(tetrahydro-2-oxo-3-furyl)ethylidene]amino}pyrazole:

In 2.0 ml of ethanol were dissolved 1.83 g of 2-benzyloxyacetyl-γ-butyrolactone and 0.50 g of 3-aminopyrazole. To the solution, were added 60 μl of a boron trifluoride methanol complex, and the mixture was stirred for 16.5 hours at room temperature. The solvent was distilled off under reduced pressure, and the residue was subjected to column chromatography on silica gel (elution solvent: hexane:ethyl acetate=1:1→1:2) to obtain 1.18 g (yield: 65.5%) of the intended product as a yellow oil.

$^1$H-NMR (DMSO-d$_6$, ppm): 2.93(2H,t,J=7.8 Hz), 4.33 (2H,t,J=7.8 Hz), 4.42(2H,s), 4.52(2H,s), 6.06(1H,d,J=2.4 Hz), 7.29–7.37(5H,m), 7.44(1H,d,J=2.4 Hz), 9.96(1H,brs).

EXAMPLE 85

Preparation of 5-benzyloxymethyl-6-(2-hydroxyethyl) pyrazolo[1,5-a]pyrimidin-7(4H)-one:

To 1.18 g of 3-{[2-(benzyloxy)-1-(tetrahydro-2-oxo-3-furyl)ethylidene]amino}pyrazole were added 600 μl of triethylamine and 2.0 ml of water, and the mixture was stirred for 40 minutes while heating under reflux. After the reaction system was allowed to coom to room temperature, 1N hydrochloric acid was added to adjust the pH of the reaction mixture to 4. After the reaction mixture was extracted with chloroform, and the organic layer was dried over anhydrous sodium sulfate, the solvent was distilled off to obtain 1.18 g (yield: quantitative) of the intended product.

$^1$H-NMR (DMSO-d$_6$, ppm): 2.71(2H,t,J=5.7 Hz), 3.79 (2H,t,J=5.7 Hz), 4.64(2H,s), 4.67(2H,s), 6.01(1H,d,J=2.2 Hz), 7.30–7.38(5H,m), 7.74(1H,d,J=2.2 Hz).

EXAMPLE 86

Preparation of 5-benzyloxymethyl-7-chloro-6-(2-chloroethyl)pyrazolo[1,5-a]pyrimidine:

To 0.52 g of 5-benzyloxymethyl-6-(2-hydroxyethyl) pyrazolo[1,5-a]pyrimidin-7(4H)-one were added 4.0 ml of phosphorus oxychloride and 0.55 ml of triethylamine, and the mixture was stirred for 1 hour and 20 minutes in an oil bath heated to 100–110° C. Excess phosphorus oxychloride was distilled off under reduced pressure, and the residue was poured into ice water and extracted with chloroform. After the chloroform layer was dried over anhydrous sodium sulfate, the solvent was distilled off under reduced pressure. The thus-obtained crude product was subjected to column chromatography on silica gel (elution solvent: chloroform alone) to obtain 0.37 g (yield: 63.4%) of the intended product.

$^1$H-NMR (DMSO-d$_6$, ppm): 3.39(2H,t,J=7.3 Hz), 3.75 (2H,t,J=7.3 Hz), 4.65(2H,s), 4.77(2H,s), 6.79(1H,d,J=2.2 Hz), 7.30–7.37(5H,m), 8.19(1H,d,J=2.2 Hz).

EXAMPLE 87

Preparation of 7-chloro-6-(2-chloroethyl)-5-(2',4'-dinitrobenzyloxymethyl)-3-nitropyrazolo[1,5-a]pyrimidine:

To 4.0 ml of concentrated sulfuric acid cooled to 0° C., were gradually added 2.0 ml of 90% concentrated nitric acid so as not to raise the temperature. Under the same conditions, 0.37 g of 5-benzyloxymethyl-7-chloro-6-(2-chloroethyl)pyrazolo[1,5-a]pyrimidine were gradually added thereto, and the resultant mixture was stirred for 1 hour. Since spots attributable to the raw materials on TLC disappeared, the stirring was stopped, and the reaction mixture was poured into ice water. Crystals formed were collected by filtration, washed several times with water and dried to obtain 0.35 g (yield: 67.5%) of the intended product.

$^1$H-NMR (DMSO-d$_6$, ppm): 3.45(2H,t,J=7.6 Hz), 3.87 (2H,t,J=7.6 Hz), 5.14(2H,s), 5.19(2H,s), 8.20(1H,d,J=8.9 Hz), 8.60(1H,dd,J=8.9 Hz,2.4 Hz), 8.79(1H,d,J=2.4 Hz), 9.19(1H,s).

EXAMPLE 88

Preparation of 8-sec-butyl-6,7-dihydro-5-(2',4'-dinitrobenzyloxymethyl)-3-nitro-8H-pyrrolo[3,2-e]pyrazolo[1,5-a]pyrimidine (Compound 88):

In 5.0 ml of dimethylformamide were dissolved 0.35 g of 7-chloro-6-(2-chloroethyl)-5-(2',4'-dinitrobenzyloxymethyl)-3-nitropyrazolo[1,5-a]pyrimidine, and 0.18 g of sec-butylamine were added to the solution, and the mixture was stirred for 1.5 hours at room temperature. The solvent was distilled off under reduced pressure, and 50 ml of chloroform were added to the residue. The resultant solution was washed with 1N hydrochloric acid and a saturated saline solution. The organic layer was dried over anhydrous sodium sulfate, and the solvent was distilled off under reduced pressure. The thus-obtained crystals were recrystallized from a chloroform-ether system and air-dried. The crude product thus obtained was further subjected to preparative thin-layer chromatography (development solvent: chloroform:methanol=19:1) to obtain 0.14 g (yield: 40.0%) of the intended product.

Yellow crystals. IR (KBr tablet, cm$^{-1}$): 1624, 1225. m.p.:167–168° C. $^1$H-NMR (CDCl$_3$, ppm): 0.96(3H,t,J=7.3 Hz), 1.34(3H,d,J=6.5 Hz), 1.69(2H,m), 3.29(2H,t,J=8.9 Hz), 3.86(2H,m), 4.81(2H,s), 5.13(2H,s), 5.65(1H,m), 8.23(1H, d,J=8.4 Hz), 8.53(1H,dd,J=8.4 Hz,2.2 Hz), 8.62(1H,s), 8.92 (1H,d,J=2.2 Hz).

EXAMPLE 89

Preparation of ethyl 6-(2-hydroxyethyl)pyrazolo-[1,5-a]pyrimidin-7(4H)-one-5-carboxylate:

While stirring at room temperature, 1.00 g of synthetic zeolite A-4 powder were added to a solution of 1.00 g (12.03 mmol) of 3-aminopyrazole in 4 ml of acetic acid. Furthermore, a solution of 2.24 g (12.04 mmol) of ethyl (tetrahydro-2-oxo-3-furyl)glyoxylate in 5 ml of acetic acid was added dropwise over 2 minutes while cooling with ice water and stirring, and the mixture was stirred for 4 hours at room temperature. Thereafter, insoluble matter was removed by filtration, and the filtrate was concentrated under reduced pressure. The residue was dissolved in 20 ml of chloroform, and the solution was poured into 100 ml of water. The chloroform layer was separated, and the water layer was further extracted with chloroform (20 ml×2). After all the chloroform layers were put together and dried over anhydrous sodium sulfate, the solvent was distilled off. The residue was subjected to column chromatography on silica gel (chloroform) to obtain 0.66 g (yield: 21.9%) of the intended product.

$^1$H-NMR (CDCl$_3$, ppm): 1.16(3H,t,J=7.2 Hz), 3.09(2H,t, J=7.6 Hz), 4.22(2H,q,J=7.2 Hz), 4.41(2H,t,J=7.6 Hz), 5.94 (1H,d,J=2.4 Hz), 7.45(1H,d,J=2.4 Hz), 9.41(1H,s).

EXAMPLE 90

Preparation of ethyl 7-chloro-6-( 2-chloroethyl)pyrazolo [1,5-a]pyrimidine-5-carboxylate:

To 5.36 g (21.35 mmol) of ethyl 6-(2-hydroxyethyl)-pyrazolo-[1,5-a]pyrimidin-7(4H)-one-5-carboxylate were added 7 ml (d=1.645, 75.10 mmol) of phosphorus oxychloride, and the mixture was stirred for 40 minutes in an oil bath heated to 100° C. under a nitrogen atmosphere. The reaction mixture was then cooled to about room temperature, and 7 ml (d=0.726, 50.32 mmol) of triethylamine were added to the mixture. The resultant mixture was stirred for 30 minutes in the oil bath heated to 100° C. Thereafter, the reaction mixture was cooled with ice water, and 100 ml of chloroform were added thereto. The resultant mixture was poured into 600 ml of ice water. The chloroform layer was separated, and the water layer was extracted with chloroform (100 ml×2). After all the chloroform layers were put together and dried over anhydrous magnesium sulfate, the solvent was distilled off. The residue was subjected to column chromatography on silica gel (chloroform) to obtain 3.60 g (yield: 58.5%) of the intended product.

$^1$H-NMR (CDCl$_3$, ppm): 1.47(3H,t,J=7.2 Hz), 3.58(2H,t, J=7.4 Hz), 3.83(3H,t,J=7.4 Hz), 4.53(2H,q,J=7.2 Hz), 6.99 (1H,d,J=2.4 Hz), 8.30(1H,d,J=2.4 Hz).

EXAMPLE 91

Preparation of ethyl 8-cyclopentyl-6,7-dihydro-8H-pyrrolo[3,2-e]pyrazolo[1,5-a]pyrimidine-5-carboxylate:

In 48 ml of anhydrous dimethylformamide were dissolved 3.60 g (12.50 mmol) of ethyl 7-chloro-6-(2-chloro-ethyl)-pyrazolo[1,5-a]pyrimidine-5-carboxylate, and 7.3 ml (d=0.863, 73.99 mmol) of cyclopentylamine were added at once to the solution while stirring at room temperature under a nitrogen atmosphere, and the mixture was stirred for additional 1 hour and 20 minutes under the same conditions. The reaction mixture was then poured into 250 ml of ice water. Insoluble solids were collected by filtration, washed with water and air-dried to obtain 3.20 g (yield: 85.3%) of the intended product.

$^1$H-NMR (CDCl$_3$, ppm): 1.44(3H,t,J=7.3 Hz), 1.65–1.85 (6H,m), 1.88–2.08(2H,m), 3.51(2H,t,J=8.9 Hz), 3.88(2H,t, J=8.9 Hz), 4.46(2H,q,J=7.3 Hz), 6.08–6.22(1H,m), 6.57(1H, d,J=2.4 Hz), 8.04(1H,d,J=2.4 Hz).

EXAMPLE 92

Preparation of ethyl 8-sec-butyl-6,7-dihydro-8H-pyrrolo [3,2-e]pyrazolo[1,5-a]pyrimidine-5-carboxylate:

The intended product was obtained in an amount of 0.33 g (yield: 64.7%) in the same manner as in Example 91 except that 0.51 g of ethyl 7-chloro-6-(2-chloroethyl)-pyrazolo[1,5-a]pyrimidine-5-carboxylate and 1.1 ml of sec-butylamine were used.

$^1$H-NMR (CDCl$_3$, ppm): 0.93(3H,t,J=7.4 Hz), 1.31(2H, d,J=7.0 Hz), 1.44(3H,t,J=7.0 Hz), 1.52–1.80(2H,m), 3.52 (2H,t,J=8.5 Hz), 3.70–3.93(2H,m), 4.47(2H,q,J=7.0 Hz), 5.78–5.95(1H,m), 6.57(1H,d,J=2.4 Hz), 8.04(1H,d,J=2.4 Hz).

EXAMPLE 93

Preparation of ethyl 8-cyclopentyl-6,7-dihydro-3-nitro-8H-pyrrolo[3,2-e]pyrazolo[1,5-a]pyrimidine-5-carboxylate:

While stirring at 25° C. or lower, 3.9 ml of 90% nitric acid were added dropwise to 7.8 ml of concentrated sulfuric acid, and the resultant mixed acid was stirred for 15 minutes under the same conditions. While stirring at −5 to 0° C., 1.16 g (3.87 mmol) of 8-cyclopentyl-6,7-dihydro-8H-pyrrolo[3,2-e]pyrazolo[1,5-a]pyrimidine-5-carboxylate as remained solid were gradually added to the mixed acid. After the resultant mixture was stirred for 5 minutes under the same conditions, the reaction mixture was poured into 200 ml of ice water and extracted with chloroform (100 ml×2). After all the chloroform layers were put together and dried over anhydrous sodium sulfate, the solvent was distilled off. The residue was subjected to column chromatography on silica gel (ethyl acetate:n-hexane=1:1) to obtain 0.76 g (yield: 57.0%) of the intended product.

$^1$H-NMR (CDCl$_3$, ppm): 1.47(3H,t,J=7.3 Hz), 1.65–1.90 (6H,m), 1.95–2.15(2H,m), 3.58(2H,t,J=8.9 Hz), 4.00(2H,t, J=8.9 Hz), 4.46(2H,q,J=7.3 Hz), 5.85–6.05(1H,m), 8.67(1H, s).

EXAMPLE 94

Preparation of ethyl 8-sec-butyl-6,7-dihydro-3-nitro-8H-pyrrolo[3,2-e]pyrazolo[1,5-a]pyrimidine-5-carboxylate:

The intended product was obtained in an amount of 0.147 g (yield: 38.7%) in the same manner as in Example 93 except that 0.33 g of ethyl 8-sec-butyl-6,7-dihydro-8H-pyrrolo[3,2-e]pyrazolo[1,5-a]pyrimidine-5-carboxylate were used.

$^1$H-NMR (CDCl$_3$, ppm): 0.96(3H,t,J=7.3 Hz), 1.37(3H, d,J=6.5 Hz), 1.47(3H,t,J=7.0 Hz), 1.64–1.80(2H,m), 3.58 (3H,t,J=7.3 Hz), 3.82–4.04(2H,m), 4.46(2H,q,J=7.0 Hz), 5.73(1H,s,J=6.5 Hz), 8.67(1H,s).

EXAMPLE 95

Preparation of 5-(benzyloxymethyl)-8-sec-butyl-6,7-dihydro-8H-pyrolo[3,2-e]pyrazolo[1,5-a]pyrimidine:

In 5.0 ml of dimethylformamide were dissolved 0.44 g of 5-(benzyloxymethyl)-7-chloro-6-(2-chloroethyl)pyrazolo-[1,5-a]pyrimidine. To the solution, were added 0.15 g of sec-butylamine and 0.26 ml of triethylamine. The mixture was stirred for 1 hour at room temperature and then for 3 hours in an oil bath heated to 100–110° C. Additional 0.06 g of sec-butylamine were added, and the resultant mixture was stirred for 6.3 hours at the same temperature. After the solvent was distilled off under reduced pressure, and 1N hydrochloric acid was added to the resudue, the mixture was extracted with chloroform. After the chloroform layer was washed with a saturated saline solution and then dried over anhydrous sodium sulfate, the solvent was distilled off under reduced pressure. The resultant crude product was subjected to column chromatography on silica gel (elution solvent: hexane:ethyl acetate=3:1) to obtain 0.33 g (yield: 75.0%) of the intended product.

$^1$H-NMR (CDCl$_3$, ppm): 0.94(3H,t,J=7.6 Hz), 1.27(3H, d,J=6.5 Hz), 1.55–1.72(2H,m), 3.22(2H,t,J=6.8 Hz), 3.65–3.81(2H,m), 4.58(2H,s), 4.60(2H,s), 5.73(1H,m), 6.35 (1H,d,J=2.4 Hz), 7.23–7.38(5H,m), 7.97(1H,d,J=2.4 Hz).

EXAMPLE 96

Preparation of 5-(benzyloxymethyl)-8-sec-butyl-6,7-dihydro-8H-pyrolo[3,2-e]pyrazolo[1,5-a]pyrimidine hydrochloride:

In 3.0 ml of ethanol were dissolved 0.26 g of 5-(benzyloxymethyl)-8-sec-butyl-6,7-dihydro-8H-pyrolo[3,2-e]-pyrazolo[1,5-a]pyrimidine. While cooling with ice water, 210 μl of 4N hydrogen chloride in ethyl acetate were added to the solution, and the mixture was stirred for 5 minutes as it is and then for 20 minutes at room temperature. Crystals formed were collected by filtration to obtain 0.2 g (yield: 69.4%) of the intended product.

IR (KBr tablet, cm$^{-1}$): 1620, 1470. m.p.:192–194° C.
$^1$H-NMR (CDCl$_3$, ppm): 0.95(3H,t,J=7.6 Hz), 1.37(3H,d,J= 6.5 Hz), 1.74(2H,m), 3.24(2H,t,J=8.9 Hz), 3.97(2H,m), 4.69 (2H,s), 4.99(2H,s), 5.94(1H,m), 6.75(1H,d,J=2.2 Hz), 7.27–7.65(5H,m), 8.02(1H,d,J=2.2 Hz).

Test Example 1
Tracheodilative effect (in vitro):

With respect to the compounds (1) according to the present invention, the tracheodilative effect useful in treatment and/or prevention of respiratory diseases such as asthma was made into investigation by the Magnus method. More specifically, a male Hartley albino guinea pig (250–300 g) was blow on the head and exsanguinated to death to enucleate its trachea. Strip specimens were prepared from the trachea. Each of the specimens was suspended in an organ bath filled with a Krebs-Henseleit solution kept at 37° C. with supply of a mixed gas (95% O$_2$, 5% CO$_2$). A static tension of 1.0 g was loaded to record an isometric tension. Each of test compounds was cumulatively administered to the specimens separately contracted with 3×10$^{-7}$ M carbachol and 10$^{-6}$ M histamine to investigate its relaxing effect. After the cumulative administration, 10$^{-4}$ M papaverine was administered to confirm the maximum relaxing effect on the trachea specimen. The maximum relaxation was regarded as 100%, and a negative logarithmic value of the concentration of the test compound, at which the specimen was relaxed by 50%, was calculated out, thereby regarding it as a pIC$_{50}$ value. The results are shown in Table 1. The test revealed that the compounds of the present invention represented by the general formula (1) and/or the physiologically acceptable salts thereof have an excellent tracheodilative effect. It was also found that a nitro group is preferable as the substituent of R$^3$.

TABLE 1

| Compound | Carbachol contraction | Histamine contration |
|---|---|---|
| Compound 1 | 5.34 | 5.74 |
| Compound 2 | 5.40 | 5.69 |
| Compound 3 | 5.67 | 5.74 |
| Compound 4 | 5.12 | 5.79 |
| Compound 5 | 5.15 | 5.75 |
| Compound 6 | 4.36 | 5.01 |
| Compound 7 | 4.66 | <4.0 |
| Compound 9 | 3.60 | 4.03 |
| Compound 10 | 3.64 | 1.69 |
| Compound 11 | 4.29 | <4.0 |
| Compound 12 | 4.18 | 5.05 |
| Compound 13 | 4.83 | 5.08 |
| Compound 14 | 3.33 | 4.97 |
| Compound 15 | 4.48 | 4.48 |
| Compound 16 | 2.10 | 4.30 |
| Compound 17 | 3.18 | 3.59 |
| Compound 25 | 4.33 | 5.47 |
| Compound 26 | 4.42 | 5.04 |
| Compound 27 | 5.64 | 5.21 |
| Compound 30 | 4.32 | 1.13 |
| Compound 33 | 2.93 | 2.61 |
| Compound 36 | 3.43 | 4.78 |
| Compound 37 | 4.63 | 4.75 |
| Compound 38 | 4.70 | 5.12 |

Test Example 2
Tracheodilative effect (in vitro):

The pIC$_{50}$ values of the compounds according to the present invention on contraction by LTD$_4$ (concentration: 10$^{-6}$ M), CTA$_2$ (concentration: 10$^{-7}$ M) and OA (concentration: 1 mg/ml) were determined by using the enucleated trachea in accordance with the Magnus method in the same manner as in Test Example 1. The results are shown in Table 2. It was found that the compounds of the present invention represented by the general formula (1) and/or the physiologically acceptable salts thereof are effective on the contraction by these agents.

TABLE 2

| Compound | LTD$_4$ contraction | CTA$_2$ contraction | OA contraction |
|---|---|---|---|
| Compound 1 | 5.52 | 5.72 | Not run |
| Compound 2 | 5.32 | 5.78 | Not run |
| Compound 3 | 5.67 | 5.86 | 5.72 |
| Compound 4 | 5.63 | 5.87 | Not run |
| Compound 5 | 5.55 | 5.81 | Not run |
| Compound 27 | 5.69 | 5.57 | 6.43 |

Test Example 3
Inhibitory effect on airway-constriction (in vivo):

A group of 6 male Hartley albino guinea pigs (250–350 g) was anesthetized with pentobarbital and trachea, carotid artery and jugular vein were cannulated. The experiment was performed by connecting the tracheotomic cannula to a respirator incorporated into a circuit of a bronchospasm transducer (modified Konzet-Lössler method), arresting the spontaneous respiration of each guinea pig by excising its diaphragm and then practicing artificial ventilation, and an airway-constriction was determined by using an overflow rate of ventilation as an index. At the same time, its blood pressure was monitored by means of an amplifier for sphygmomanometry through the carotid artery cannula. Acetylcholine (20 µg/kg) or histamine (15 µg/kg) was intravenously administered upon elapsed time of 0.5, 5 and 10 minutes after a test compound (1 mg/ml/kg) dissolved in 0.1N hydrochloric acid was intravenously administered, thereby observing the airway-constriction elicited. For the sake of comparison, theophylline (6 mg/ml/kg) commonly and widely used in the treatment for asthma was used. The inhibitory effect on the airway-constriction was expressed as an inhibitory rate. The results are shown together with changes in blood pressure (unit: mmHg) in Table 3. The test revealed that all the compounds according to the present invention scarcely affect the blood pressure though they have an excellent inhibitory effect on airway constriction.

TABLE 3

| Compound | Acetylcholine | Histamine | Average lowering in blood pressure |
|---|---|---|---|
| Theophylline (6 mg/kg) | 62 | 76.8 | 13.11 |
| Compound 3 (1 mg/kg) | 51.2 | 55.9 | 1.03 |
| Compound 5 (1 mg/kg) | 83.1 | 67.3 | 9.71 |
| Compound 19 (1 mg/kg) | 31 | −9.2 | 4.55 |
| Compound 20 (1 mg/kg) | 58.6 | 76.3 | 4.08 |
| Compound 27 (1 mg/kg) | 23.8 | 7.1 | −0.68 |

Test Example 4
Inhibitory effect on airway-constriction (in vivo):

The effect of the compounds according to the present invention by oral administration on airway constriction was investigated in the same manner as in Test Example 3 except that esophagus was canulated to administer a test compound (100 mg/2 ml/kg) suspended in 1% CMC through this esophageal cannula, and acetylcholine and histamine were intravenously administered upon elapsed time of 15, 30, 60 and 120 minutes after the administration of the test compound. The results are shown in Table 4. The test revealed that all the compounds according to the present invention scarcely affect the blood pressure though they have an excellent inhibitory effect on airway constriction. Incidentally, the values of lowering in blood pressure were those upon elapsed time of 120 minutes after the administration of the test compound, and the dose of the comparative theophylline was 100 mg/kg. Further, no mortal case was recognized even in the dose of 100 mg/kg, so that the compounds according to the present invention are considered to have high safety.

TABLE 4

| Compound | Acetylcholine | Histamine | Average lowering in blood pressure |
|---|---|---|---|
| Theophylline | 55.3 | 86.3 | 24.75 |
| Compound 3 | 36.5 | 43.1 | 13.03 |
| Compound 5 | 53.7 | 38.9 | 14.81 |
| Compound 19 | 23.8 | 18.7 | 18.66 |
| Compound 20 | 83.6 | 91.2 | 34.40 |
| Compound 27 | 11.5 | 13.4 | 10.4 |
| Compound 37 | 58.2 | 57.4 | 19.1 |
| Compound 38 | 74.4 | 58.5 | 3.8 |
| Compound 87 | 64.8 | 79.5 | 29.1 |

INDUSTRIAL APPLICABILITY

The compounds (1) according to the present invention and salts thereof have excellent tracheobronchodilative effect and inhibitory effect on airway constriction and act only weakly on circulatory organs, and are hence useful in preventing and treating a respiratory disease such as asthma, chronic obstructive pulmonary disease, bronchitis or pneumonia.

We claim:
1. A pyrrolopyrazolopyrimidine compound represented by the following general formula (1):

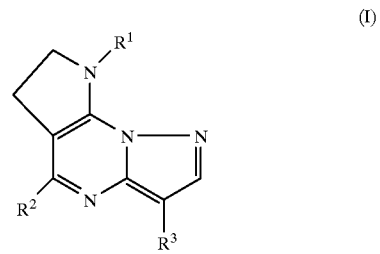

(I)

wherein $R^1$ represents a linear, branched or cyclic alkyl group, $R^2$ represents a hydrogen or halogen atom, an alkyl group which may be substituted, an amino group which may be substituted, a carboxyl group, an alkoxycarbonyl group, a carbamoyl group, or an alkylcarbamoyl group, and $R^3$ represents a nitro group, an amino group, a nitrogen-containing heterocyclic group, an alkylsulfonylamino group which may be substituted by halogen, $R^4$CONH— (in which $R^4$ represents an alkyl, halogenoalkyl, carboxyl or alkoxycarbonyl group), or $R^5$CO— (in which $R^5$ represents an amino, hydroxyl, alkyl, alkoxy, halogenoalkyl or heterocycle-amino group), or a salt thereof.

2. The compound or the salt thereof according to claim 1, wherein $R^1$ is a linear, branched or cyclic alkyl group having 1–10 carbon atoms, $R^2$ is a hydrogen or halogen atom, an amino group which may be substituted, an alkyl group which may be substituted and has 1–10 carbon atoms, a carboxyl group, or an alkoxycarbonyl group having 2–11 carbon atoms in total, and $R^3$ is a nitro group, an amino group, a tetrazolyl group, a $C_{1-10}$-alkylsulfonylamino group which may be substituted by halogen, $R^4$CONH— (in which $R^4$ is a $C_{1-10}$-alkyl, $C_{1-10}$-halogenoalkyl, carboxyl or alkoxycarbonyl group having 2–11 carbon atoms in total), or $R^5$CO— (in which $R^5$ is an amino, hydroxyl, $C_{1-10}$-alkyl, $C_{1-10}$-alkoxy, $C_{1-10}$-halogenoalkyl or tetrazolylamino group).

3. A pharmaceutical composition comprising the compound or the salt thereof according to claim 1 or 2 as an active ingredient.

4. A pharmaceutical composition according to claim 3, which is an agent for a respiratory disease.

5. A medicinal composition comprising the compound or the salt thereof according to claim 1 or 2 and a pharmaceutically acceptable carrier.

6. A method for the treatment of a respiratory disease, which comprises administering the compound or the salt thereof according to claim 1 or 2.

7. A process for the preparation of a pyrrolopyrazolopyrimidine compound represented by the following general formula (1):

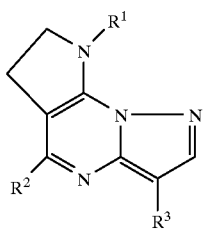

(I)

wherein $R^1$ represents a linear, branched or cyclic alkyl group, $R^2$ represents a hydrogen or halogen atom, an alkyl group which may be substituted, an amino group which may be substituted, a carboxyl group, an alkoxycarbonyl group, a carbamoyl group, or an alkylcarbamoyl group, and $R^3$ represents a nitro group, an amino group, a heterocyclic group, an alkylsulfonylamino group which may be substituted by halogen, $R^4CONH-$ (in which $R^4$ represents an alkyl, halogenoalkyl, carboxyl or alkoxycarbonyl group), or $R^5CO-$ (in which $R^5$ represents an amino, hydroxyl, alkyl, alkoxy, halogenoalkyl or heterocycle-amino group), or a salt thereof, which comprises reacting an amine represented by the formula $H_2N-R^1$ (in which $R^1$ has the same meaning as defined above) with a compound represented by the following general formula (2):

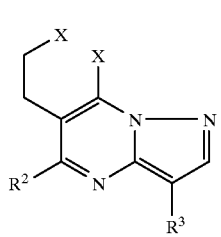

(2)

wherein $R^2$ and $R^3$ have the same meanings as defined above, and X represents a halogen atom.

8. A process for the prepartion of a pyrrolopyrazolopyrimidine compound represented by the following general formula (1):

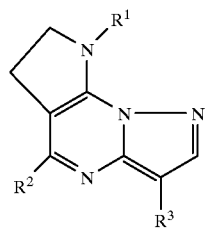

(I)

wherein $R^1$ represents a linear, branched or cyclic alkyl group, $R^2$ represents a hydrogen or halogen atom, an alkyl group which may be substituted, an amino group which may be substituted, a carboxyl group, an alkoxycarbonyl group, a carbamoyl group, or an alkylcarbamoyl group, and $R^3$ represents a nitro group, an amino group, a heterocyclic group, an alkylsulfonylamino group which may be substituted by halogen, $R^4CONH-$ (in which $R^4$ represents an alkyl, halogenoalkyl, carboxyl or alkoxycarbonyl group), or $R^5CO-$ (in which $R^5$ represents an amino, hydroxyl, alkyl, alkoxy, halogenoalkyl or heterocycle-amino group), or a salt thereof, which comprises reacting a halogenating agent with a compound represented by the following formula (3):

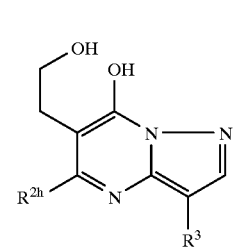

(3)

wherein $R^{2h}$ represents a hydrogen, a hydroxyl group, an alkyl group which may be substituted, an amino group which may be substituted, a carboxyl group, an alkoxycarbonyl group, a carbamoyl group, or an alkylcarbamoyl group, and $R^3$ has the same meanings as defined above, or a tautomer thereof to form a compound represented by the following general formula (2):

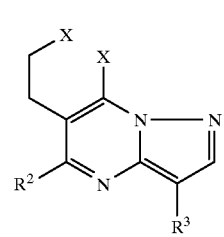

(2)

wherein $R^2$ and $R^3$ have the same meanings as defined above, and X represents a halogen atom, and reacting this compound with an amine represented by the formula $H_2N-R^1$ (in which $R^1$ has the same meaning as defined above).

9. A process for the preparation of a pyrrolopyrazolopyrimidine compound represented by the following general formula (1-N):

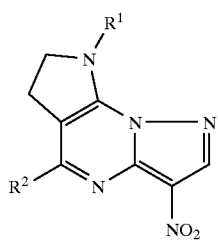

(1-N)

wherein R¹ represents a linear, branched or cyclic alkyl group, and R² represents a hydrogen or halogen atom, an alkyl group which may be substituted, an amino group which may be substituted, a carboxyl group, an alkoxycarbonyl group, a carbamoyl group, or an alkylcarbamoyl group, or a salt thereof, which comprises nitrating a compound represented by the following formula (1-H):

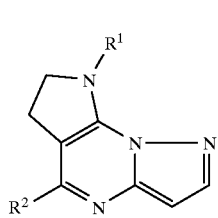

(1-H)

wherein R¹ and R² have the same meanings as defined above.

10. A process for the preparation of a pyrazolopyrimidine compound represented by the following general formula (2-N):

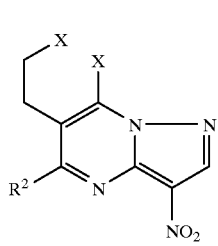

(2-N)

wherein R² represents a hydrogen, a hydroxyl group, an alkyl group which may be substituted, an amino group which may be substituted, a carboxyl group, an alkoxycarbonyl group, a carbamoyl group, or an alkylcarbamoyl group, and X represents a halogen atom, which comprises nitrating a compound represented by the following general formula (2-H):

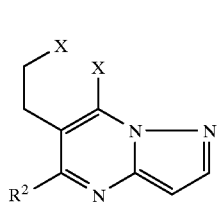

(2-H)

wherein R² and X have the same meanings as defined above.

11. A process for the preparation of a pyrrolopyrazolopyrimidine compound represented by the following general formula (1-N):

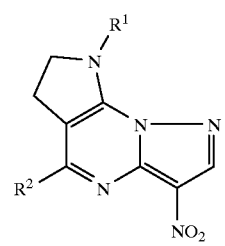

(1-N)

wherein R¹ represents a linear, branched or cyclic alkyl group, and R² represents a hydrogen or halogen atom, an alkyl group which may be substituted, an amino group which may be substituted, a carboxyl group, an alkoxycarbonyl group, a carbamoyl group, or an alkylcarbamoyl group, or a salt thereof, which comprises reacting a halogenating agent with a compound represented by the following formula (3-H):

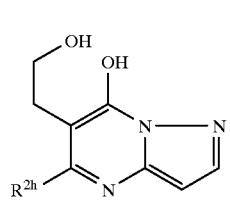

(3-H)

wherein $R^{2h}$ represents a hydrogen, a hydroxyl group, an alkyl group which may be substituted, an amino group which may be substituted, a carboxyl group, an alkoxycarbonyl group, a carbamoyl group, or an alkylcarbamoyl group, or a tautomer thereof to form a compound represented by the following general formula (2-H):

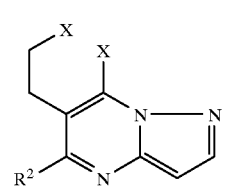

(2-H)

wherein R² has the same meaning as defined above, and X represents a halogen atom, and nitrating this compound (2-H) to form a compound represented by the following general formula (2-N):

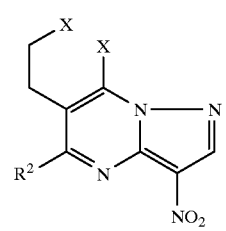

(2-N)

wherein R² and X have the same meanings as defined above, and reacting this compound (2-N) with an amine represented by the formula H₂N—R¹ (in which R¹ has the same meaning as defined above).

12. A process for the preparation of a compound represented by the following general formula (1-c):

(1-c)

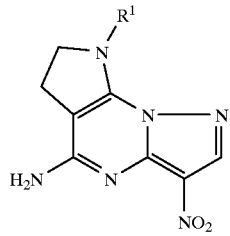

wherein R¹ represents a linear, branched or cyclic alkyl group, or a salt thereof, which comprises subjecting a compound represented by the following formula (1-b):

(1-b)

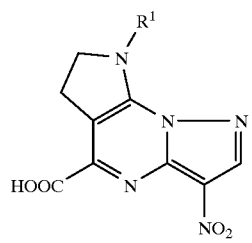

wherein R¹ has the same meaning as defined above, to a Curtius rearrangement reaction.

13. A process for the preparation of a pyrrolopyrazolopyrimidine compound represented by the following general formula (1-g):

(1-g)

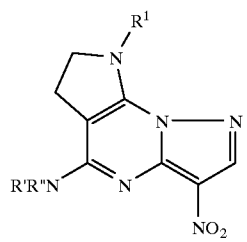

wherein R¹ represents a linear, branched or cyclic alkyl group, and R' and R" independently represent a hydrogen atom, or an alkyl or cycloalkyl group, or may form a heterocyclic ring, which may contain an additional heteroatom, together with the adjacent nitrogen atom, or a salt thereof, which comprises reacting a primary or secondary amine (in which R' and R" have the same meanings as defined above) with a compound represented by the following general formula (1-f):

(1-f)

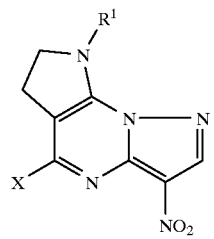

wherein R¹ has the same meaning as defined above, and X represents a halogen atom.

14. A pyrrolopyrazolopyrimidine compound represented by the following general formula (1-m):

(1-m)

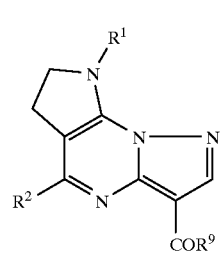

wherein R¹ represents a linear, branched or cyclic alkyl group, R2 represents a hydrogen or halogen atom, an alkyl group which may be substituted, an amino group which may be substituted, a carboxyl group, an alkoxycarbonyl group, a carbamoyl group, or an alkylcarbamoyl group, and R⁹ represents an alkyl group or halogenoalkyl group, or a salt thereof, which comprises acylating a compound represented by the following general formula (1-H):

(1-H)

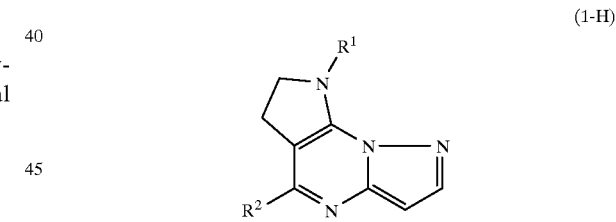

15. A process for the preparation of a pyrrolopyrazolopyrimidine compound represented by the following general formula (1-H):

(1-H)

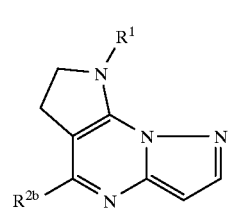

wherein R¹ represents a linear, branched or cyclic alkyl group, and R²ᵇ represents a hydrogen or halogen atom, an alkyl group which is substituted, an amino group which may be substituted, a carboxyl group, an alkoxycarbonyl group, a carbamoyl group, or an alkylcarbamoyl group, or a salt thereof, which comprises reacting a halogenating agent with a compound represented by the following formula (3-H):

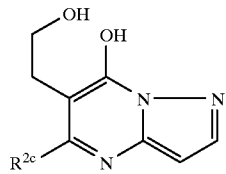

(3-H)

wherein $R^{2c}$ represents a hydrogen, a hydroxyl group, an alkyl group which is substituted, an amino group which may be substituted, a carboxyl group, an alkoxycarbonyl group, a carbamoyl group, or an alkylcarbamoyl group, or a tautomer thereof to form a compound represented by the following general formula (2-H):

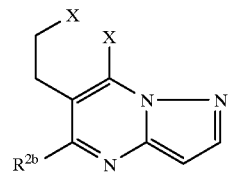

(2-H)

wherein $R^{2b}$ has the same meaning as defined above, and X represents a halogen atom, and then reacting this compound with an amine represented by the formula $H_2N-R^1$ (in which $R^1$ has the same meaning as defined above).

* * * * *

UNITED STATES PATENT AND TRADEMARK OFFICE
CERTIFICATE OF CORRECTION

PATENT NO. : 5,942,515

DATED : August 24, 1999

INVENTOR(S): NAMIKI ET AL

It is certified that an error appears in the above-identified patent and that said Letters Patent is hereby corrected as shown below:

Column 58, line 48, after formula (1-H), insert --wherein $R^1$ and $R^2$ have the same meanings as defined above.--

Signed and Sealed this

Tenth Day of April, 2001

NICHOLAS P. GODICI

Attest:

Attesting Officer

Acting Director of the United States Patent and Trademark Office